United States Patent [19]
Quax et al.

[11] Patent Number: 5,457,032
[45] Date of Patent: Oct. 10, 1995

[54] MUTATED β-LACTAM ACYLASE GENES

[75] Inventors: Wilhelmus J. Quax, Voorschoten; Onno Misset, Delft; Jan M. Van Der Laan, Groningen; Herman B. M. Lenting, Pijnacker, all of Netherlands

[73] Assignee: Gist-brocades NV, Delft, Netherlands

[21] Appl. No.: 731,157

[22] Filed: May 9, 1991

[30] Foreign Application Priority Data

Apr. 18, 1990 [EP] European Pat. Off. .............. 90200962

[51] Int. Cl.⁶ ........................... C12N 9/84; C12N 15/55; C12P 37/00
[52] U.S. Cl. ................... 435/43; 435/44; 435/45; 435/230; 435/228; 435/320.1; 435/252.3; 536/23.2
[58] Field of Search ..................... 435/230, 228, 435/320.1, 252.3, 43, 44, 45; 536/23.2

[56] References Cited

U.S. PATENT DOCUMENTS

| | | | |
|---|---|---|---|
| 4,774,179 | 9/1988 | Ichikawa et al. | 435/51 |
| 5,168,048 | 12/1992 | Quax | 435/66.1 |
| 5,192,678 | 3/1993 | Iwami et al. | 435/228 |

FOREIGN PATENT DOCUMENTS

| | | |
|---|---|---|
| 0283218 | 9/1988 | European Pat. Off. . |
| 0322032 | 6/1989 | European Pat. Off. . |

OTHER PUBLICATIONS

Schumacher, et al., "Penicillin acylase from *E. coli*: unique gene—protein relation," *Nucleic Acids Research*, vol. 14, No. 14 (1986).

Barbero, et al., "Complete nucleotide sequence of the penicillin acylase gene from *Kluyvera citrophilia*," *Gene*, vol. 49, pp. 69–80 (1986).

Daumy, "Role of protein subunits in *Proteus rettgeri* Penicillin G Acylase," *J. Bacteriol.*, vol. 163, No. 3, Sep. 1985 pp. 1279–1281.

Williams, et al., "Penicillin G Acylase (E.C.3.4.1.11) substrate specificity modification by in vitro mutagenesis," *Cell Biochem.* 9B/supplement (1985) p. 99, No. 656.

Forney, et al. "Selection of amidases with novel substrate specificities from Penicillin Amidase of *Escherichia coli*," *Applied & Environmental Microbiology*, vol. 55, No. 10, Oct. 1989 pp. 2550–2555.

Forney, et al., "Alteration of the catalytic efficiency of Penicillin Amidase from *Escherichia coli*," *Applied & Environmental Microbiology*, vol. 55, No. 10, pp. 2556–2560 1989.

Matsuda, A., et al. (1987) J. Bacteriol. 169 (12), 5815–5820.

Matsuda A. et al. (1987) J. Bateriol. 169 (12), 5821–5826.

Norrander, J. et al (1983) Gene 26, 101–106.

Stanssens, P. et al. (1989) Nuc. Acids Res. 12(12) 4441–4454.

*Primary Examiner*—Charles L. Patterson, Jr.
*Attorney, Agent, or Firm*—Barbara Rae-Venter

[57] ABSTRACT

New mutant β-lactam acylases are provided exhibiting altered substrate specificities. These β-lactam acylases are obtained by expression of a gene encoding said β-lactam acylase and having an amino acid sequence which differs at least in one amino acid from the wild-type β-lactam acylase.

9 Claims, 35 Drawing Sheets

```
                                       510       520       530       540
                                   ATGCAGAAAGGGCTTGTTCGTACCGGGCTTGT
                                     M  Q  K  G  L  V  R  T  G  L  V
                                                                   1
        550       560       570       580       590       600
   GGCCGCTGGTTTGATCTTGGGTTGGGCGGGGGCACCGACCCACGCGCAAGTGCAGTCGGT
     A  A  G  L  I  L  G  W  A  G  A  P  T  H  A  Q  V  Q  S  V
    12
        610       620       630       640       650       660
   AGAGGTGATGCGGGACAGTTATGGCGTGCCGCACGTCTTTGCCGACAGCCACTATGGCTT
     E  V  M  R  D  S  Y  G  V  P  H  V  F  A  D  S  H  Y  G  L
    32
        670       680       690       700       710       720
   GTATTACGGCTATGGTTATGCGGTCGCCCAAGACCGTCTGTTCCAGATGGACATGGCGCG
     Y  Y  G  Y  G  Y  A  V  A  Q  D  R  L  F  Q  M  D  M  A  R
    52
        730       740       750       760       770       780
   TCGCTCCTTTGTCGGCACAACCGCCGCCGTCTTAGGCCCTGGTGAGCAAGATGCCTACGT
     R  S  F  V  G  T  T  A  A  V  L  G  P  G  E  Q  D  A  Y  V
    72
        790       800       810       820       830       840
   CAAGTACGACATGCAGGTGCGGCAGAACTTCACCCCGGCTTCCATACAGCGGCAGATCGC
     K  Y  D  M  Q  V  R  Q  N  F  T  P  A  S  I  Q  R  Q  I  A
    92
        850       860       870       880       890       900
   GGCCTTGTCCAAGGATGAGCGCGATATTTTTCGTGGCTATGCCGATGGCTATAACGCCTA
     A  L  S  K  D  E  R  D  I  F  R  G  Y  A  D  G  Y  N  A  Y
   112
        910       920       930       940       950       960
   TCTGGAGCAGGTGCGGCGTCGCCCTGAGTTGCTGCCCAAAGAATATGTGGATTTTGATTT
     L  E  Q  V  R  R  R  P  E  L  L  P  K  E  Y  V  D  F  D  F
   132
        970       980       990      1000      1010      1020
   CCAGCCCGAGCCGCTGACCGACTTTGATGTGGTCATGATCTGGGTGGGCTCCATGGCCAA
     Q  P  E  P  L  T  D  F  D  V  V  M  I  W  V  G  S  M  A  N
   152
       1030      1040      1050      1060      1070      1080
   TCGCTTCTCCGACACGAATCTGGAAGTGACGGCACTGGCCATGCGTCAGTCTCTGGAGAA
     R  F  S  D  T  N  L  E  V  T  A  L  A  M  R  Q  S  L  E  K
   172
       1090      1100      1110      1120      1130      1140
   ACAGCACGGCCCGGAACGAGGCCGTGCCTTGTTTGATGAGCTGCTGTGGATCAATGACAC
     Q  H  G  P  E  R  G  R  A  L  F  D  E  L  L  W  I  N  D  T
   192
       1150      1160      1170      1180      1190      1200
   AACAGCTCCCACTACGGTTCCGGCCCCCGCTGCCGAGCACAAGCCGCAGGCACAAGCAGG
     T  A  P  T  T  V  P  A  P  A  A  E  H  K  P  Q  A  Q  A  G
   212
       1210      1220      1230      1240      1250      1260
   GACGCAGGATCTGGCTCATGTTTCCTCGCCAGTACTGGCTACCGAGCTAGAGCGCCAGGA
     T  Q  D  L  A  H  V  S  S  P  V  L  A  T  E  L  E  R  Q  D
   232
       1270      1280      1290      1300      1310      1320
   CAAGCACTGGGGCGGCCGTGGCCCGGACTTCGCGCCCAAGGCTAGCAACCTGTGGAGCAC
     K  H  W  G  G  R  G  P  D  F  A  P  K  A  S  N  L  W  S  T
   252
```

FIG.5A

```
          1330      1340      1350      1360      1370      1380
TCGCCCCGAGCGAGTGCAGGAGGGCTCGACCGTACTGATCAACGGCCCACAGTTTGGCTG
  R   P   E   R   V   Q   E   G   S   T   V   L   I   N   G   P   Q   F   G   W
272
          1390      1400      1410      1420      1430      1440
GTACAACCCGGCCTACACCTATGGCATTGGCTTGCATGGCGCCGGCTTCGATGTGGTGGG
  Y   N   P   A   Y   T   Y   G   I   G   L   H   G   A   G   F   D   V   V   G
292
          1450      1460      1470      1480      1490      1500
TAATACGCCTTTTGCCTATCCGATCGTACTGTTTGGCACCAATAGCGAGATTGCCTGGGG
  N   T   P   F   A   Y   P   I   V   L   F   G   T   N   S   E   I   A   W   G
312
          1510      1520      1530      1540      1550      1560
GGCGACTGCTGGCCCGCAAGATGTGGTGGACATATATCAGGAAAAATTGAACCCCTCGCG
  A   T   A   G   P   Q   D   V   V   D   I   Y   Q   E   K   L   N   P   S   R
332
          1570      1580      1590      1600      1610      1620
TGCCGATCAGTACTGGTTCAACAATGCCTGGCGCACGATGGAGCAGCGCAAGGAACGTAT
  A   D   Q   Y   W   F   N   N   A   W   R   T   M   E   Q   R   K   E   R   I
352
          1630      1640      1650      1660      1670      1680
CCAGGTACGCGGTCAGGCTGATCGGGAAATGACGATCTGGCGCACCGTGCACGGCCCTGT
  Q   V   R   G   Q   A   D   R   E   M   T   I   W   R   T   V   H   G   P   V
372
          1690      1700      1710      1720      1730      1740
GATGCAGTTTGATTACGATCAGGGCGCGGCGTACAGCAAGAAACGCAGCTGGGATGGCTA
  M   Q   F   D   Y   D   Q   G   A   A   Y   S   K   K   R   S   W   D   G   Y
392
          1750      1760      1770      1780      1790      1800
TGAGGTGCAGTCCTTGCTAGCCTGGTTGAACGTGGCCAAGGCCCGCAACTGGACGGAGTT
  E   V   Q   S   L   L   A   W   L   N   V   A   K   A   R   N   W   T   E   F
412
          1810      1820      1830      1840      1850      1860
TCTGGATCAAGCCAGCAAGATGGCGATTTCGATCAACTGGTACTACGCCGACAAGCACGG
  L   D   Q   A   S   K   M   A   I   S   I   N   W   Y   Y   A   D   K   H   G
432
          1870      1880      1890      1900      1910      1920
CAATATTGGTTATGTCTCGCCGGCCTTCCTGCCCCAGCGTCCTGCCGATCAGGACATCCG
  N   I   G   Y   V   S   P   A   F   L   P   Q   R   P   A   D   Q   D   I   R
452
          1930      1940      1950      1960      1970      1980
TGTCCCTGCCAAGGGGGATGGCAGCATGGAGTGGCTGGGCATCAAGAGTTTCGACGCGAT
  V   P   A   K   G   D   G   S   M   E   W   L   G   I   K   S   F   D   A   I
472
          1990      2000      2010      2020      2030      2040
TCCCAAAGCCTACAATCCACCCCAGGGCTATCTGGTCAACTGGAACAACAAGCCTGCGCC
  P   K   A   Y   N   P   P   Q   G   Y   L   V   N   W   N   N   K   P   A   P
492
          2050      2060      2070      2080      2090      2100
GGACAAAACCAATACGGATACTTACTATTGGACCTATGGCGACCGCATGAATGAACTGGT
  D   K   T   N   T   D   T   Y   Y   W   T   Y   G   D   R   M   N   E   L   V
512
          2110      2120      2130      2140      2150      2160
CAGTCAGTACCAGCAGAAAGACCTCTTCAGTGTGCAGGAGATCTGGGAGTTCAATCAAAA
  S   Q   Y   Q   Q   K   D   L   F   S   V   Q   E   I   W   E   F   N   Q   K
532
```

FIG.5B

```
           2170        2180        2190        2200        2210        2220
AGCCTCCTATAGCGATGTGAACTGGCGCTACTTCCGCCCACATCTGGAAAAGCTGGCGCA
   A  S  Y  S  D  V  N  W  R  Y  F  R  P  H  L  E  K  L  A  Q
 552
           2230        2240        2250        2260        2270        2280
ACAGCTGCCGGCCGACGATAGCAGCAAGGCGGCGCTGACGATGTTGCTCGCCTGGGATGG
   Q  L  P  A  D  D  S  S  K  A  A  L  T  M  L  L  A  W  D  G
 572
           2290        2300        2310        2320        2330        2340
AATGGAACAGGATCAGGGAGGGCAAAATGCCGGACCGGCGCGGGTGCTCTTCAAGACCTG
   M  E  Q  D  Q  G  G  Q  N  A  G  P  A  R  V  L  F  K  T  W
 592
           2350        2360        2370        2380        2390        2400
GCTGGAAGAAATGTACAAGCAGGTCTTGATGCCGGTGGTGCCTGAATCGCATCGCGCCAT
   L  E  E  M  Y  K  Q  V  L  M  P  V  V  P  E  S  H  R  A  M
 612
           2410        2420        2430        2440        2450        2460
GTATAGCCAGACTGGTTTTGCCACGCAGCAAGGTCCCAACCCCGGTTCCATCAACTTGAG
   Y  S  Q  T  G  F  A  T  Q  Q  G  P  N  P  G  S  I  N  L  S
 632
           2470        2480        2490        2500        2510        2520
CATGGGCACCAAGGTCTTGTTGCGTGCCTTGGTGCTGGAAGCCCATCCCGATCCCAAGCG
   M  G  T  K  V  L  L  R  A  L  V  L  E  A  H  P  D  P  K  R
 652
           2530        2540        2550        2560        2570        2580
TGTGAATGTCTTTGGTGAGCGTTCGTCTCAGGAAATCATGCACACAGCTTTGCAAAATGC
   V  N  V  F  G  E  R  S  S  Q  E  I  M  H  T  A  L  Q  N  A
 672
           2590        2600        2610        2620        2630        2640
GCAGGCCCGCTTGAGCCAGGAGCAGGGCGCTCAGATGGCGCGCTGGACCATGCCGACCTC
   Q  A  R  L  S  Q  E  Q  G  A  Q  M  A  R  W  T  M  P  T  S
 692
           2650        2660        2670        2680        2690        2700
CGTGCATCGTTTCAGCGACAAGAACTTCACGGGAACCCCGCAGACGATGCCTGGCAATAC
   V  H  R  F  S  D  K  N  F  T  G  T  P  Q  T  M  P  G  N  T
 712
           2710        2720        2730        2740        2750        2760
CTTTGCCTTTACCGGCTATCAGAATCGAGGCACGGAAAATAACCGCGTGGTGTTTGATGC
   F  A  F  T  G  Y  Q  N  R  G  T  E  N  N  R  V  V  F  D  A
 732
           2770        2780        2790        2800        2810        2820
CAAGGGCGTGGAGTTCTGCGACGCCATGCCGCCCGGCCAAAGCGGTTTCACCGACCGCAA
   K  G  V  E  F  C  D  A  M  P  P  G  Q  S  G  F  T  D  R  N
 752
           2830        2840        2850        2860        2870        2880
TGGAGTGCGCAGCCCGCATTATGAGGATCAGCTGAAGTTGTACGAGAACTTCGAGTGCAA
   G  V  R  S  P  H  Y  E  D  Q  L  K  L  Y  E  N  F  E  C  K
 772
           2890        2900        2910        2920        2930        2940
GACGATGGATGTGACGCATGCGGACATTCGTCGTAATGCGCAAAGCAGCACGATGCTGTT
   T  M  D  V  T  H  A  D  I  R  R  N  A  Q  S  S  T  M  L  L
 792
           2950        2960
GATTCAGCCTCAGCCTTAA
   I  Q  P  Q  P  *
 812              816
```

FIG.5C

```
        111        121        131        141        151        161
ATGCTGAGAGTTCTGCACCGGGCGGCGTCCGCCTTGGTTATGGCGACTGTGATCGGCCTT
 M  L  R  V  L  H  R  A  A  S  A  L  V  M  A  T  V  I  G  L 171        181        191        201        211        221
GCGCCCGCCGTCGCCTTTGCGCTGGCCGAGCCGACCTCGACGCCGCAGGCGCCGATTGCG
 A  P  A  V  A  F  A  L  A  E  P  T  S  T  P  Q  A  P  I  A 231        241        251        261        271        281
GCCTATAAACCGAGAAGCAATGAGATCCTGTGGGACGGCTACGGCGTCCCGCACATCTAC
 A  Y  K  P  R  S  N  E  I  L  W  D  G  Y  G  V  P  H  I  Y 291        301        311        321        331        341
GGCGTCGACGCGCCCTCAGCCTTCTACGGCTATGGCTGGGCCCAGGCGCGCAGCCAGGGC
 G  V  D  A  P  S  A  F  Y  G  Y  G  W  A  Q  A  R  S  Q  G 351        361        371        381        391        401
GACAATATCCTGCGCCTGTATGGAGAAGCGCGGGGCAAGGGGGCCGAATACTGGGGCCCG
 D  N  I  L  R  L  Y  G  E  A  R  G  K  G  A  E  Y  W  G  P 411        421        431        441        451        461
GATTACGAACAGACGACCGTCTGGCTGCTGACCAACGGCGTGCCGGAGCGCGCTCAGCAG
 D  Y  E  Q  T  T  V  W  L  L  T  N  G  V  P  E  R  A  Q  Q 471        481        491        501        511        521
TGGTATGCGCAGCAGTCGCCTGATTTCCGCGCCAACCTCGACGCCTTCGCGGCGGGCATC
 W  Y  A  Q  Q  S  P  D  F  R  A  N  L  D  A  F  A  A  G  I 531        541        551        561        571        581
AACGCCTATGCGCAGCAGAACCCCGACGACATCTCGCCCGACGTGCGGCAGGTGCTGCCG
 N  A  Y  A  Q  Q  N  P  D  D  I  S  P  D  V  R  Q  V  L  P 591        601        611        621        631        641
GTTTCCGGCGCCGACGTGGTGGCCCACGCCCACCGCCTGATGAACTTCCTCTATGTCGCG
 V  S  G  A  D  V  V  A  H  A  H  R  L  M  N  F  L  Y  V  A 651        661        671        681        691        701
TCGCCCGGCCGCACCCTGGGCGAGGGCGACCCGCCGGACCTGGCCGATCAAGGATCCAAC
 S  P  G  R  T  L  G  E  G  D  P  P  D  L  A  D  Q  G  S  N 711        721        731        741        751        761
TCCTGGGCGGTGGCGCCGGGAAAGACGGCGAACGGGAACGCCCTGCTGCTGCAGAACCCG
 S  W  A  V  A  P  G  K  T  A  N  G  N  A  L  L  Q  N  P 771        781        791        801        811        821
CACCTGTCCTGGACGACGGACTACTTCACCTACTACGAGGCGCATCTCGTCACGCCGGAC
 H  L  S  W  T  T  D  Y  F  T  Y  Y  E  A  H  L  V  T  P  D 831        841        851        861        871        881
TTCGAAATCTATGGCGCGACCCAGATCGGCCTGCCGGTCATCCGCTTCGCCTTCAACCAG
 F  E  I  Y  G  A  T  Q  I  G  L  P  V  I  R  F  A  F  N  Q 891        901        911        921        931        941
CGGATGGGCATCACCAATACCGTCAACGGCATGGTGGGGGCCACCAACTATCGGCTGACG
 R  M  G  I  T  N  T  V  N  G  M  V  G  A  T  N  Y  R  L  T 951        961        971        981        991       1001
CTTCAGGACGGCGGCTATCTGTATGACGGTCAGGTGCGGCCGTTCGAGCGGCCTCAGGCC
```

FIG. 13A

```
        L  Q  D  G  G  Y  L  Y  D  G  Q  V  R  P  F  E  R  P  Q  A 1011      1021      1031      1041      1051      1061
       TCGTATCGCCTGCGTCAGGCGGACGGGACGACGGTCGACAAGCCGTTGGAGATCCGCTCC
        S  Y  R  L  R  Q  A  D  G  T  T  V  D  K  P  L  E  I  R  S 1071      1081      1091      1101      1111      1121
       AGCGTCCATGGCCCGGTCTTCGAGCGCGCGGACGGCACGGCCGTCGCCGTTCGGGTCGCC
        S  V  H  G  P  V  F  E  R  A  D  G  T  A  V  A  V  R  V  A 1131      1141      1151      1161      1171      1181
       GGTCTGGACCGGCCGGGCATGCTCGAGCAGTATTTCGACATGATCACGGCGGACAGCTTC
        G  L  D  R  P  G  M  L  E  Q  Y  F  D  M  I  T  A  D  S  F 1191      1201      1211      1221      1231      1241
       GACGACTACGAAGCCGCTTTGGCGCGGATGCAGGTGCCGACCTTCAACATCGTCTACGCC
        D  D  Y  E  A  A  L  A  R  M  Q  V  P  T  F  N  I  V  Y  A 1251      1261      1271      1281      1291      1301
       GACCGCGAAGGGACCATCAACTACAGCTTCAACGGCGTGGCGCCCAAACGGGCCGAGGGC
        D  R  E  G  T  I  N  Y  S  F  N  G  V  A  P  K  R  A  E  G 1311      1321      1331      1341      1351      1361
       GACATCGCCTTCTGGCAGGGGCTCGTGCCGGGCGATTCCTCGCGTTACCTGTGGACCGAG
        D  I  A  F  W  Q  G  L  V  P  G  D  S  S  R  Y  L  W  T  E 1371      1381      1391      1401      1411      1421
       ACACACCCGCTGGACGATCTGCCGCGCGTCACCAATCCGCCGGGCGGCTTCGTGCAGAAC
        T  H  P  L  D  D  L  P  R  V  T  N  P  P  G  G  F  V  Q  N 1431      1441      1451      1461      1471      1481
       TCCAATGATCCGCCGTGGACGCCGACCTGGCCCGTCACCTACACGCCCAAGGACTTCCCC
        S  N  D  P  P  W  T  P  T  W  P  V  T  Y  T  P  K  D  F  P 1491      1501      1511      1521      1531      1541
       TCCTATCTGGCGCCCCAGACGCCGCATTCCCTGCGTGCGCAACAAAGCGTGCGTCTGATG
        S  Y  L  A  P  Q  T  P  H  S  L  R  A  Q  Q  S  V  R  L  M 1551      1561      1571      1581      1591      1601
       TCCGAGAACGACGACCTGACGCTGGAGCGCTTCATGGCGCTGCAGTTGAGCCATCGCGCC
        S  E  N  D  D  L  T  L  E  R  F  M  A  L  Q  L  S  H  R  A 1611      1621      1631      1641      1651      1661
       GTCATGGCCGACCGCACCTTGCCGGACCTGATCCCGGCCGCCCTGATCGACCCCGATCCC
        V  M  A  D  R  T  L  P  D  L  I  P  A  A  L  I  D  P  D  P 1671      1681      1691      1701      1711      1721
       GAGGTCCAGGCGGCGGCGCGCCTGCTGGCGGCGTGGGATCGCGAGTTCACCAGCGACAGC
        E  V  Q  A  A  A  R  L  L  A  A  W  D  R  E  F  T  S  D  S 1731      1741      1751      1761      1771      1781
       CGCGCCGCCCTGCTGTTCGAGGAATGGGCGCGTCTGTTCGCCGGCCAGAATTTCGCAGGC
        R  A  A  L  L  F  E  E  W  A  R  L  F  A  G  Q  N  F  A  G 1791      1801      1811      1821      1831      1841
       CAGGCCGGCTTCGCCACGCCCTGGTCGCTGGATAAGCCGGTCAGCACGCCTTACGGCGTC
        Q  A  G  F  A  T  P  W  S  L  D  K  P  V  S  T  P  Y  G  V
```

FIG. 13B

```
      1851        1861        1871        1881        1891        1901
CGCGACCCCAAGGCCGCCGTCGATCAACTGCGGACCGCCATCGCCAACACCAAGCGCAAA
  R  D  P  K  A  A  V  D  Q  L  R  T  A  I  A  N  T  K  R  K 1911        1921        1931        1941        1951        1961
TACGGCGCGATCGACCGGCCGTTCGGCGACGCCTCGCGCATGATCCTGAACGACGTGAAT
  Y  G  A  I  D  R  P  F  G  D  A  S  R  M  I  L  N  D  V  N 1971        1981        1991        2001        2011        2021
GTTCCGGGCGCCGCCGGCTACGGCAACCTGGGTTCCTTCCGGGTCTTCACCTGGTCCGAT
  V  P  G  A  A  G  Y  G  N  L  G  S  F  R  V  F  T  W  S  D 2031        2041        2051        2061        2071        2081
CCTGACGAAAACGGGGTTCGCACGCCCGTCCACGGCGAGACGTGGGTGGCGATGATCGAG
  P  D  E  N  G  V  R  T  P  V  H  G  E  T  W  V  A  M  I  E 2091        2101        2111        2121        2131        2141
TTCTCCACGCCGGTGCGGGCCTATGGCCTGATGAGCTACGGCAACTCTCGCCAGCCGGGC
  F  S  T  P  V  R  A  Y  G  L  M  S  Y  G  N  S  R  Q  P  G 2151        2161        2171        2181        2191        2201
ACGACGCACTACAGCGATCAGATCGAACGCGTGTCGCGCGCCGACTTCCGCGAACTGTTG
  T  T  H  Y  S  D  Q  I  E  R  V  S  R  A  D  F  R  E  L  L 2211        2221        2231        2241        2251        2261
CTGCGGCGAGAGCAGGTCGAGGCCGCCGTCCAGGAACGCACGCCCTTCAACTTCAAGCCA
  L  R  R  E  Q  V  E  A  A  V  Q  E  R  T  P  F  N  F  K  P

TGA
```

FIG. 13C

Alignment of Type-II acylases signal sequence

```
E.col  M KNRNRMIVN CVTASLMYYWSL PALA                                    26
K.cit  * *******GI ICCS S***                                    26
A.fae  *Q*GLV*    TGL*A*G*ILG*AGA*TH*                                   26
SE-83  *                                                                 1
SY-77  *LRVLH*AASALVMATVIGLAPAVAF***                                    29
```

α-subunit

```
                                                  ------D-----H--
E.col                                        EQSSSEIKIVRDEYGMPHIY       46
K.cit                                        ASPPT*V************       46
A.fae                                        QVQSVEVMSV**VF         44
SE-83        TMAAKTDREALQAALPPLSGSLSIPGL*APVRVQ**GW*I***K               45
SY-77        EPTST PQAPIAAYKP  RSNEIL          W*GV**               60

E.col  ANDTWHLFYGYGYVVAQDRLFQME MAR   RSTQGTVAEVLG   KDFVKFDKDIRRNY      99
K.cit  *DYR********** *       *****S**   *AS**Q    99
A.fae  *DSHYG*Y***A******D *  FVT*A*PGEQDAYY*MQV*Q*F   101
SE-83  *SGEADAYRAL*F*H********* LT*   *KAL*RAW    AEAAEA*ILV**LG    98
SY-77  GV*APSA*****W   **A*S HGDNIL*LYGEAR*KG**YW*    P*YEQTTVWLLT*G   113

E.col  WPDAIRAQIAALSPEDMSILQGYADGMNAWIDKVNTNPETLLPKQFNTFGFTPKRWEPFD    159
K.cit  *S**SAK**************AS*DK*QS**KH*****    159
A.fae  T*AS*QR******KDERD*FR*****Y**YLEQ*RRR** ****EYVD*D*Q*EPLTD**    160
SE-83  MEKVC*RDFE**GA*AKDM*RA*VA*V**FL  ASGA*   **IEYGLL*AE*EP***WH    153
SY-77  V*ERAQQWY*QQ**DFRAN*DAF*A*IY    AQQD    DISPEVRQVL*VSGADVV  167

-----S-----
E.col  VAMIFVGTMANRFSDSTSEIDNLAL       LTALKDKYGVSQGMAVFNQLKWLVNPSAPT   214
K.cit  *************************       *V****DE***************   214
A.fae  *VWS*******TNL*VTA**M       RQS*EKQH*PER*R*L*DE*L*INDTT***   215
SE-83  SIAVMRRLGLLMG*VWFKLWRM***PVVGAAN***LR*DDGGQ     D*LCIPPGVEAE    208
SY-77  AHAHRLMNFLYVA*PGRTLGEGDPPDLADQG                                  198

E.col  TIAVQ        ESNYPLKFNQQNSQTA                                   235
K.cit  *AR        S***DLT***                                   235
A.fae  *VPAP        AAEHK* QA*AGT*DLA                                  236
SE-83  RLEADLAALRPAVDAL**AMGGDASD*AGGG                                  239
SY-77                                                                  198
``` connecting peptide

```
E.col  ALL PRYDLPAPMLDRPAK  GADGALLALTAGKNRETIVAQFAQGGANGLAGYPTT        289
K.cit  *VQ*******   *T****VI****A N********        289
A.fae      HVSSPV* ATE*E*QD*HW*GR*PDF*PK*                              265
SE-83                                                                  239
SY-77                                                                  198
```

FIG. 14A

ß-subunit
```
------S---------------------------------------------------------------
E.col  SNMWVIGKSKAQDAKAIMVNGPQFGWYAPAYTYGIG LHGAGYDVTGNTPFAYPGLGFGH 348
K.cit  ********N*****************A********  *******************V*** 348
A.fae  **L*STRPERV*EGSTVLI********N*******  ************IVL**T      324
SE-83  **N*AVAPGRTATGRP*LAGD*H RVFEIPGM*AQHH*ACDRF*MI*L*VPGV**FPHFA 298
SY-77  **S*AVAPG*TANGN*LLLQN*HLS*TTDYF**YEAH*VTPDFEIY*A*QIGL* VIRFA 257

E.col  NGVISWGSTAGFGDDVDIFAERLSAE KPGYYLHNG KWV KMLSREETITVKNGQAE 403
K.cit  ****************K    Q*  E *K*ADP* 403
A.fae  *SE*AA*PQ*V***YQ*K*NPS RADQ*WF*N A*R T*EQ*K*R*Q*RGQADR 379
SE-83  H**KVAYCV*HA*M*IH*LYL* QF**DGRTARFG *E  FE PVAW*RDR*A*RG*ADR 353
SY-77  F*QRMGITN*VNGMVGATNY  **TLQDGGYL*DG QVRPFERRQA*YRLRQADGTTVDK 314

E.col  TFTVWRT VHGNILQTDQTTQTAYAKSRAWDGKE VASLLAWTHQMKA  KNWQEWTQQA 459
K.cit  *****  LDVIKTR**A*A* A********  *P****** 459
A.fae  EM*IW** ***PVM*F*YDQGA**S*K*S***Y* *Q****LNVA**  R**T*FLD** 435
SE-83  E DIVE* R**PVIAG* PLEG*ALTL*SVQFA*THL*FDCLTRMPG*S TVA*LYDATR 409
SY-77  PLEI *SS***PVFER  ADG**V* V*VA *LD RPGM*EQYFD*ITADSFDDYEAAL* 368

------------------D-------------------------
E.col  AKQALTINWYYADVNGNIGYVHTGAYPDRQSGHDPRLP  VPG TGKWDKGLLPFEMNP 516
K.cit  *********************P******  **  D********S*DL** 515
A.fae  S*M*IS******KH******SPAFL*Q*PADQ*I*V*  AK* D*SME*L*IKS*DAI* 492
SE-83  GWGLIDH*LVAG**A*S**HLVRARV*S* PRENGW  *WS*EHE*R*WI*H*AM* 466
SY-77  RM*VPTF*IV***RE*T*N*SFN*VA*K*AE*DIAFWQGL***DSSRYL*TETH*LDDL* 428

E.col  KVYNPQSGYIANWNNSPQKDYPASDLFAFLWGGADRVTEIDRLLEQKPRLTADQAWDVIR 576
K.cit  ****************************************TI*DKQF******* 575
A.fae  *AYPQLV****K*AP*KTNT*TYYWTY*  **MN*LVSQYQ**DLFSVQEI*EFNQ 550
SE-83  R*ID*PG*L*VTA**RVVA* DHP*YLCTDCHPPY*AER*MER*VAS*AFAV*H*AAIHA 525
SY-77  R*T**PG*FVQ*S*DP*TTPTWPVTYTPKD FPSYLAPQTPHS*RA  QQSVRLMSENDD 485

---------------------------------D-------------------
E.col  QT SRQDLNLRLFLPTLQAATSGLTQSDPRRQLVETLTRWDGINLLNDDGKTWQQPGSAI 635
K.cit  ** *LR **A KDAN*AEN******DK*AS*EV******Y**** 633
A.fae  KA *YS*V*W*Y*R*HLEKLAQQ*PAD*SSKAALTM*LA***MEQ  *Q*GQNAG*AR V 606
SE-83  D*L*PHVGL**AR*EAL    *IQG*L*AEE*RQIA*RMDAGSQAASAYNAFRRA 580
SY-77  L*LE*FMALQLSHR AV    MADRTL* DLIPAA*   I*PD EVQA AARLLAAWDRE 534

E.col  L NVWLTSML   KRTVVAAVP    MPFDKWYSASGYETTQDGPTGSLNISVGAKILYE 687
K.cit  *  *A****   *L***    AG*************************** 685
A.fae  *F KT**EE*Y  *QVLMPV**    ESHRAM**QT*FA*Q*GPNP**I*L*M*T*V*LR 659
SE-83  *TRL*TAR*G*EQAIAHPF****PGVS*QGQVWW*VPTLLRN* DA*M*KGWSWDEA*S* 639
SY-77  FTSDSRA AL*FEEWARFL*   GQNFAGQAGF*TPTSL *K*VSTPYGVRDP*AAVD 587
```

FIG. 14B

```
------------------------------------------------------------------
E.col  AVQGDKSPIPQAVDLFAGKPQQEVVLAALEDTWETLSKRYGNNVSNWKTPAMALTFRANN  747
K.cit  *L*************G***E***I****D*A*Q********D*TG**************  745
A.fae  *LVLEAH*D*KR*NV*GERSSIMHTQNAQAR**QEQ*AQMAR*TM*TSVHR*SDKN  719
SE-83  *LSVATQNLTGRGWGEEHR*RFTHP*S*QFPA*AA*    L*P**  RPIGGDGD*VLA*  693
SY-77  QLRTAIANLTKRKYGAIDR*FGDASRMI*N*VNVPGAAG***LG*FRVFTTS D PDE*   644

-----------------------------------------------------------S------------
E.col  FFGVPQAAAEETRHQAEYQNRGTENDMIVFSPTTSDRPVLAWDVVAPGQSGFIAPDGTVD  807
K.cit  **********K*A*********************SGN******************KA*   805
A.fae  *T*T**TMPGN*FAFTG********NRV**DAKGVE   FC *AMP******TDNR*VRS  775
SE-83   GL**S*GP*       *T*    * ALSRY**DVGNW*  NSR* **FH*A**HP*     S  735
SY-77   GVRT*VHG *         TW     V AMIE   **T       **R*YGLMSY*N*RQPG     T  681

--------H--D-----------------------------------------------------
E.col  KHYEDQLKMYENFGRKSLWLTKQDVEA  HKESQEVLHVQR             846
K.cit  *D***S*******P*DE  ******Q*             844
A.fae  PEL**EC*TMDV*HA*IRR   NAQ*STM*LI*PQP             816
SE-83  PA  NAPWSDCAIVPM*YSW*RI*AEAVT*** * *PA             773
SY-77  TSIERVSRADFRE*L*RREQ*    AVRTPFNFKP             720
```

FIG. 14C

Amino acid residue selection in the A. faecalis α-subunit

|  | Number of Residues |
|---|---|
| selection 1: identical and similar (hydrophobic + charged + polar) | 169 (80%) |
| selection 2: identical and similar (selection 1 minus Asp, Glu, Arg, Lys) | 119 (57%) |
| selection 3: identical and similar (selection 2 minus conserved Gly and Pro) | 102 (49%) |
| selection 4: identical and similar hydrophobic residues | 74 (35%) |
| selection 5: identical hydrophobic residues | 44 (21%) |

The one-letter code preceding the numbers in the row represents the amino acids in the Alcaligenes faecalis Type-IIA acylase.

| | 1 | 2 | 3 | 4 | 5 | | 1 | 2 | 3 | 4 | 5 | | 1 | 2 | 3 | 4 | 5 |
|---|---|---|---|---|---|---|---|---|---|---|---|---|---|---|---|---|---|
| Q | 29 | 29 | 29 | | | Q | 61 | 61 | 61 | | | F | 101 | 101 | 101 | 101 | |
| S | 30 | | | | | D | 62 | | | | | P | 103 | 103 | | | |
| V | 31 | 31 | 31 | 31 | | R | 63 | | | | | S | 105 | 105 | 105 | | |
| E | 32 | | | | | L | 64 | 64 | 64 | 64 | 64 | I | 106 | 106 | 106 | 106 | 106 |
| V | 33 | 33 | 33 | 33 | | F | 65 | 65 | 65 | 65 | 65 | Q | 107 | | | | |
| M | 34 | 34 | 34 | 34 | | Q | 66 | 66 | 66 | | | Q | 109 | 109 | 109 | | |
| R | 35 | | | | | M | 67 | 67 | 67 | 67 | 67 | I | 110 | 110 | 110 | 110 | 110 |
| D | 36 | | | | | D | 68 | | | | | A | 111 | 111 | 111 | 111 | 111 |
| S | 37 | | | | | M | 69 | 69 | 69 | 69 | 69 | A | 112 | 112 | 112 | | |
| Y | 38 | 38 | 38 | 38 | 38 | A | 70 | 70 | 70 | 70 | 70 | L | 113 | 113 | 113 | 113 | 113 |
| G | 39 | 39 | | | | R | 71 | | | | | S | 114 | 114 | 114 | | |
| V | 40 | 40 | 40 | 40 | | R | 72 | | | | | D | 116 | | | | |
| P | 41 | 41 | | | | S | 73 | 73 | 73 | | | E | 117 | | | | |
| H | 42 | 42 | 42 | | | G | 76 | 76 | | | | D | 119 | | | | |
| V | 43 | 43 | 43 | 43 | | T | 77 | 77 | 77 | | | I | 120 | 120 | 120 | 120 | 120 |
| F | 44 | 44 | 44 | 44 | | V | 78 | | | | | R | 122 | | | | |
| A | 45 | 45 | 45 | 45 | 45 | A | 79 | 79 | 79 | | | G | 123 | 123 | | | |
| D | 46 | | | | | V | 81 | 81 | 81 | 81 | 81 | Y | 124 | 124 | 124 | 124 | 124 |
| S | 47 | | | | | L | 82 | 82 | 82 | 82 | 82 | A | 125 | 125 | 125 | 125 | 125 |
| H | 48 | 48 | 48 | | | G | 83 | 83 | | | | D | 126 | | | | |
| Y | 49 | 49 | 49 | 49 | | D | 88 | | | | | G | 127 | 127 | | | |
| L | 51 | 51 | 51 | 51 | 51 | Y | 90 | 90 | 90 | 90 | | N | 129 | 129 | 129 | | |
| Y | 52 | 52 | 52 | 52 | | V | 91 | 91 | 91 | 91 | 91 | A | 130 | 130 | 130 | 130 | 130 |
| Y | 53 | 53 | 53 | 53 | 53 | K | 92 | | | | | Y | 131 | 131 | 131 | 131 | |
| G | 54 | 54 | | | | Y | 93 | 93 | 93 | 93 | | L | 132 | 132 | 132 | 132 | |
| Y | 55 | 55 | 55 | 55 | 55 | D | 94 | | | | | E | 133 | | | | |
| G | 56 | 56 | | | | Q | 96 | | | | | Q | 134 | | | | |
| Y | 57 | 57 | 57 | 57 | 57 | V | 97 | 97 | 97 | 97 | | V | 135 | 135 | 135 | 135 | 135 |
| A | 58 | 58 | 58 | 58 | | R | 98 | | | | | R | 136 | | | | |
| V | 59 | 59 | 59 | 59 | 59 | Q | 99 | | | | | R | 138 | | | | |
| A | 60 | 60 | 60 | 60 | 60 | N | 100 | 100 | 100 | | | P | 139 | 139 | | | |

FIG. 15A

|   | 1 | 2 | 3 | 4 | 5 |
|---|---|---|---|---|---|
| E | 140 | | | | |
| L | 141 | 141 | 141 | 141 | 141 |
| L | 142 | 142 | 142 | 142 | 142 |
| P | 143 | 143 | | | |
| K | 144 | | | | |
| E | 145 | | | | |
| Y | 146 | 146 | 146 | 146 | |
| D | 148 | | | | |
| F | 149 | 149 | 149 | 149 | 149 |
| F | 151 | 151 | 151 | 151 | 151 |
| Q | 152 | | | | |
| P | 153 | 153 | | | |
| E | 154 | | | | |
| L | 156 | 156 | 156 | 156 | |
| T | 157 | | | | |
| F | 159 | 159 | 159 | 159 | 159 |
| D | 160 | | | | |
| V | 161 | 161 | 161 | 161 | 161 |
| V | 162 | 162 | 162 | 162 | |
| M | 163 | 163 | 163 | 163 | 163 |
| I | 164 | 164 | 164 | 164 | 164 |
| W | 165 | 165 | 165 | 165 | |
| V | 166 | 166 | 166 | 166 | 166 |
| G | 167 | 167 | | | |
| S | 168 | 168 | 168 | | |

|   | 1 | 2 | 3 | 4 | 5 |
|---|---|---|---|---|---|
| M | 169 | 169 | 169 | 169 | 169 |
| A | 170 | 170 | 170 | 170 | 170 |
| N | 171 | 171 | 171 | | |
| R | 172 | | | | |
| F | 173 | 173 | 173 | 173 | 173 |
| S | 174 | 174 | 174 | | |
| D | 175 | | | | |
| T | 176 | 176 | 176 | | |
| N | 177 | 177 | 177 | | |
| E | 179 | | | | |
| V | 180 | 180 | 180 | 180 | |
| T | 181 | | | | |
| L | 183 | 183 | 183 | 183 | 183 |
| A | 184 | 184 | 184 | 184 | 184 |
| M | 185 | 185 | 185 | 185 | |
| Q | 187 | 187 | 187 | | |
| S | 188 | 188 | 188 | | |
| L | 189 | 189 | 189 | 189 | |
| E | 190 | | | | |
| K | 191 | | | | |
| Q | 192 | | | | |
| G | 194 | 194 | | | |
| E | 196 | | | | |
| R | 197 | | | | |
| G | 198 | 198 | | | |

|   | 1 | 2 | 3 | 4 | 5 |
|---|---|---|---|---|---|
| A | 200 | 200 | 200 | 200 | 200 |
| L | 201 | 201 | 201 | 201 | |
| F | 202 | 202 | 202 | 202 | 202 |
| D | 203 | | | | |
| E | 204 | | | | |
| L | 205 | 205 | 205 | 205 | 205 |
| W | 207 | 207 | 207 | 207 | 207 |
| I | 208 | 208 | 208 | 208 | |
| D | 210 | | | | |
| T | 211 | 211 | 211 | | |
| T | 212 | 212 | 212 | | |
| A | 213 | 213 | 213 | 213 | 213 |
| P | 214 | 214 | | | |
| T | 215 | 215 | 215 | | |
| T | 216 | 216 | 216 | | |
| V | 217 | 217 | 217 | 217 | |
| P | 218 | 218 | 218 | 218 | |
| A | 219 | 219 | 219 | 219 | |
| E | 223 | | | | |
| H | 224 | 224 | 224 | | |
| P | 226 | 226 | | | |
| T | 232 | 232 | 232 | | |
| Q | 233 | 233 | 233 | | |
| D | 234 | | | | |
| L | 235 | 235 | 235 | 235 | |

FIG. 15B

Amino acid residue selection in the A. faecalis ß-subunit

Number of Residues selection 1: identical and similar
(hydrophobic + charged + polar)                416 (75%)
selection 2: identical and similar
(selection 1 minus Asp, Glu, Arg, Lys)         304 (55%)
selection 3: identical and similar
(selection 2 minus conserved Gly and Pro)      258 (47%)
selection 4: identical and similar hydrophobic
residues                                       162 (29%)
selection 5: identical hydrophobic residues     81 (15%)

The one-letter code preceding the numbers in the row represents the amino acids in the _Alcaligenes faecalis_ Type-IIA acylase.

| | 1 | 2 | 3 | 4 | 5 | | 1 | 2 | 3 | 4 | 5 | | 1 | 2 | 3 | 4 | 5 |
|---|---|---|---|---|---|---|---|---|---|---|---|---|---|---|---|---|---|
| S | 266 | 266 | 266 | | | G | 306 | 306 | | | | L | 347 | 347 | 347 | 347 | 347 |
| N | 267 | 267 | 267 | | | F | 307 | 307 | 307 | 307 | | N | 348 | 348 | 348 | | |
| L | 268 | 268 | 268 | 268 | | D | 308 | | | | | P | 349 | 349 | 349 | 349 | |
| W | 269 | 269 | 269 | 269 | 269 | V | 309 | 309 | 309 | 309 | 309 | S | 350 | | | | |
| E | 274 | | | | | V | 310 | 310 | 310 | | | R | 351 | | | | |
| R | 275 | | | | | G | 311 | 311 | | | | A | 352 | 352 | 352 | 352 | |
| V | 276 | 276 | 276 | 276 | | N | 312 | 312 | 312 | | | Y | 355 | 355 | 355 | 355 | 355 |
| Q | 277 | 277 | 277 | | | T | 313 | 313 | 313 | | | N | 358 | 358 | 358 | | |
| E | 278 | | | | | P | 314 | 314 | | | | W | 361 | 361 | 361 | 361 | 361 |
| G | 279 | 279 | 279 | 279 | | F | 315 | 315 | 315 | 315 | 315 | T | 363 | | | | |
| S | 280 | | | | | A | 316 | 316 | 316 | 316 | 316 | M | 364 | 364 | 364 | 364 | 364 |
| T | 281 | 281 | 281 | | | Y | 317 | 317 | 317 | 317 | 317 | Q | 366 | 366 | 366 | | |
| V | 282 | 282 | 282 | 282 | | P | 318 | 318 | | | | R | 367 | | | | |
| L | 283 | 283 | 283 | 283 | | V | 320 | 320 | 320 | 320 | | K | 368 | | | | |
| I | 284 | 284 | 284 | 284 | | F | 322 | 322 | 322 | 322 | 322 | E | 369 | | | | |
| N | 285 | 285 | 285 | | | G | 323 | 323 | | | | R | 370 | | | | |
| G | 286 | 286 | | | | T | 324 | 324 | 324 | | | I | 371 | 371 | 371 | 371 | 371 |
| P | 287 | 287 | | | | N | 325 | 325 | 325 | | | V | 373 | 373 | 373 | 373 | 373 |
| Q | 288 | 288 | 288 | | | S | 326 | 326 | 326 | | | R | 374 | | | | |
| F | 289 | 289 | 289 | 289 | 289 | I | 328 | 328 | 328 | 328 | 328 | R | 379 | | | | |
| G | 290 | 290 | | | | A | 329 | 329 | 329 | | | E | 380 | | | | |
| W | 291 | 291 | 291 | 291 | 291 | W | 330 | 330 | 330 | 330 | 330 | M | 381 | 381 | 381 | 381 | |
| P | 294 | 294 | | | | G | 331 | 331 | | | | T | 382 | 382 | 382 | | |
| A | 295 | 295 | 295 | 295 | 295 | A | 332 | 332 | 332 | | | I | 383 | 383 | 383 | 383 | |
| Y | 296 | 296 | 296 | 296 | 296 | T | 333 | 333 | 333 | | | W | 384 | 384 | 384 | 384 | 384 |
| T | 297 | 297 | 297 | | | A | 334 | 334 | 334 | 334 | 334 | R | 385 | | | | |
| Y | 298 | 298 | 298 | 298 | 298 | G | 335 | 335 | | | | T | 386 | 386 | 386 | | |
| G | 299 | 299 | | | | D | 338 | | | | | V | 387 | 387 | 387 | 387 | |
| I | 300 | 300 | 300 | 300 | 300 | V | 340 | 340 | 340 | 340 | 340 | H | 388 | | | | |
| G | 301 | 301 | | | | D | 341 | | | | | G | 389 | 389 | | | |
| L | 302 | 302 | 302 | 302 | 302 | I | 342 | 342 | 342 | 342 | 342 | V | 391 | 391 | 391 | 391 | |
| H | 303 | 303 | 303 | | | Y | 343 | 343 | 343 | 343 | | M | 392 | 392 | 392 | 392 | |
| G | 304 | 304 | | | | E | 345 | | | | | Q | 393 | | | | |
| A | 305 | 305 | 305 | 305 | 305 | K | 346 | | | | | D | 395 | | | | |

FIG. 16A

| | 1 | 2 | 3 | 4 | 5 | | 1 | 2 | 3 | 4 | 5 | | 1 | 2 | 3 | 4 | 5 |
|---|---|---|---|---|---|---|---|---|---|---|---|---|---|---|---|---|---|
| D | 397 | | | | | V | 456 | 456 | 456 | 456 | 456 | Y | 523 | 523 | 523 | 523 | |
| Q | 398 | 398 | 398 | | | S | 457 | 457 | 457 | | | G | 524 | 524 | | | |
| A | 400 | 400 | 400 | | | P | 458 | 458 | 458 | | | D | 525 | | | | |
| A | 401 | 401 | 401 | 401 | 401 | A | 459 | 459 | 459 | 459 | | R | 526 | | | | |
| Y | 402 | 402 | 402 | 402 | 402 | P | 462 | 462 | | | | M | 527 | 527 | 527 | 527 | |
| S | 403 | 403 | 403 | | | Q | 463 | | | | | N | 528 | 528 | 528 | | |
| K | 404 | | | | | R | 464 | | | | | E | 529 | | | | |
| R | 406 | | | | | A | 466 | 466 | 466 | | | L | 530 | 530 | 530 | 530 | |
| S | 407 | 407 | 407 | | | Q | 468 | 468 | 468 | | | S | 532 | | | | |
| W | 408 | 408 | 408 | 408 | 408 | D | 469 | | | | | Q | 535 | | | | |
| G | 410 | 410 | | | | R | 471 | | | | | Q | 536 | | | | |
| E | 412 | | | | | V | 472 | 472 | 472 | 472 | | K | 537 | | | | |
| V | 413 | 413 | 413 | 413 | 413 | P | 473 | 473 | | | | S | 541 | 541 | 541 | | |
| S | 415 | 415 | 415 | | | A | 474 | 474 | 474 | 474 | | V | 542 | 542 | 542 | 542 | |
| L | 416 | 416 | 416 | 416 | 416 | D | 477 | | | | | Q | 543 | | | | |
| L | 417 | 417 | 417 | 417 | 417 | G | 478 | 478 | | | | E | 544 | | | | |
| A | 418 | 418 | 418 | 418 | 418 | S | 479 | | | | | I | 545 | 545 | 545 | 545 | |
| W | 419 | 419 | 419 | 419 | 419 | E | 481 | | | | | W | 546 | 546 | 546 | 546 | 546 |
| N | 421 | 421 | 421 | | | W | 482 | 482 | 482 | 482 | 482 | E | 547 | | | | |
| A | 423 | 423 | 423 | 423 | | G | 484 | 484 | | | | Q | 550 | | | | |
| K | 424 | | | | | I | 485 | 485 | 485 | 485 | | K | 551 | | | | |
| A | 425 | 425 | 425 | 425 | 425 | S | 487 | 487 | 487 | | | A | 552 | 552 | 552 | | |
| R | 426 | | | | | F | 488 | 488 | 488 | 488 | 488 | S | 553 | 553 | 553 | | |
| N | 427 | 427 | 427 | | | D | 489 | | | | | D | 556 | | | | |
| W | 428 | 428 | 428 | 428 | 428 | A | 490 | 490 | 490 | 490 | | V | 557 | 557 | 557 | 557 | |
| T | 429 | 429 | 429 | | | P | 492 | 492 | | | | R | 560 | | | | |
| F | 431 | 431 | 431 | 431 | | K | 493 | | | | | F | 562 | 562 | 562 | 562 | |
| D | 433 | | | | | A | 494 | 494 | 494 | 494 | | P | 564 | 564 | | | |
| Q | 434 | 434 | 434 | | | Y | 495 | 495 | 495 | 495 | 495 | H | 565 | 565 | 565 | | |
| A | 435 | 435 | 435 | 435 | 435 | N | 496 | 496 | 496 | | | E | 567 | | | | |
| S | 436 | 436 | 436 | | | P | 497 | 497 | | | | L | 569 | 569 | 569 | 569 | |
| K | 437 | | | | | Q | 499 | 499 | 499 | | | A | 570 | 570 | 570 | | |
| A | 439 | 439 | 439 | 439 | 439 | G | 500 | 500 | | | | L | 573 | 573 | 573 | 573 | 573 |
| I | 440 | 440 | 440 | 440 | | Y | 501 | 501 | 501 | 501 | 501 | P | 574 | 574 | 574 | | |
| S | 441 | 441 | 441 | | | L | 502 | 502 | 502 | 502 | | D | 576 | | | | |
| I | 442 | 442 | 442 | 442 | 442 | V | 503 | 503 | 503 | 503 | | D | 577 | | | | |
| N | 443 | 443 | 443 | | | N | 504 | 504 | 504 | | | S | 578 | 578 | 578 | | |
| W | 444 | 444 | 444 | 444 | 444 | W | 505 | 505 | 505 | 505 | 505 | S | 579 | | | | |
| Y | 445 | 445 | 445 | 445 | 445 | N | 506 | 506 | 506 | | | K | 580 | | | | |
| Y | 446 | 446 | 446 | 446 | 446 | N | 507 | 507 | 507 | | | A | 582 | 582 | 582 | 582 | |
| A | 447 | 447 | 447 | 447 | 447 | K | 508 | | | | | L | 583 | 583 | 583 | 583 | |
| D | 448 | | | | | P | 509 | 509 | | | | T | 584 | | | | |
| H | 450 | 450 | 450 | | | D | 512 | | | | | L | 586 | 586 | 586 | 586 | 586 |
| G | 451 | 451 | | | | T | 514 | 514 | 514 | | | W | 589 | 589 | 589 | 589 | 589 |
| N | 452 | 452 | 452 | | | T | 516 | 516 | 516 | | | D | 590 | | | | |
| I | 453 | 453 | 453 | 453 | 453 | D | 517 | | | | | G | 591 | 591 | | | |
| G | 454 | 454 | | | | Y | 519 | 519 | 519 | 519 | | E | 593 | | | | |
| Y | 455 | 455 | 455 | 455 | 455 | W | 521 | 521 | 521 | 521 | | D | 595 | | | | |

FIG. 16B

| | 1 | 2 | 3 | 4 | 5 |
|---|---|---|---|---|---|
| Q | 596 | | | | |
| G | 597 | 597 | | | |
| Q | 599 | 599 | 599 | | |
| P | 603 | 603 | | | |
| A | 604 | 604 | 604 | 604 | |
| R | 605 | | | | |
| V | 606 | 606 | 606 | 606 | |
| L | 607 | 607 | 607 | 607 | 607 |
| K | 609 | | | | |
| W | 611 | 611 | 611 | 611 | 611 |
| L | 612 | 612 | 612 | 612 | 612 |
| E | 613 | | | | |
| E | 614 | | | | |
| M | 615 | 615 | 615 | 615 | 615 |
| K | 617 | | | | |
| Q | 618 | | | | |
| V | 619 | | | | |
| L | 620 | 620 | 620 | 620 | |
| M | 621 | 621 | 621 | 621 | |
| P | 622 | 622 | 622 | 622 | |
| V | 623 | 623 | 623 | 623 | |
| V | 624 | 624 | 624 | 624 | 624 |
| P | 625 | 625 | | | |
| S | 627 | 627 | 627 | | |
| Y | 632 | 632 | 632 | 632 | 632 |
| S | 633 | 633 | 633 | | |
| T | 635 | 635 | 635 | | |
| G | 636 | 636 | | | |
| F | 637 | 637 | 637 | 637 | |
| T | 639 | 639 | 639 | | |
| Q | 640 | 640 | 640 | | |
| Q | 641 | 641 | 641 | | |
| G | 642 | | | | |
| P | 643 | 643 | 643 | 643 | |
| P | 645 | 645 | 645 | | |
| G | 646 | 646 | | | |
| S | 647 | 647 | 647 | | |
| I | 648 | 648 | 648 | 648 | |
| N | 649 | 649 | 649 | | |
| L | 650 | 650 | 650 | 650 | |
| S | 651 | 651 | 651 | | |
| M | 652 | 652 | 652 | 652 | |
| G | 653 | 653 | | | |
| K | 655 | | | | |
| V | 656 | 656 | 656 | 656 | |
| L | 657 | 657 | 657 | 657 | 657 |
| R | 659 | | | | |
| A | 660 | 660 | 660 | 660 | 660 |
| L | 661 | 661 | 661 | 661 | |
| E | 664 | | | | |

| | 1 | 2 | 3 | 4 | 5 |
|---|---|---|---|---|---|
| H | 666 | 666 | 666 | | |
| P | 667 | 667 | | | |
| P | 669 | 669 | | | |
| K | 670 | | | | |
| V | 672 | 672 | 672 | 672 | 672 |
| N | 673 | | | | |
| V | 674 | 674 | 674 | 674 | |
| F | 675 | 675 | 675 | 675 | 675 |
| G | 676 | 676 | 676 | 676 | |
| R | 678 | | | | |
| S | 679 | 679 | 679 | | |
| S | 680 | | | | |
| Q | 681 | 681 | 681 | | |
| E | 682 | | | | |
| I | 683 | 683 | 683 | 683 | |
| M | 684 | 684 | 684 | 684 | |
| T | 686 | 686 | 686 | | |
| A | 687 | 687 | 687 | 687 | 687 |
| L | 688 | 688 | 688 | 688 | 688 |
| Q | 689 | | | | |
| N | 690 | | | | |
| A | 691 | 691 | 691 | | |
| R | 694 | | | | |
| L | 695 | 695 | 695 | 695 | 695 |
| S | 696 | 696 | 696 | | |
| Q | 697 | | | | |
| E | 698 | | | | |
| G | 700 | 700 | | | |
| Q | 702 | | | | |
| M | 703 | 703 | 703 | 703 | |
| A | 704 | 704 | 704 | | |
| W | 706 | 706 | 706 | 706 | 706 |
| P | 709 | 709 | | | |
| T | 710 | 710 | 710 | | |
| V | 712 | 712 | 712 | 712 | |
| R | 714 | | | | |
| F | 715 | 715 | 715 | 715 | 715 |
| S | 716 | | | | |
| K | 718 | | | | |
| N | 719 | 719 | 719 | | |
| F | 720 | 720 | 720 | 720 | 720 |
| G | 722 | 722 | | | |
| T | 723 | | | | |
| P | 724 | 724 | | | |
| Q | 725 | 725 | 725 | | |
| T | 726 | 726 | 726 | | |
| P | 728 | 728 | 728 | 728 | |
| H | 730 | | | | |
| T | 731 | 731 | 731 | | |
| T | 735 | 735 | 735 | | |

| | 1 | 2 | 3 | 4 | 5 |
|---|---|---|---|---|---|
| Y | 737 | 737 | 737 | 737 | 737 |
| Q | 738 | 738 | 738 | | |
| N | 739 | 739 | 739 | | |
| R | 740 | | | | |
| G | 741 | 741 | | | |
| T | 742 | 742 | 742 | | |
| E | 743 | | | | |
| N | 744 | 744 | 744 | | |
| N | 745 | | | | |
| V | 747 | 747 | 747 | 747 | |
| V | 748 | 748 | 748 | 748 | 748 |
| F | 749 | 749 | 749 | 749 | 749 |
| D | 750 | | | | |
| A | 751 | 751 | 751 | 751 | |
| G | 753 | 753 | 753 | | |
| V | 754 | | | | |
| E | 755 | | | | |
| C | 757 | 757 | 757 | 757 | |
| D | 758 | | | | |
| A | 759 | 759 | 759 | 759 | |
| M | 760 | 760 | 760 | 760 | |
| P | 761 | 761 | 761 | 761 | |
| P | 762 | 762 | | | |
| G | 763 | 763 | | | |
| Q | 764 | 764 | 764 | | |
| S | 765 | 765 | 765 | | |
| G | 766 | 766 | | | |
| F | 767 | 767 | 767 | 767 | 767 |
| R | 771 | | | | |
| G | 772 | 772 | | | |
| H | 777 | 777 | 777 | | |
| Y | 778 | 778 | 778 | 778 | 778 |
| E | 779 | | | | |
| D | 780 | | | | |
| Q | 781 | 781 | 781 | | |
| L | 782 | 782 | 782 | 782 | 782 |
| K | 783 | | | | |
| L | 784 | 784 | 784 | 784 | 784 |
| Y | 785 | 785 | 785 | 785 | 785 |
| E | 786 | | | | |
| N | 787 | 787 | 787 | | |
| F | 788 | 788 | 788 | 788 | 788 |
| K | 791 | | | | |
| T | 792 | 792 | 792 | | |
| M | 793 | 793 | 793 | 793 | |
| V | 795 | 795 | 795 | 795 | |
| T | 796 | 796 | 796 | | |
| D | 799 | | | | |
| I | 800 | 800 | 800 | 800 | |
| R | 801 | | | | |

FIG. 16C

|   | 1 | 2 | 3 | 4 | 5 |
|---|---|---|---|---|---|
| N | 803 | 803 | 803 | | |
| Q | 805 | | | | |
| S | 806 | 806 | 806 | | |
| S | 807 | 807 | 807 | | |
| T | 808 | | | | |
| M | 809 | 809 | 809 | 809 | |
| L | 810 | 810 | 810 | 810 | 810 |
| I | 812 | 812 | 812 | 812 | |
| Q | 813 | 813 | 813 | | |

FIG. 16D

Amino acid residue selection in the SY-77 α-subunit

| | Number of Residues |
|---|---|
| selection 1: identical and similar | 108 (64%) |

(hydrophobic + charged +polar)

selection 2: identical and similar        87 (51%)

(selection 1 minus positions which can accomodate a charged residue such as Arg, Lys, His, Glu and Asp in both Type-IIA and Type-IIB acylases. Only when Type-IIA acylases show Asp or Glu and Type-IIB acylases show Arg, Lys or His, the position is maintained).

selection 3: identical and similar        76 (45%)

(selection 2 minus conserved Gly and Pro)

selection 4: identical and similar        23 (14%)

(selection 3 minus identical and similar hydrophobic residues)

selection 5: identical and similar        9 ( 5%)

(selection 4 without positions that can accomodate a polar residue in both Type-IIA and Type-IIB acylases)

selection 6: positions in Type-IIB acylase which show residues that unlike residues at the similar position in Type-IIA acylases may accomodate the negatively charged glutaryl side chain.        3 ( 2%)

The one-letter code preceding the numbers in the row represents the amino acids in the SY-77 Type-IIB acylase.

FIG. 17A

|   | 1 | 2 | 3 | 4 | 5 | 6 |   | 1 | 2 | 3 | 4 | 5 | 6 |   | 1 | 2 | 3 | 4 | 5 | 6 |
|---|---|---|---|---|---|---|---|---|---|---|---|---|---|---|---|---|---|---|---|---|
| P | 31 | 31 | 31 |  |  |  | Y | 97 | 97 | 97 |  |  |  | V | 166 | 166 | 166 |  |  |  |
| T | 32 | 32 | 32 | 32 | 32 |  | W | 98 | 98 | 98 |  |  |  | A | 168 | 168 | 168 | 168 |  |  |
| S | 33 | 33 | 33 | 33 | 33 |  | G | 99 | 99 |  |  |  |  | A | 170 | 170 | 170 |  |  |  |
| T | 34 | 34 | 34 | 34 | 34 |  | P | 100 | 100 | 100 |  |  |  | L | 177 | 177 | 177 |  |  |  |
| Q | 36 |  |  |  |  |  | D | 101 |  |  |  |  |  | Y | 178 | 178 | 178 |  |  |  |
| A | 37 | 37 | 37 |  |  |  | Y | 102 | 102 | 102 |  |  |  | V | 179 | 179 | 179 |  |  |  |
| A | 40 | 40 | 40 |  |  |  | Q | 104 |  |  |  |  |  | A | 180 | 180 | 180 |  |  |  |
| A | 41 | 41 | 41 |  |  |  | T | 105 | 105 | 105 | 105 | 105 |  | S | 181 | 181 | 181 | 181 |  |  |
| Y | 42 | 42 | 42 |  |  |  | T | 106 |  |  |  |  |  | P | 182 | 182 | 182 |  |  |  |
| P | 44 | 44 |  |  |  |  | V | 107 |  |  |  |  |  | T | 185 | 185 | 185 | 185 |  |  |
| S | 46 | 46 | 46 | 46 | 46 |  | W | 108 | 108 | 108 |  |  |  | L | 186 | 186 | 186 | 186 | 186 |  |
| E | 48 | 48 | 48 | 48 |  |  | L | 109 | 109 | 109 |  |  |  | E | 188 |  |  |  |  |  |
| I | 49 | 49 | 49 |  |  |  | T | 111 |  |  |  |  |  | P | 191 | 191 | 191 |  |  |  |
| D | 52 |  |  |  |  |  | G | 113 | 113 |  |  |  |  | L | 194 | 194 | 194 |  |  |  |
| G | 53 | 53 |  |  |  |  | V | 114 | 114 | 114 |  |  |  | A | 195 | 195 | 195 |  |  |  |
| Y | 54 | 54 | 54 |  |  |  | E | 116 |  |  |  |  |  | G | 198 | 198 | 198 |  |  |  |
| G | 55 | 55 |  |  |  |  | A | 118 | 118 | 118 |  |  |  |  |  |  |  |  |  |  |
| V | 56 | 56 | 56 |  |  |  | Q | 119 | 119 | 119 | 119 |  |  |  |  |  |  |  |  |  |
| P | 57 | 57 |  |  |  |  | Q | 120 |  |  |  |  |  |  |  |  |  |  |  |  |
| H | 58 |  |  |  |  |  | Y | 122 | 122 | 122 |  |  |  |  |  |  |  |  |  |  |
| I | 59 | 59 | 59 |  |  |  | S | 126 | 126 | 126 | 126 |  |  |  |  |  |  |  |  |  |
| G | 61 | 61 | 61 |  |  |  | P | 127 | 127 | 127 |  |  |  |  |  |  |  |  |  |  |
| V | 62 | 62 | 62 | 62 |  |  | D | 128 |  |  |  |  |  |  |  |  |  |  |  |  |
| P | 65 | 65 | 65 |  |  |  | F | 129 | 129 | 129 | 129 | 129 | 129 |  |  |  |  |  |  |  |
| S | 66 |  |  |  |  |  | R | 130 |  |  |  |  |  |  |  |  |  |  |  |  |
| A | 67 | 67 | 67 |  |  |  | L | 133 | 133 | 133 |  |  |  |  |  |  |  |  |  |  |
| F | 68 | 68 | 68 |  |  |  | D | 134 |  |  |  |  |  |  |  |  |  |  |  |  |
| Y | 69 | 69 | 69 | 69 |  |  | A | 135 | 135 | 135 |  |  |  |  |  |  |  |  |  |  |
| G | 70 | 70 | 70 |  |  |  | F | 136 | 136 | 136 |  |  |  |  |  |  |  |  |  |  |
| Y | 71 | 71 | 71 |  |  |  | A | 137 | 137 | 137 |  |  |  |  |  |  |  |  |  |  |
| G | 72 | 72 |  |  |  |  | A | 138 | 138 | 138 | 138 | 138 | 138 |  |  |  |  |  |  |  |
| W | 73 | 73 | 73 |  |  |  | G | 139 | 139 |  |  |  |  |  |  |  |  |  |  |  |
| A | 74 | 74 | 74 |  |  |  | I | 140 | 140 | 140 |  |  |  |  |  |  |  |  |  |  |
| Q | 75 | 75 | 75 | 75 |  |  | N | 141 | 141 | 141 | 141 |  |  |  |  |  |  |  |  |  |
| R | 77 |  |  |  |  |  | A | 142 | 142 | 142 |  |  |  |  |  |  |  |  |  |  |
| H | 79 | 79 | 79 | 79 |  |  | Y | 143 | 143 | 143 |  |  |  |  |  |  |  |  |  |  |
| D | 81 |  |  |  |  |  | A | 144 | 144 | 144 |  |  |  |  |  |  |  |  |  |  |
| I | 83 | 83 | 83 |  |  |  | Q | 145 | 145 | 145 | 145 |  |  |  |  |  |  |  |  |  |
| R | 85 |  |  |  |  |  | Q | 146 | 146 | 146 | 146 |  |  |  |  |  |  |  |  |  |
| E | 89 |  |  |  |  |  | P | 148 | 148 |  |  |  |  |  |  |  |  |  |  |  |
| A | 90 | 90 | 90 |  |  |  | I | 151 | 151 | 151 |  |  |  |  |  |  |  |  |  |  |
| G | 92 | 92 |  |  |  |  | S | 152 |  |  |  |  |  |  |  |  |  |  |  |  |
| K | 93 | 93 | 93 | 93 | 93 | 93 | V | 155 | 155 | 155 |  |  |  |  |  |  |  |  |  |  |
| G | 94 | 94 | 94 |  |  |  | V | 158 | 158 | 158 |  |  |  |  |  |  |  |  |  |  |
| A | 95 | 95 | 95 |  |  |  | P | 160 | 160 |  |  |  |  |  |  |  |  |  |  |  |
| E | 96 |  |  |  |  |  | S | 162 | 162 | 162 | 162 |  |  |  |  |  |  |  |  |  |

FIG. 17B

Amino acid residue selection in the SY-77 β-subunit

|  | Number of Residues |
|---|---|
| selection 1: identical and similar | 323 (62%) |

(hydrophobic + charged +polar)

selection 2: identical and similar      258 (50%)

(selection 1 minus positions which can accomodate a charged residue such as Arg, Lys, His, Glu and Asp in both Type-IIA and Type-IIB acylases. Only when Type-IIA acylases show Asp or Glu and Type-IIB acylases show Arg, Lys or His, the position is maintained.)

selection 3: identical and similar      225 (43%)

(selection 2 minus conserved Gly and Pro)

selection 4: identical and similar      80 (15%)

(selection 3 minus identical and similar hydrophobic residues)

selection 5: identical and similar      35 ( 7%)

(selection 4 without positions that can accomodate a polar residue in both Type-IIA and Type-IIB acylases)

selection 6: positions in Type-IIB acylase which show residues that unlike residues at the similar position in Type-IIA acylases may accomodate the negatively charged glutaryl side chain.      9 ( 4%)

The one-letter code preceding the numbers in the row represents the amino acids in the SY-77 Type-IIB acylase.

FIG. 17C

|   | 1 | 2 | 3 | 4 | 5 | 6 |
|---|---|---|---|---|---|---|
| S | 199 | 199 | 199 | 199 |     |     |
| N | 200 | 200 | 200 | 200 |     |     |
| S | 201 | 201 | 201 | 201 | 201 |     |
| W | 202 | 202 | 202 |     |     |     |
| A | 203 | 203 | 203 |     |     |     |
| V | 204 | 204 | 204 |     |     |     |
| A | 205 | 205 | 205 |     |     |     |
| P | 206 | 206 |     |     |     |     |
| G | 207 | 207 |     |     |     |     |
| K | 208 |     |     |     |     |     |
| T | 209 | 209 | 209 | 209 | 209 |     |
| A | 210 | 210 | 210 |     |     |     |
| N | 211 | 211 | 211 | 211 | 211 | 211 |
| G | 212 | 212 |     |     |     |     |
| N | 213 |     |     |     |     |     |
| A | 214 | 214 | 214 |     |     |     |
| L | 215 | 215 | 215 |     |     |     |
| L | 216 | 216 | 216 |     |     |     |
| L | 217 | 217 | 217 |     |     |     |
| N | 219 |     |     |     |     |     |
| P | 220 | 220 |     |     |     |     |
| H | 221 | 221 | 221 | 221 | 221 | 221 |
| S | 223 | 223 | 223 | 223 | 223 |     |
| W | 224 | 224 | 224 |     |     |     |
| T | 226 |     |     |     |     |     |
| U | 231 | 231 | 231 |     |     |     |
| Y | 232 | 232 | 232 |     |     |     |
| E | 233 |     |     |     |     |     |
| H | 235 | 235 | 235 | 235 | 235 | 235 |
| L | 236 | 236 | 236 |     |     |     |
| V | 237 | 237 | 237 |     |     |     |
| T | 238 | 238 | 238 |     |     |     |
| D | 240 |     |     |     |     |     |
| F | 241 | 241 | 241 |     |     |     |
| E | 242 |     |     |     |     |     |
| I | 243 | 243 | 243 |     |     |     |
| Y | 244 | 244 | 244 |     |     |     |
| G | 245 | 245 |     |     |     |     |
| H | 246 | 246 | 246 |     |     |     |
| T | 247 | 247 | 247 | 247 |     |     |
| G | 250 | 250 |     |     |     |     |
| L | 251 | 251 | 251 |     |     |     |
| P | 252 | 252 |     |     |     |     |
| V | 253 | 253 | 253 |     |     |     |
| R | 255 | 255 | 255 | 255 | 255 | 255 |
| F | 256 | 256 | 256 |     |     |     |

|   | 1 | 2 | 3 | 4 | 5 | 6 |
|---|---|---|---|---|---|---|
| A | 257 | 257 | 257 |     |     |     |
| N | 259 | 259 | 259 | 259 |     |     |
| R | 261 |     |     |     |     |     |
| M | 262 | 262 | 262 |     |     |     |
| G | 263 | 263 | 263 |     |     |     |
| I | 264 | 264 | 264 |     |     |     |
| T | 265 | 265 | 265 | 265 | 265 |     |
| T | 267 | 267 | 267 | 267 |     |     |
| M | 271 | 271 | 271 |     |     |     |
| T | 275 |     |     |     |     |     |
| Y | 277 | 277 | 277 |     |     |     |
| L | 281 | 281 | 281 |     |     |     |
| Q | 282 |     |     |     |     |     |
| D | 283 |     |     |     |     |     |
| G | 284 | 284 |     |     |     |     |
| L | 287 |     |     |     |     |     |
| G | 290 | 290 |     |     |     |     |
| Q | 291 | 291 | 291 | 291 |     |     |
| F | 295 | 295 | 295 |     |     |     |
| E | 296 |     |     |     |     |     |
| P | 298 | 298 |     |     |     |     |
| A | 300 | 300 | 300 |     |     |     |
| R | 303 |     |     |     |     |     |
| R | 305 |     |     |     |     |     |
| A | 307 | 307 | 307 |     |     |     |
| T | 310 | 310 | 310 | 310 |     |     |
| T | 311 | 311 | 311 | 311 |     |     |
| V | 312 | 312 | 312 |     |     |     |
| D | 313 |     |     |     |     |     |
| K | 314 |     |     |     |     |     |
| E | 317 |     |     |     |     |     |
| I | 318 | 318 | 318 |     |     |     |
| R | 319 |     |     |     |     |     |
| S | 320 | 320 | 320 | 320 |     |     |
| H | 323 |     |     |     |     |     |
| G | 324 | 324 |     |     |     |     |
| P | 325 | 325 |     |     |     |     |
| V | 326 | 326 | 326 |     |     |     |
| F | 327 | 327 | 327 |     |     |     |
| A | 330 | 330 | 330 |     |     |     |
| T | 333 | 333 | 333 | 333 |     |     |
| A | 334 | 334 | 334 |     |     |     |
| V | 335 | 335 | 335 |     |     |     |
| A | 336 | 336 | 336 |     |     |     |
| V | 337 | 337 | 337 |     |     |     |
| R | 338 |     |     |     |     |     |

|   | 1 | 2 | 3 | 4 | 5 | 6 |
|---|---|---|---|---|---|---|
| V | 339 | 339 | 339 | 339 |     |     |
| A | 340 | 340 | 340 |     |     |     |
| L | 342 |     |     |     |     |     |
| D | 343 |     |     |     |     |     |
| R | 344 | 344 | 344 | 344 | 344 | 344 |
| P | 179 | 179 | 179 |     |     |     |
| A | 345 | 345 | 345 |     |     |     |
| G | 346 | 346 | 346 | 346 |     |     |
| M | 347 | 347 | 347 |     |     |     |
| T | 356 | 356 | 356 | 356 | 356 |     |
| A | 357 | 357 | 357 | 357 | 357 |     |
| S | 359 | 359 | 359 | 359 |     |     |
| F | 360 | 360 | 360 |     |     |     |
| D | 362 |     |     |     |     |     |
| Y | 363 | 363 | 363 |     |     |     |
| A | 366 | 366 | 366 |     |     |     |
| M | 370 | 370 | 370 |     |     |     |
| V | 372 | 372 | 372 |     |     |     |
| P | 373 | 373 | 373 |     |     |     |
| T | 374 |     |     |     |     |     |
| N | 376 | 376 | 376 |     |     |     |
| I | 377 | 377 | 377 |     |     |     |
| V | 378 | 378 | 378 |     |     |     |
| Y | 379 | 379 | 379 |     |     |     |
| A | 380 | 380 | 380 |     |     |     |
| D | 381 |     |     |     |     |     |
| G | 384 | 384 |     |     |     |     |
| T | 385 | 385 | 385 | 385 |     |     |
| I | 386 | 386 | 386 |     |     |     |
| F | 390 | 390 | 390 |     |     |     |
| N | 391 | 391 | 391 |     |     |     |
| G | 392 | 392 | 392 |     |     |     |
| A | 394 | 394 | 394 |     |     |     |
| P | 395 | 395 |     |     |     |     |
| K | 396 |     |     |     |     |     |
| R | 397 |     |     |     |     |     |
| D | 401 |     |     |     |     |     |
| A | 403 | 403 | 403 |     |     |     |
| F | 404 | 404 | 404 |     |     |     |
| W | 405 | 405 | 405 |     |     |     |
| V | 409 | 409 | 409 |     |     |     |
| P | 410 | 410 |     |     |     |     |
| G | 411 | 411 |     |     |     |     |
| S | 413 | 413 | 413 | 413 |     |     |
| S | 414 | 414 | 414 | 414 | 414 |     |
| R | 415 |     |     |     |     |     |

FIG. 17D

|   | 1 | 2 | 3 | 4 | 5 | 6 |   | 1 | 2 | 3 | 4 | 5 | 6 |   | 1 | 2 | 3 | 4 | 5 | 6 |
|---|---|---|---|---|---|---|---|---|---|---|---|---|---|---|---|---|---|---|---|---|
| W | 418 | 418 | 418 |   |   |   | M | 492 | 492 | 492 |   |   |   | A | 561 | 561 | 561 |   |   |   |
| T | 419 |   |   |   |   |   | A | 493 | 493 | 493 |   |   |   | F | 563 | 563 | 563 |   |   |   |
| P | 423 | 423 |   |   |   |   | L | 494 | 494 | 494 |   |   |   | A | 564 | 564 | 564 |   |   |   |
| D | 425 |   |   |   |   |   | S | 497 | 497 | 497 |   |   |   | T | 565 | 565 | 565 | 565 |   |   |
| L | 427 | 427 | 427 |   |   |   | H | 498 | 498 | 498 | 498 | 498 | 498 | P | 566 | 566 |   |   |   |   |
| P | 428 | 428 |   |   |   |   | A | 500 | 500 | 500 |   |   |   | T | 567 | 567 | 567 | 567 | 567 |   |
| R | 429 |   |   |   |   |   | V | 501 | 501 | 501 |   |   |   | L | 569 | 569 | 569 |   |   |   |
| V | 430 | 430 | 430 |   |   |   | A | 503 | 503 | 503 |   |   |   | D | 570 |   |   |   |   |   |
| N | 432 |   |   |   |   |   | D | 504 |   |   |   |   |   | V | 573 | 573 | 573 |   |   |   |
| P | 433 | 433 |   |   |   |   | T | 506 | 506 | 506 |   |   |   | S | 574 | 574 | 574 | 574 | 574 |   |
| P | 434 | 434 |   |   |   |   | L | 507 | 507 | 507 |   |   |   | G | 578 | 578 |   |   |   |   |
| G | 435 | 435 |   |   |   |   | P | 508 | 508 |   |   |   |   | V | 579 | 579 | 579 |   |   |   |
| G | 436 | 436 |   |   |   |   | D | 509 |   |   |   |   |   | R | 580 | 580 | 580 | 580 | 580 |   |
| F | 437 | 437 | 437 |   |   |   | I | 511 | 511 | 511 |   |   |   | K | 583 |   |   |   |   |   |
| V | 438 | 438 | 438 |   |   |   | A | 514 | 514 | 514 | 514 |   |   | A | 584 | 584 | 584 |   |   |   |
| N | 440 | 440 | 440 | 440 |   |   | L | 515 | 515 | 515 |   |   |   | A | 585 | 585 | 585 |   |   |   |
| S | 441 | 441 | 441 | 441 | 441 |   | I | 516 | 516 | 516 |   |   |   | V | 586 | 586 | 586 | 586 | 586 |   |
| N | 442 | 442 | 442 | 442 |   |   | D | 519 |   |   |   |   |   | D | 587 |   |   |   |   |   |
| D | 443 |   |   |   |   |   | A | 524 | 524 | 524 |   |   |   | L | 589 | 589 | 589 |   |   |   |
| P | 445 | 445 | 445 |   |   |   | A | 525 | 525 | 525 |   |   |   | R | 590 | 590 | 590 | 590 |   |   |
| T | 446 | 446 | 446 | 446 |   |   | R | 526 | 526 | 526 | 526 |   |   | T | 591 | 591 | 591 | 591 | 591 |   |
| T | 447 | 447 | 447 | 447 |   |   | L | 527 | 527 | 527 |   |   |   | A | 592 | 592 | 592 |   |   |   |
| V | 452 | 452 | 452 |   |   |   | L | 528 | 528 | 528 |   |   |   | N | 595 | 595 | 595 | 595 | 595 |   |
| T | 453 |   |   |   |   |   | A | 530 | 530 | 530 |   |   |   | L | 596 | 596 | 596 |   |   |   |
| Y | 454 | 454 | 454 |   |   |   | W | 531 | 531 | 531 |   |   |   | T | 597 | 597 | 597 | 597 | 597 |   |
| P | 456 | 456 | 456 |   |   |   | D | 532 |   |   |   |   |   | R | 599 |   |   |   |   |   |
| K | 457 | 457 | 457 | 457 | 457 |   | R | 533 | 533 | 533 | 533 | 533 | 533 | Y | 601 | 601 | 601 |   |   |   |
| D | 458 |   |   |   |   |   | F | 535 | 535 | 535 |   |   |   | G | 602 | 602 |   |   |   |   |
| P | 460 | 460 |   |   |   |   | T | 536 | 536 | 536 | 536 |   |   | D | 605 |   |   |   |   |   |
| S | 461 | 461 | 461 | 461 | 461 |   | S | 537 | 537 | 537 |   |   |   | R | 606 |   |   |   |   |   |
| Y | 462 | 462 | 462 |   |   |   | S | 539 | 539 | 539 | 539 |   |   | P | 607 | 607 |   |   |   |   |
| A | 464 | 464 | 464 |   |   |   | R | 540 | 540 | 540 | 540 | 540 |   | D | 610 |   |   |   |   |   |
| Q | 466 | 466 | 466 | 466 | 466 |   | A | 541 | 541 | 541 |   |   |   | S | 612 | 612 | 612 | 612 | 612 |   |
| H | 469 |   |   |   |   |   | A | 542 | 542 | 542 | 542 |   |   | I | 615 | 615 | 615 |   |   |   |
| S | 470 | 470 | 470 | 470 |   |   | L | 544 | 544 | 544 |   |   |   | V | 619 | 619 | 619 |   |   |   |
| L | 471 | 471 | 471 |   |   |   | E | 546 | 546 | 546 | 546 | 546 |   | V | 621 | 621 | 621 |   |   |   |
| A | 473 | 473 | 473 |   |   |   | W | 548 | 548 | 548 |   |   |   | P | 622 | 622 | 622 |   |   |   |
| S | 476 | 476 | 476 | 476 |   |   | A | 549 | 549 | 549 |   |   |   | G | 623 | 623 | 623 |   |   |   |
| V | 477 | 477 | 477 |   |   |   | R | 550 | 550 | 550 | 550 | 550 | 550 | N | 629 | 629 | 629 | 629 |   |   |
| R | 478 |   |   |   |   |   | F | 551 | 551 | 551 |   |   |   | S | 632 | 632 | 632 | 632 |   |   |
| M | 480 | 480 | 480 |   |   |   | L | 552 | 552 | 552 |   |   |   | R | 634 | 634 | 634 | 634 | 634 | 634 |
| S | 481 | 481 | 481 | 481 | 481 |   | A | 553 | 553 | 553 |   |   |   | V | 635 | 635 | 635 |   |   |   |
| T | 487 | 487 | 487 | 487 |   |   | G | 554 | 554 |   |   |   |   | G | 636 | 636 | 636 |   |   |   |
| L | 488 | 488 | 488 |   |   |   | N | 556 | 556 | 556 | 556 |   |   | T | 637 | 637 | 637 | 637 | 637 |   |
| E | 489 |   |   |   |   |   | G | 559 | 559 |   |   |   |   | T | 638 | 638 | 638 | 638 |   |   |
|   |   |   |   |   |   |   | Q | 560 | 560 | 560 | 560 |   |   | S | 639 |   |   |   |   |   |

FIG. 17E

|   | 1 | 2 | 3 | 4 | 5 | 6 |
|---|---|---|---|---|---|---|
| D | 640 | | | | | |
| P | 641 | 641 | 641 | | | |
| H | 644 | | | | | |
| V | 646 | 646 | 646 | | | |
| T | 648 | 648 | 648 | 648 | | |
| P | 649 | 649 | | | | |
| V | 650 | 650 | 650 | 650 | | |
| G | 652 | 652 | | | | |
| E | 653 | | | | | |
| T | 654 | 654 | 654 | 654 | | |
| W | 655 | 655 | 655 | | | |
| V | 656 | 656 | 656 | | | |
| A | 657 | 657 | 657 | | | |
| M | 658 | 658 | 658 | | | |
| E | 660 | | | | | |
| F | 661 | 661 | 661 | | | |
| S | 662 | | | | | |
| T | 663 | 663 | 663 | 663 | 663 | |
| R | 666 | 666 | 666 | 666 | 666 | |

|   | 1 | 2 | 3 | 4 | 5 | 6 |
|---|---|---|---|---|---|---|
| Y | 668 | 668 | 668 | | | |
| L | 670 | 670 | 670 | | | |
| M | 671 | 671 | 671 | | | |
| G | 674 | 674 | | | | |
| S | 676 | 676 | 676 | 676 | | |
| P | 679 | 679 | | | | |
| G | 680 | 680 | 680 | | | |
| T | 681 | 681 | 681 | 681 | | |
| T | 682 | 682 | 682 | 682 | | |
| H | 683 | | | | | |
| Y | 684 | 684 | 684 | | | |
| S | 685 | 685 | 685 | 685 | | |
| D | 686 | | | | | |
| Q | 687 | 687 | 687 | 687 | | |
| E | 689 | | | | | |
| V | 691 | | | | | |
| R | 693 | 693 | 693 | 693 | | |
| F | 696 | 696 | 696 | | | |
| L | 700 | 700 | 700 | | | |

|   | 1 | 2 | 3 | 4 | 5 | 6 |
|---|---|---|---|---|---|---|
| L | 701 | 701 | 701 | | | |
| R | 703 | | | | | |
| Q | 705 | | | | | |
| A | 708 | | | | | |
| A | 709 | 709 | 709 | 709 | | |
| V | 710 | 710 | 710 | 710 | | |
| Q | 711 | 711 | 711 | 711 | | |
| E | 712 | | | | | |
| F | 716 | 716 | 716 | | | |
| F | 718 | 718 | 718 | | | |

FIG. 17F

ND E-LACTAM ACYLASE GENES

SEQUENCE LISTING ( 1 ) GENERAL INFORMATION:

( i i i ) NUMBER OF SEQUENCES: 50

( 2 ) INFORMATION FOR SEQ ID NO: 1:

( i ) SEQUENCE CHARACTERISTICS:
        ( A ) LENGTH: 2163 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: Pseudomonas species
        ( B ) STRAIN: SY77

( i x ) FEATURE:
        ( A ) NAME/KEY: CDS
        ( B ) LOCATION: 1..2163
        ( C ) IDENTIFICATION METHOD: experimental
        ( D ) OTHER INFORMATION: /codon_start=1
            / product="Glutaryl-Cef acylase"
            / evidence=EXPERIMENTAL ( i x ) FEATURE:
        ( A ) NAME/KEY: sig_peptide
        ( B ) LOCATION: 1..87

( i x ) FEATURE:
        ( A ) NAME/KEY; mat_peptide
        ( B ) LOCATION: 88..594
        ( D ) OTHER INFORMATION: /product="glutaryl-cef acylase"
            / label=alfa-subunit ( i x ) FEATURE:
        ( A ) NAME/KEY: mat_peptide
        ( B ) LOCATION: 595..2163
        ( D ) OTHER INFORMATION: /product="glutaryl-cef acylase"
            / label=beta-subunit ( x i ) SEQUENCE DESCRIPTION: SEQ ID NO: 1:

```
ATG  CTG  AGA  GTT  CTG  CAC  CGG  GCG  GCG  TCC  GCC  TTG  GTT  ATG  GCG  ACT         48
Met  Leu  Arg  Val  Leu  His  Arg  Ala  Ala  Ser  Ala  Leu  Val  Met  Ala  Thr
-29            -25                      -20                      -15

GTG  ATC  GGC  CTT  GCG  CCC  GCC  GTC  GCC  TTT  GCG  CTG  GCC  GAG  CCG  ACC         96
Val  Ile  Gly  Leu  Ala  Pro  Ala  Val  Ala  Phe  Ala  Leu  Ala  Glu  Pro  Thr
               -10                       -5                            1

TCG  ACG  CCG  CAG  GCG  CCG  ATT  GCG  GCC  TAT  AAA  CCG  AGA  AGC  AAT  GAG        144
Ser  Thr  Pro  Gln  Ala  Pro  Ile  Ala  Ala  Tyr  Lys  Pro  Arg  Ser  Asn  Glu
          5                         10                  15

ATC  CTG  TGG  GAC  GGC  TAC  GGC  GTC  CCG  CAC  ATC  TAC  GGC  GTC  GAC  GCG        192
Ile  Leu  Trp  Asp  Gly  Tyr  Gly  Val  Pro  His  Ile  Tyr  Gly  Val  Asp  Ala
20                       25                       30                        35

CCC  TCA  GCC  TTC  TAC  GGC  TAT  GGC  TGG  GCC  CAG  GCG  CGC  AGC  CAG  GGC        240
Pro  Ser  Ala  Phe  Tyr  Gly  Tyr  Gly  Trp  Ala  Gln  Ala  Arg  Ser  Gln  Gly
                    40                       45                  50

GAC  AAT  ATC  CTG  CGC  CTG  TAT  GGA  GAA  GCG  CGG  GGC  AAG  GGG  GCC  GAA        288
Asp  Asn  Ile  Leu  Arg  Leu  Tyr  Gly  Glu  Ala  Arg  Gly  Lys  Gly  Ala  Glu
               55                       60                  65

TAC  TGG  GGC  CCG  GAT  TAC  GAA  CAG  ACG  ACC  GTC  TGG  CTG  CTG  ACC  AAC        336
Tyr  Trp  Gly  Pro  Asp  Tyr  Glu  Gln  Thr  Thr  Val  Trp  Leu  Leu  Thr  Asn
          70                       75                       80
```

| | | | | | | | | | | | | | | | | |
|---|---|---|---|---|---|---|---|---|---|---|---|---|---|---|---|---|
| GGC | GTG | CCG | GAG | CGC | GCT | CAG | CAG | TGG | TAT | GCG | CAG | CAG | TCG | CCT | GAT | 384 |
| Gly | Val | Pro | Glu | Arg | Ala | Gln | Gln | Trp | Tyr | Ala | Gln | Gln | Ser | Pro | Asp | |
| | 85 | | | | | 90 | | | | | 95 | | | | | |
| TTC | CGC | GCC | AAC | CTC | GAC | GCC | TTC | GCG | GCG | GGC | ATC | AAC | GCC | TAT | GCG | 432 |
| Phe | Arg | Ala | Asn | Leu | Asp | Ala | Phe | Ala | Ala | Gly | Ile | Asn | Ala | Tyr | Ala | |
| 100 | | | | | 105 | | | | | 110 | | | | | 115 | |
| CAG | CAG | AAC | CCC | GAC | GAC | ATC | TCG | CCC | GAC | GTG | CGG | CAG | GTG | CTG | CCG | 480 |
| Gln | Gln | Asn | Pro | Asp | Asp | Ile | Ser | Pro | Asp | Val | Arg | Gln | Val | Leu | Pro | |
| | | | | 120 | | | | | 125 | | | | | 130 | | |
| GTT | TCC | GGC | GCC | GAC | GTG | GTG | GCC | CAC | GCC | CAC | CGC | CTG | ATG | AAC | TTC | 528 |
| Val | Ser | Gly | Ala | Asp | Val | Val | Ala | His | Ala | His | Arg | Leu | Met | Asn | Phe | |
| | | | 135 | | | | | 140 | | | | | 145 | | | |
| CTC | TAT | GTC | GCG | TCG | CCC | GGC | CGC | ACC | CTG | GGC | GAG | GGC | GAC | CCG | CCG | 576 |
| Leu | Tyr | Val | Ala | Ser | Pro | Gly | Arg | Thr | Leu | Gly | Glu | Gly | Asp | Pro | Pro | |
| | | 150 | | | | | 155 | | | | | 160 | | | | |
| GAC | CTG | GCC | GAT | CAA | GGA | TCC | AAC | TCC | TGG | GCG | GTG | GCG | CCG | GGA | AAG | 624 |
| Asp | Leu | Ala | Asp | Gln | Gly | Ser | Asn | Ser | Trp | Ala | Val | Ala | Pro | Gly | Lys | |
| | 165 | | | | | 170 | | | | | 175 | | | | | |
| ACG | GCG | AAC | GGG | AAC | GCC | CTG | CTG | CTG | CAG | AAC | CCG | CAC | CTG | TCC | TGG | 672 |
| Thr | Ala | Asn | Gly | Asn | Ala | Leu | Leu | Leu | Gln | Asn | Pro | His | Leu | Ser | Trp | |
| 180 | | | | | 185 | | | | | 190 | | | | | 195 | |
| ACG | ACG | GAC | TAC | TTC | ACC | TAC | TAC | GAG | GCG | CAT | CTC | GTC | ACG | CCG | GAC | 720 |
| Thr | Thr | Asp | Tyr | Phe | Thr | Tyr | Tyr | Glu | Ala | His | Leu | Val | Thr | Pro | Asp | |
| | | | | 200 | | | | | 205 | | | | | 210 | | |
| TTC | GAA | ATC | TAT | GGC | GCG | ACC | CAG | ATC | GGC | CTG | CCG | GTC | ATC | CGC | TTC | 768 |
| Phe | Glu | Ile | Tyr | Gly | Ala | Thr | Gln | Ile | Gly | Leu | Pro | Val | Ile | Arg | Phe | |
| | | | 215 | | | | | 220 | | | | | 225 | | | |
| GCC | TTC | AAC | CAG | CGG | ATG | GGC | ATC | ACC | AAT | ACC | GTC | AAC | GGC | ATG | GTG | 816 |
| Ala | Phe | Asn | Gln | Arg | Met | Gly | Ile | Thr | Asn | Thr | Val | Asn | Gly | Met | Val | |
| | | 230 | | | | | 235 | | | | | 240 | | | | |
| GGG | GCC | ACC | AAC | TAT | CGG | CTG | ACG | CTT | CAG | GAC | GGC | GGC | TAT | CTG | TAT | 864 |
| Gly | Ala | Thr | Asn | Tyr | Arg | Leu | Thr | Leu | Gln | Asp | Gly | Gly | Tyr | Leu | Tyr | |
| | 245 | | | | | 250 | | | | | 255 | | | | | |
| GAC | GGT | CAG | GTG | CGG | CCG | TTC | GAG | CGG | CCT | CAG | GCC | TCG | TAT | CGC | CTG | 912 |
| Asp | Gly | Gln | Val | Arg | Pro | Phe | Glu | Arg | Pro | Gln | Ala | Ser | Tyr | Arg | Leu | |
| 260 | | | | | 265 | | | | | 270 | | | | | 275 | |
| CGT | CAG | GCG | GAC | GGG | ACG | ACG | GTC | GAC | AAG | CCG | TTG | GAG | ATC | CGC | TCC | 960 |
| Arg | Gln | Ala | Asp | Gly | Thr | Thr | Val | Asp | Lys | Pro | Leu | Glu | Ile | Arg | Ser | |
| | | | | 280 | | | | | 285 | | | | | 290 | | |
| AGC | GTC | CAT | GGC | CCG | GTC | TTC | GAG | CGC | GCG | GAC | GGC | ACG | GCC | GTC | GCC | 1008 |
| Ser | Val | His | Gly | Pro | Val | Phe | Glu | Arg | Ala | Asp | Gly | Thr | Ala | Val | Ala | |
| | | | 295 | | | | | 300 | | | | | 305 | | | |
| GTT | CGG | GTC | GCC | GGT | CTG | GAC | CGG | CCG | GGC | ATG | CTC | GAG | CAG | TAT | TTC | 1056 |
| Val | Arg | Val | Ala | Gly | Leu | Asp | Arg | Pro | Gly | Met | Leu | Glu | Gln | Tyr | Phe | |
| | | 310 | | | | | 315 | | | | | 320 | | | | |
| GAC | ATG | ATC | ACG | GCG | GAC | AGC | TTC | GAC | GAC | TAC | GAA | GCC | GCT | TTG | GCG | 1104 |
| Asp | Met | Ile | Thr | Ala | Asp | Ser | Phe | Asp | Asp | Tyr | Glu | Ala | Ala | Leu | Ala | |
| | 325 | | | | | 330 | | | | | 335 | | | | | |
| CGG | ATG | CAG | GTG | CCG | ACC | TTC | AAC | ATC | GTC | TAC | GCC | GAC | CGC | GAA | GGG | 1152 |
| Arg | Met | Gln | Val | Pro | Thr | Phe | Asn | Ile | Val | Tyr | Ala | Asp | Arg | Glu | Gly | |
| 340 | | | | | 345 | | | | | 350 | | | | | 355 | |
| ACC | ATC | AAC | TAC | AGC | TTC | AAC | GGC | GTG | GCG | CCC | AAA | CGG | GCC | GAG | GGC | 1200 |
| Thr | Ile | Asn | Tyr | Ser | Phe | Asn | Gly | Val | Ala | Pro | Lys | Arg | Ala | Glu | Gly | |
| | | | | 360 | | | | | 365 | | | | | 370 | | |
| GAC | ATC | GCC | TTC | TGG | CAG | GGC | CTC | GTG | CCG | GGC | GAT | TCC | TCG | CGT | TAC | 1248 |
| Asp | Ile | Ala | Phe | Trp | Gln | Gly | Leu | Val | Pro | Gly | Asp | Ser | Ser | Arg | Tyr | |
| | | | 375 | | | | | 380 | | | | | 385 | | | |
| CTG | TGG | ACC | GAG | ACA | CAC | CCG | CTG | GAC | GAT | CTG | CCG | CGC | GTC | ACC | AAT | 1296 |
| Leu | Trp | Thr | Glu | Thr | His | Pro | Leu | Asp | Asp | Leu | Pro | Arg | Val | Thr | Asn | |

|  |  |  |  |  |  |  |  |  |  |  |  |  |  |  |  |
|---|---|---|---|---|---|---|---|---|---|---|---|---|---|---|---|
|  | 390 |  |  |  |  | 395 |  |  |  |  | 400 |  |  |  |  |
| CCG<br>Pro<br>405 | CCG<br>Pro | GGC<br>Gly | GGC<br>Gly | TTC<br>Phe | GTG<br>Val | CAG<br>Gln<br>410 | AAC<br>Asn | TCC<br>Ser | AAT<br>Asn | GAT<br>Asp | CCG<br>Pro<br>415 | CCG<br>Pro | TGG<br>Trp | ACG<br>Thr | CCG<br>Pro | 1344 |
| ACC<br>Thr<br>420 | TGG<br>Trp | CCC<br>Pro | GTC<br>Val | ACC<br>Thr | TAC<br>Tyr | ACG<br>Thr<br>425 | CCC<br>Pro | AAG<br>Lys | GAC<br>Asp | TTC<br>Phe | CCC<br>Pro<br>430 | TCC<br>Ser | TAT<br>Tyr | CTG<br>Leu | GCG<br>Ala<br>435 | 1392 |
| CCC<br>Pro | CAG<br>Gln | ACG<br>Thr | CCG<br>Pro | CAT<br>His<br>440 | TCC<br>Ser | CTG<br>Leu | CGT<br>Arg | GCG<br>Ala | CAA<br>Gln | CAA<br>Gln<br>445 | AGC<br>Ser | GTG<br>Val | CGT<br>Arg | CTG<br>Leu<br>450 | ATG<br>Met | 1440 |
| TCC<br>Ser | GAG<br>Glu | AAC<br>Asn | GAC<br>Asp | GAC<br>Asp<br>455 | CTG<br>Leu | ACG<br>Thr | CTG<br>Leu | GAG<br>Glu | CGC<br>Arg<br>460 | TTC<br>Phe | ATG<br>Met | GCG<br>Ala | CTG<br>Leu | CAG<br>Gln<br>465 | TTG<br>Leu | 1488 |
| AGC<br>Ser | CAT<br>His | CGC<br>Arg<br>470 | GCC<br>Ala | GTC<br>Val | ATG<br>Met | GCC<br>Ala | GAC<br>Asp<br>475 | CGC<br>Arg | ACC<br>Thr | TTG<br>Leu | CCG<br>Pro | GAC<br>Asp<br>480 | CTG<br>Leu | ATC<br>Ile | CCG<br>Pro | 1536 |
| GCC<br>Ala | GCC<br>Ala<br>485 | CTG<br>Leu | ATC<br>Ile | GAC<br>Asp | CCC<br>Pro | GAT<br>Asp<br>490 | CCC<br>Pro | GAG<br>Glu | GTC<br>Val | CAG<br>Gln | GCG<br>Ala<br>495 | GCG<br>Ala | GCG<br>Ala | CGC<br>Arg | CTG<br>Leu | 1584 |
| CTG<br>Leu<br>500 | GCG<br>Ala | GCG<br>Ala | TGG<br>Trp | GAT<br>Asp | CGC<br>Arg<br>505 | GAG<br>Glu | TTC<br>Phe | ACC<br>Thr | AGC<br>Ser | GAC<br>Asp<br>510 | AGC<br>Ser | CGC<br>Arg | GCC<br>Ala | GCC<br>Ala | CTG<br>Leu<br>515 | 1632 |
| CTG<br>Leu | TTC<br>Phe | GAG<br>Glu | GAA<br>Glu | TGG<br>Trp<br>520 | GCG<br>Ala | CGT<br>Arg | CTG<br>Leu | TTC<br>Phe | GCC<br>Ala<br>525 | GGC<br>Gly | CAG<br>Gln | AAT<br>Asn | TTC<br>Phe | GCA<br>Ala<br>530 | GGC<br>Gly | 1680 |
| CAG<br>Gln | GCC<br>Ala | GGC<br>Gly | TTC<br>Phe<br>535 | GCC<br>Ala | ACG<br>Thr | CCC<br>Pro | TGG<br>Trp | TCG<br>Ser<br>540 | CTG<br>Leu | GAT<br>Asp | AAG<br>Lys | CCG<br>Pro | GTC<br>Val<br>545 | AGC<br>Ser | ACG<br>Thr | 1728 |
| CCT<br>Pro | TAC<br>Tyr | GGC<br>Gly<br>550 | GTC<br>Val | CGC<br>Arg | GAC<br>Asp | CCC<br>Pro | AAG<br>Lys<br>555 | GCC<br>Ala | GCC<br>Ala | GTC<br>Val | GAT<br>Asp | CAA<br>Gln<br>560 | CTG<br>Leu | CGG<br>Arg | ACC<br>Thr | 1776 |
| GCC<br>Ala | ATC<br>Ile<br>565 | GCC<br>Ala | AAC<br>Asn | ACC<br>Thr | AAG<br>Lys | CGC<br>Arg<br>570 | AAA<br>Lys | TAC<br>Tyr | GGC<br>Gly | GCG<br>Ala | ATC<br>Ile<br>575 | GAC<br>Asp | CGG<br>Arg | CCG<br>Pro | TTC<br>Phe | 1824 |
| GGC<br>Gly<br>580 | GAC<br>Asp | GCC<br>Ala | TCG<br>Ser | CGC<br>Arg | ATG<br>Met<br>585 | ATC<br>Ile | CTG<br>Leu | AAC<br>Asn | GAC<br>Asp | GTG<br>Val<br>590 | AAT<br>Asn | GTT<br>Val | CCG<br>Pro | GGC<br>Gly | GCC<br>Ala<br>595 | 1872 |
| GCC<br>Ala | GGC<br>Gly | TAC<br>Tyr | GGC<br>Gly | AAC<br>Asn<br>600 | CTG<br>Leu | GGT<br>Gly | TCC<br>Ser | TTC<br>Phe | CGG<br>Arg<br>605 | GTC<br>Val | TTC<br>Phe | ACC<br>Thr | TGG<br>Trp | TCC<br>Ser<br>610 | GAT<br>Asp | 1920 |
| CCT<br>Pro | GAC<br>Asp | GAA<br>Glu | AAC<br>Asn<br>615 | GGG<br>Gly | GTT<br>Val | CGC<br>Arg | ACG<br>Thr | CCC<br>Pro<br>620 | GTC<br>Val | CAC<br>His | GGC<br>Gly | GAG<br>Glu | ACG<br>Thr<br>625 | TGG<br>Trp | GTG<br>Val | 1968 |
| GCG<br>Ala | ATG<br>Met | ATC<br>Ile<br>630 | GAG<br>Glu | TTC<br>Phe | TCC<br>Ser | ACG<br>Thr | CCG<br>Pro<br>635 | GTG<br>Val | CGG<br>Arg | GCC<br>Ala | TAT<br>Tyr | GGC<br>Gly<br>640 | CTG<br>Leu | ATG<br>Met | AGC<br>Ser | 2016 |
| TAC<br>Tyr | GGC<br>Gly<br>645 | AAC<br>Asn | TCT<br>Ser | CGC<br>Arg | CAG<br>Gln | CCG<br>Pro<br>650 | GGC<br>Gly | ACG<br>Thr | ACG<br>Thr | CAC<br>His | TAC<br>Tyr<br>655 | AGC<br>Ser | GAT<br>Asp | CAG<br>Gln | ATC<br>Ile | 2064 |
| GAA<br>Glu<br>660 | CGC<br>Arg | GTG<br>Val | TCG<br>Ser | CGC<br>Arg | GCC<br>Ala<br>665 | GAC<br>Asp | TTC<br>Phe | CGC<br>Arg | GAA<br>Glu | CTG<br>Leu<br>670 | TTG<br>Leu | CTG<br>Leu | CGG<br>Arg | CGA<br>Arg | GAG<br>Glu<br>675 | 2112 |
| CAG<br>Gln | GTC<br>Val | GAG<br>Glu | GCC<br>Ala | GCC<br>Ala<br>680 | GTC<br>Val | CAG<br>Gln | GAA<br>Glu | CGC<br>Arg | ACG<br>Thr<br>685 | CCC<br>Pro | TTC<br>Phe | AAC<br>Asn | TTC<br>Phe | AAG<br>Lys<br>690 | CCA<br>Pro | 2160 |
| TGA |  |  |  |  |  |  |  |  |  |  |  |  |  |  |  | 2163 |

( 2 ) INFORMATION FOR SEQ ID NO: 2:

(i) SEQUENCE CHARACTERISTICS:
    (A) LENGTH: 720 amino acids
    (B) TYPE: amino acid
    (D) TOPOLOGY: linear (ii) MOLECULE TYPE: protein (xi) SEQUENCE DESCRIPTION: SEQ ID NO: 2:

```
Met  Leu  Arg  Val  Leu  His  Arg  Ala  Ala  Ser  Ala  Leu  Val  Met  Ala  Thr
-29            -25                      -20                      -15

Val  Ile  Gly  Leu  Ala  Pro  Ala  Val  Ala  Phe  Ala  Leu  Ala  Glu  Pro  Thr
               -10                  -5                            1

Ser  Thr  Pro  Gln  Ala  Pro  Ile  Ala  Ala  Tyr  Lys  Pro  Arg  Ser  Asn  Glu
      5                       10                      15

Ile  Leu  Trp  Asp  Gly  Tyr  Gly  Val  Pro  His  Ile  Tyr  Gly  Val  Asp  Ala
 20                 25                      30                           35

Pro  Ser  Ala  Phe  Tyr  Gly  Tyr  Gly  Trp  Ala  Gln  Ala  Arg  Ser  Gln  Gly
                40                      45                          50

Asp  Asn  Ile  Leu  Arg  Leu  Tyr  Gly  Glu  Ala  Arg  Gly  Lys  Gly  Ala  Glu
                55                      60                          65

Tyr  Trp  Gly  Pro  Asp  Tyr  Glu  Gln  Thr  Thr  Val  Trp  Leu  Leu  Thr  Asn
          70                  75                          80

Gly  Val  Pro  Glu  Arg  Ala  Gln  Gln  Trp  Tyr  Ala  Gln  Gln  Ser  Pro  Asp
      85                      90                      95

Phe  Arg  Ala  Asn  Leu  Asp  Ala  Phe  Ala  Ala  Gly  Ile  Asn  Ala  Tyr  Ala
100                 105                      110                         115

Gln  Gln  Asn  Pro  Asp  Asp  Ile  Ser  Pro  Asp  Val  Arg  Gln  Val  Leu  Pro
                120                      125                         130

Val  Ser  Gly  Ala  Asp  Val  Val  Ala  His  Ala  His  Arg  Leu  Met  Asn  Phe
               135                      140                         145

Leu  Tyr  Val  Ala  Ser  Pro  Gly  Arg  Thr  Leu  Gly  Glu  Gly  Asp  Pro  Pro
          150                      155                     160

Asp  Leu  Ala  Asp  Gln  Gly  Ser  Asn  Ser  Trp  Ala  Val  Ala  Pro  Gly  Lys
     165                      170                     175

Thr  Ala  Asn  Gly  Asn  Ala  Leu  Leu  Leu  Gln  Asn  Pro  His  Leu  Ser  Trp
180                     185                      190                      195

Thr  Thr  Asp  Tyr  Phe  Thr  Tyr  Tyr  Glu  Ala  His  Leu  Val  Thr  Pro  Asp
               200                      205                         210

Phe  Glu  Ile  Tyr  Gly  Ala  Thr  Gln  Ile  Gly  Leu  Pro  Val  Ile  Arg  Phe
               215                      220                         225

Ala  Phe  Asn  Gln  Arg  Met  Gly  Ile  Thr  Asn  Thr  Val  Asn  Gly  Met  Val
          230                      235                     240

Gly  Ala  Thr  Asn  Tyr  Arg  Leu  Thr  Leu  Gln  Asp  Gly  Gly  Tyr  Leu  Tyr
     245                      250                     255

Asp  Gly  Gln  Val  Arg  Pro  Phe  Glu  Arg  Pro  Gln  Ala  Ser  Tyr  Arg  Leu
260                      265                     270                      275

Arg  Gln  Ala  Asp  Gly  Thr  Thr  Val  Asp  Lys  Pro  Leu  Glu  Ile  Arg  Ser
                280                      285                         290

Ser  Val  His  Gly  Pro  Val  Phe  Glu  Arg  Ala  Asp  Gly  Thr  Ala  Val  Ala
               295                      300                         305

Val  Arg  Val  Ala  Gly  Leu  Asp  Arg  Pro  Gly  Met  Leu  Glu  Gln  Tyr  Phe
          310                      315                     320

Asp  Met  Ile  Thr  Ala  Asp  Ser  Phe  Asp  Asp  Tyr  Glu  Ala  Ala  Leu  Ala
     325                      330                     335

Arg  Met  Gln  Val  Pro  Thr  Phe  Asn  Ile  Val  Tyr  Ala  Asp  Arg  Glu  Gly
```

|   340 |       |     |     |   345 |     |     |     |   350 |     |     |     |   355 |     |
|-------|-------|-----|-----|-------|-----|-----|-----|-------|-----|-----|-----|-------|-----|

Thr Ile Asn Tyr Ser Phe Asn Gly Val Ala Pro Lys Arg Ala Glu Gly
                    360                 365                 370

Asp Ile Ala Phe Trp Gln Gly Leu Val Pro Gly Asp Ser Ser Arg Tyr
                375                 380                 385

Leu Trp Thr Glu Thr His Pro Leu Asp Asp Leu Pro Arg Val Thr Asn
            390             395                 400

Pro Pro Gly Gly Phe Val Gln Asn Ser Asn Asp Pro Pro Trp Thr Pro
    405             410                 415

Thr Trp Pro Val Thr Tyr Thr Pro Lys Asp Phe Pro Ser Tyr Leu Ala
420                 425                 430                 435

Pro Gln Thr Pro His Ser Leu Arg Ala Gln Gln Ser Val Arg Leu Met
                440                 445                 450

Ser Glu Asn Asp Asp Leu Thr Leu Glu Arg Phe Met Ala Leu Gln Leu
                455                 460                 465

Ser His Arg Ala Val Met Ala Asp Arg Thr Leu Pro Asp Leu Ile Pro
        470                 475                 480

Ala Ala Leu Ile Asp Pro Asp Pro Glu Val Gln Ala Ala Ala Arg Leu
    485                 490                 495

Leu Ala Ala Trp Asp Arg Glu Phe Thr Ser Asp Ser Arg Ala Ala Leu
500                 505                 510                 515

Leu Phe Glu Glu Trp Ala Arg Leu Phe Ala Gly Gln Asn Phe Ala Gly
                520                 525                 530

Gln Ala Gly Phe Ala Thr Pro Trp Ser Leu Asp Lys Pro Val Ser Thr
            535                 540                 545

Pro Tyr Gly Val Arg Asp Pro Lys Ala Ala Val Asp Gln Leu Arg Thr
        550                 555                 560

Ala Ile Ala Asn Thr Lys Arg Lys Tyr Gly Ala Ile Asp Arg Pro Phe
    565                 570                 575

Gly Asp Ala Ser Arg Met Ile Leu Asn Asp Val Asn Val Pro Gly Ala
580                 585                 590                 595

Ala Gly Tyr Gly Asn Leu Gly Ser Phe Arg Val Phe Thr Trp Ser Asp
            600                 605                 610

Pro Asp Glu Asn Gly Val Arg Thr Pro Val His Gly Glu Thr Trp Val
            615                 620                 625

Ala Met Ile Glu Phe Ser Thr Pro Val Arg Ala Tyr Gly Leu Met Ser
        630                 635                 640

Tyr Gly Asn Ser Arg Gln Pro Gly Thr Thr His Tyr Ser Asp Gln Ile
645                 650                 655

Glu Arg Val Ser Arg Ala Asp Phe Arg Glu Leu Leu Leu Arg Arg Glu
660                 665                 670                 675

Gln Val Glu Ala Ala Val Gln Glu Arg Thr Pro Phe Asn Phe Lys Pro
                680                 685                 690

( 2 ) INFORMATION FOR SEQ ID NO: 3:

( i ) SEQUENCE CHARACTERISTICS:
        ( A ) LENGTH: 2451 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i i i ) ANTI-SENSE: NO (v i) ORIGINAL SOURCE:
  (A) ORGANISM: Alcaligenes faecalis
  (B) STRAIN: ATCC 19018 (=NCTC415)
  (I) ORGANELLE: Chloroplast (i x) FEATURE:
  (A) NAME/KEY: CDS
  (B) LOCATION: 1..2451

(i x) FEATURE:
  (A) NAME/KEY: sig_peptide
  (B) LOCATION: 1..78
  (C) IDENTIFICATION METHOD: experimental
  (D) OTHER INFORMATION: /product="penicillin acylase"
       / evidence=EXPERIMENTAL (i x) FEATURE:
  (A) NAME/KEY: mat_peptide
  (B) LOCATION: 79..708
  (D) OTHER INFORMATION: /product="penicillin acylase"
       / label=alpha-subunit (i x) FEATURE:
  (A) NAME/KEY: mat_peptide
  (B) LOCATION: 709..2448
  (C) IDENTIFICATION METHOD: experimental
  (D) OTHER INFORMATION: /product="penicillin acylase"
       / evidence=EXPERIMENTAL
       / label=beta-subunit (x i) SEQUENCE DESCRIPTION: SEQ ID NO: 3:

| | | | | | | | | | | | | | | | | |
|---|---|---|---|---|---|---|---|---|---|---|---|---|---|---|---|---|
| ATG | CAG | AAA | GGG | CTT | GTT | CGT | ACC | GGG | CTT | GTG | GCC | GCT | GGT | TTG | ATC | 48 |
| Met | Gln | Lys | Gly | Leu | Val | Arg | Thr | Gly | Leu | Val | Ala | Ala | Gly | Leu | Ile | |
| -26 | -25 | | | | | -20 | | | | | -15 | | | | | |
| TTG | GGT | TGG | GCG | GGG | GCA | CCG | ACC | CAC | GCG | CAA | GTG | CAG | TCG | GTA | GAG | 96 |
| Leu | Gly | Trp | Ala | Gly | Ala | Pro | Thr | His | Ala | Gln | Val | Gln | Ser | Val | Glu | |
| -10 | | | | | -5 | | | | | 1 | | | | | 5 | |
| GTG | ATG | CGG | GAC | AGT | TAT | GGC | GTG | CCG | CAC | GTC | TTT | GCC | GAC | AGC | CAC | 144 |
| Val | Met | Arg | Asp | Ser | Tyr | Gly | Val | Pro | His | Val | Phe | Ala | Asp | Ser | His | |
| | | | 10 | | | | | 15 | | | | | 20 | | | |
| TAT | GGC | TTG | TAT | TAC | GGC | TAT | GGT | TAT | GCG | GTC | GCC | CAA | GAC | CGT | CTG | 192 |
| Tyr | Gly | Leu | Tyr | Tyr | Gly | Tyr | Gly | Tyr | Ala | Val | Ala | Gln | Asp | Arg | Leu | |
| | | | 25 | | | | | 30 | | | | | 35 | | | |
| TTC | CAG | ATG | GAC | ATG | GCG | CGT | CGC | TCC | TTT | GTC | GGC | ACA | ACC | GCC | GCC | 240 |
| Phe | Gln | Met | Asp | Met | Ala | Arg | Arg | Ser | Phe | Val | Gly | Thr | Thr | Ala | Ala | |
| | | 40 | | | | | 45 | | | | | 50 | | | | |
| GTC | TTA | GGC | CCT | GGT | GAG | CAA | GAT | GCC | TAC | GTC | AAG | TAC | GAC | ATG | CAG | 288 |
| Val | Leu | Gly | Pro | Gly | Glu | Gln | Asp | Ala | Tyr | Val | Lys | Tyr | Asp | Met | Gln | |
| 55 | | | | | 60 | | | | | 65 | | | | | 70 | |
| GTG | CGG | CAG | AAC | TTC | ACC | CCG | GCT | TCC | ATA | CAG | CGG | CAG | ATC | GCG | GCC | 336 |
| Val | Arg | Gln | Asn | Phe | Thr | Pro | Ala | Ser | Ile | Gln | Arg | Gln | Ile | Ala | Ala | |
| | | | | 75 | | | | | 80 | | | | | 85 | | |
| TTG | TCC | AAG | GAT | GAG | CGC | GAT | ATT | TTT | CGT | GGC | TAT | GCC | GAT | GGC | TAT | 384 |
| Leu | Ser | Lys | Asp | Glu | Arg | Asp | Ile | Phe | Arg | Gly | Tyr | Ala | Asp | Gly | Tyr | |
| | | | 90 | | | | | 95 | | | | | 100 | | | |
| AAC | GCC | TAT | CTG | GAG | CAG | GTG | CGG | CGT | CGC | CCT | GAG | TTG | CTG | CCC | AAA | 432 |
| Asn | Ala | Tyr | Leu | Glu | Gln | Val | Arg | Arg | Arg | Pro | Glu | Leu | Leu | Pro | Lys | |
| | | 105 | | | | | 110 | | | | | 115 | | | | |
| GAA | TAT | GTG | GAT | TTT | GAT | TTC | CAG | CCC | GAG | CCG | CTG | ACC | GAC | TTT | GAT | 480 |
| Glu | Tyr | Val | Asp | Phe | Asp | Phe | Gln | Pro | Glu | Pro | Leu | Thr | Asp | Phe | Asp | |
| | | 120 | | | | | 125 | | | | | 130 | | | | |
| GTG | GTC | ATG | ATC | TGG | GTG | GGC | TCC | ATG | GCC | AAT | CGC | TTC | TCC | GAC | ACG | 528 |
| Val | Val | Met | Ile | Trp | Val | Gly | Ser | Met | Ala | Asn | Arg | Phe | Ser | Asp | Thr | |
| 135 | | | | | 140 | | | | | 145 | | | | | 150 | |
| AAT | CTG | GAA | GTG | ACG | GCA | CTG | GCC | ATG | CGT | CAG | TCT | CTG | GAG | AAA | CAG | 576 |
| Asn | Leu | Glu | Val | Thr | Ala | Leu | Ala | Met | Arg | Gln | Ser | Leu | Glu | Lys | Gln | |

```
                           155                           160                          165
CAC  GGC  CCG  GAA  CGA  GGC  CGT  GCC  TTG  TTT  GAT  GAG  CTG  CTG  TGG  ATC         624
His  Gly  Pro  Glu  Arg  Gly  Arg  Ala  Leu  Phe  Asp  Glu  Leu  Leu  Trp  Ile
               170                      175                      180

AAT  GAC  ACA  ACA  GCT  CCC  ACT  ACG  GTT  CCG  GCC  CCC  GCT  GCC  GAG  CAC         672
Asn  Asp  Thr  Thr  Ala  Pro  Thr  Thr  Val  Pro  Ala  Pro  Ala  Ala  Glu  His
               185                      190                      195

AAG  CCG  CAG  GCA  CAA  GCA  GGG  ACG  CAG  GAT  CTG  GCT  CAT  GTT  TCC  TCG         720
Lys  Pro  Gln  Ala  Gln  Ala  Gly  Thr  Gln  Asp  Leu  Ala  His  Val  Ser  Ser
     200                      205                      210

CCA  GTA  CTG  GCT  ACC  GAG  CTA  GAG  CGC  CAG  GAC  AAG  CAC  TGG  GGC  GGC         768
Pro  Val  Leu  Ala  Thr  Glu  Leu  Glu  Arg  Gln  Asp  Lys  His  Trp  Gly  Gly
215                      220                      225                      230

CGT  GGC  CCG  GAC  TTC  GCG  CCC  AAG  GCT  AGC  AAC  CTG  TGG  AGC  ACT  CGC         816
Arg  Gly  Pro  Asp  Phe  Ala  Pro  Lys  Ala  Ser  Asn  Leu  Trp  Ser  Thr  Arg
                    235                      240                      245

CCC  GAG  CGA  GTG  CAG  GAG  GGC  TCG  ACC  GTA  CTG  ATC  AAC  GGC  CCA  CAG         864
Pro  Glu  Arg  Val  Gln  Glu  Gly  Ser  Thr  Val  Leu  Ile  Asn  Gly  Pro  Gln
               250                      255                      260

TTT  GGC  TGG  TAC  AAC  CCG  GCC  TAC  ACC  TAT  GGC  ATT  GGC  TTG  CAT  GGC         912
Phe  Gly  Trp  Tyr  Asn  Pro  Ala  Tyr  Thr  Tyr  Gly  Ile  Gly  Leu  His  Gly
               265                      270                      275

GCC  GGC  TTC  GAT  GTG  GTG  GGT  AAT  ACG  CCT  TTT  GCC  TAT  CCG  ATC  GTA         960
Ala  Gly  Phe  Asp  Val  Val  Gly  Asn  Thr  Pro  Phe  Ala  Tyr  Pro  Ile  Val
     280                      285                      290

CTG  TTT  GGC  ACC  AAT  AGC  GAG  ATT  GCC  TGG  GGG  GCG  ACT  GCT  GGC  CCG        1008
Leu  Phe  Gly  Thr  Asn  Ser  Glu  Ile  Ala  Trp  Gly  Ala  Thr  Ala  Gly  Pro
295                      300                      305                      310

CAA  GAT  GTG  GTG  GAC  ATA  TAT  CAG  GAA  AAA  TTG  AAC  CCC  TCG  CGT  GCC        1056
Gln  Asp  Val  Val  Asp  Ile  Tyr  Gln  Glu  Lys  Leu  Asn  Pro  Ser  Arg  Ala
                    315                      320                      325

GAT  CAG  TAC  TGG  TTC  AAC  AAT  GCC  TGG  CGC  ACG  ATG  GAG  CAG  CGC  AAG        1104
Asp  Gln  Tyr  Trp  Phe  Asn  Asn  Ala  Trp  Arg  Thr  Met  Glu  Gln  Arg  Lys
               330                      335                      340

GAA  CGT  ATC  CAG  GTA  CGC  GGT  CAG  GCT  GAT  CGG  GAA  ATG  ACG  ATC  TGG        1152
Glu  Arg  Ile  Gln  Val  Arg  Gly  Gln  Ala  Asp  Arg  Glu  Met  Thr  Ile  Trp
               345                      350                      355

CGC  ACC  GTG  CAC  GGC  CCT  GTG  ATG  CAG  TTT  GAT  TAC  GAT  CAG  GGC  GCG        1200
Arg  Thr  Val  His  Gly  Pro  Val  Met  Gln  Phe  Asp  Tyr  Asp  Gln  Gly  Ala
     360                      365                      370

GCG  TAC  AGC  AAG  AAA  CGC  AGC  TGG  GAT  GGC  TAT  GAG  GTG  CAG  TCC  TTG        1248
Ala  Tyr  Ser  Lys  Lys  Arg  Ser  Trp  Asp  Gly  Tyr  Glu  Val  Gln  Ser  Leu
375                      380                      385                      390

CTA  GCC  TGG  TTG  AAC  GTG  GCC  AAG  GCC  CGC  AAC  TGG  ACG  GAG  TTT  CTG        1296
Leu  Ala  Trp  Leu  Asn  Val  Ala  Lys  Ala  Arg  Asn  Trp  Thr  Glu  Phe  Leu
                    395                      400                      405

GAT  CAA  GCC  AGC  AAG  ATG  GCG  ATT  TCG  ATC  AAC  TGG  TAC  TAC  GCC  GAC        1344
Asp  Gln  Ala  Ser  Lys  Met  Ala  Ile  Ser  Ile  Asn  Trp  Tyr  Tyr  Ala  Asp
               410                      415                      420

AAG  CAC  GGC  AAT  ATT  GGT  TAT  GTC  TCG  CCG  GCC  TTC  CTG  CCC  CAG  CGT        1392
Lys  His  Gly  Asn  Ile  Gly  Tyr  Val  Ser  Pro  Ala  Phe  Leu  Pro  Gln  Arg
     425                      430                      435

CCT  GCC  GAT  CAG  GAC  ATC  CGT  GTC  CCT  GCC  AAG  GGG  GAT  GGC  AGC  ATG        1440
Pro  Ala  Asp  Gln  Asp  Ile  Arg  Val  Pro  Ala  Lys  Gly  Asp  Gly  Ser  Met
               440                      445                      450

GAG  TGG  CTG  GGC  ATC  AAG  AGT  TTC  GAC  GCG  ATT  CCC  AAA  GCC  TAC  AAT        1488
Glu  Trp  Leu  Gly  Ile  Lys  Ser  Phe  Asp  Ala  Ile  Pro  Lys  Ala  Tyr  Asn
455                      460                      465                      470

CCA  CCC  CAG  GGC  TAT  CTG  GTC  AAC  TGG  AAC  AAC  AAG  CCT  GCG  CCG  GAC        1536
```

| | | | | | | | | | | | | | | | | |
|---|---|---|---|---|---|---|---|---|---|---|---|---|---|---|---|---|
| Pro | Pro | Gln | Gly | Tyr 475 | Leu | Val | Asn | Trp 480 | Asn | Asn | Lys | Pro | Ala | Pro 485 | Asp | |
| AAA | ACC | AAT | ACG | GAT | ACT | TAC | TAT | TGG | ACC | TAT | GGC | GAC | CGC | ATG | AAT | 1584 |
| Lys | Thr | Asn | Thr 490 | Asp | Thr | Tyr | Tyr | Trp 495 | Thr | Tyr | Gly | Asp | Arg 500 | Met | Asn | |
| GAA | CTG | GTC | AGT | CAG | TAC | CAG | CAG | AAA | GAC | CTC | TTC | AGT | GTG | CAG | GAG | 1632 |
| Glu | Leu | Val 505 | Ser | Gln | Tyr | Gln | Gln 510 | Lys | Asp | Leu | Phe | Ser 515 | Val | Gln | Glu | |
| ATC | TGG | GAG | TTC | AAT | CAA | AAA | GCC | TCC | TAT | AGC | GAT | GTG | AAC | TGG | CGC | 1680 |
| Ile | Trp 520 | Glu | Phe | Asn | Gln | Lys 525 | Ala | Ser | Tyr | Ser | Asp 530 | Val | Asn | Trp | Arg | |
| TAC | TTC | CGC | CCA | CAT | CTG | GAA | AAG | CTG | GCG | CAA | CAG | CTG | CCG | GCC | GAC | 1728 |
| Tyr 535 | Phe | Arg | Pro | His | Leu 540 | Glu | Lys | Leu | Ala | Gln 545 | Gln | Leu | Pro | Ala | Asp 550 | |
| GAT | AGC | AGC | AAG | GCG | GCG | CTG | ACG | ATG | TTG | CTC | GCC | TGG | GAT | GGA | ATG | 1776 |
| Asp | Ser | Ser | Lys 555 | Ala | Ala | Leu | Thr | Met 560 | Leu | Leu | Ala | Trp | Asp 565 | Gly | Met | |
| GAA | CAG | GAT | CAG | GGA | GGG | CAA | AAT | GCC | GGA | CCG | GCG | CGG | GTG | CTC | TTC | 1824 |
| Glu | Gln | Asp | Gln 570 | Gly | Gly | Gln | Asn | Ala 575 | Gly | Pro | Ala | Arg | Val 580 | Leu | Phe | |
| AAG | ACC | TGG | CTG | GAA | GAA | ATG | TAC | AAG | CAG | GTC | TTG | ATG | CCG | GTG | GTG | 1872 |
| Lys | Thr | Trp 585 | Leu | Glu | Glu | Met | Tyr 590 | Lys | Gln | Val | Leu | Met 595 | Pro | Val | Val | |
| CCT | GAA | TCG | CAT | CGC | GCC | ATG | TAT | AGC | CAG | ACT | GGT | TTT | GCC | ACG | CAG | 1920 |
| Pro | Glu | Ser | His 600 | Arg | Ala | Met | Tyr | Ser 605 | Gln | Thr | Gly | Phe | Ala 610 | Thr | Gln | |
| CAA | GGT | CCC | AAC | CCC | GGT | TCC | ATC | AAC | TTG | AGC | ATG | GGC | ACC | AAG | GTC | 1968 |
| Gln 615 | Gly | Pro | Asn | Pro | Gly 620 | Ser | Ile | Asn | Leu | Ser 625 | Met | Gly | Thr | Lys | Val 630 | |
| TTG | TTG | CGT | GCC | TTG | GTG | CTG | GAA | GCC | CAT | CCC | GAT | CCC | AAG | CGT | GTG | 2016 |
| Leu | Leu | Arg | Ala | Leu 635 | Val | Leu | Glu | Ala | His 640 | Pro | Asp | Pro | Lys | Arg 645 | Val | |
| AAT | GTC | TTT | GGT | GAG | CGT | TCG | TCT | CAG | GAA | ATC | ATG | CAC | ACA | GCT | TTG | 2064 |
| Asn | Val | Phe | Gly 650 | Glu | Arg | Ser | Ser | Gln 655 | Glu | Ile | Met | His | Thr 660 | Ala | Leu | |
| CAA | AAT | GCG | CAG | GCC | CGC | TTG | AGC | CAG | GAG | CAG | GGC | GCT | CAG | ATG | GCG | 2112 |
| Gln | Asn | Ala 665 | Gln | Ala | Arg | Leu | Ser 670 | Gln | Glu | Gln | Gly | Ala 675 | Gln | Met | Ala | |
| CGC | TGG | ACC | ATG | CCG | ACC | TCC | GTG | CAT | CGT | TTC | AGC | GAC | AAG | AAC | TTC | 2160 |
| Arg | Trp 680 | Thr | Met | Pro | Thr | Ser 685 | Val | His | Arg | Phe | Ser 690 | Asp | Lys | Asn | Phe | |
| ACG | GGA | ACC | CCG | CAG | ACG | ATG | CCT | GGC | AAT | ACC | TTT | GCC | TTT | ACC | GGC | 2208 |
| Thr 695 | Gly | Thr | Pro | Gln | Thr 700 | Met | Pro | Gly | Asn | Thr 705 | Phe | Ala | Phe | Thr | Gly 710 | |
| TAT | CAG | AAT | CGA | GGC | ACG | GAA | AAT | AAC | CGC | GTG | GTG | TTT | GAT | GCC | AAG | 2256 |
| Tyr | Gln | Asn | Arg | Gly 715 | Thr | Glu | Asn | Asn | Arg 720 | Val | Val | Phe | Asp | Ala 725 | Lys | |
| GGC | GTG | GAG | TTC | TGC | GAC | GCC | ATG | CCG | CCC | GGC | CAA | AGC | GGT | TTC | ACC | 2304 |
| Gly | Val | Glu | Phe | Cys 730 | Asp | Ala | Met | Pro | Pro 735 | Gly | Gln | Ser | Gly | Phe 740 | Thr | |
| GAC | CGC | AAT | GGA | GTG | CGC | AGC | CCG | CAT | TAT | GAG | GAT | CAG | CTG | AAG | TTG | 2352 |
| Asp | Arg | Asn | Gly 745 | Val | Arg | Ser | Pro 750 | His | Tyr | Glu | Asp | Gln 755 | Leu | Lys | Leu | |
| TAC | GAG | AAC | TTC | GAG | TGC | AAG | ACG | ATG | GAT | GTG | ACG | CAT | GCG | GAC | ATT | 2400 |
| Tyr | Glu | Asn 760 | Phe | Glu | Cys | Lys | Thr 765 | Met | Asp | Val | Thr | His 770 | Ala | Asp | Ile | |
| CGT | CGT | AAT | GCG | CAA | AGC | AGC | ACG | ATG | CTG | TTG | ATT | CAG | CCT | CAG | CCT | 2448 |
| Arg 775 | Arg | Asn | Ala | Gln | Ser 780 | Ser | Thr | Met | Leu | Leu 785 | Ile | Gln | Pro | Gln | Pro 790 | |

TAA                                                                                                                          2451

( 2 ) INFORMATION FOR SEQ ID NO: 4:

( i ) SEQUENCE CHARACTERISTICS:
        ( A ) LENGTH: 816 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 4:

| Met | Gln | Lys | Gly | Leu | Val | Arg | Thr | Gly | Leu | Val | Ala | Ala | Gly | Leu | Ile |
|---|---|---|---|---|---|---|---|---|---|---|---|---|---|---|---|
| -26 | -25 |  |  |  |  | -20 |  |  |  |  | -15 |  |  |  |  |
| Leu | Gly | Trp | Ala | Gly | Ala | Pro | Thr | His | Ala | Gln | Val | Gln | Ser | Val | Glu |
| -10 |  |  |  |  | -5 |  |  |  |  | 1 |  |  |  |  | 5 |
| Val | Met | Arg | Asp | Ser | Tyr | Gly | Val | Pro | His | Val | Phe | Ala | Asp | Ser | His |
|  |  |  | 10 |  |  |  |  | 15 |  |  |  |  | 20 |  |  |
| Tyr | Gly | Leu | Tyr | Tyr | Gly | Tyr | Gly | Tyr | Ala | Val | Ala | Gln | Asp | Arg | Leu |
|  |  | 25 |  |  |  |  | 30 |  |  |  |  | 35 |  |  |  |
| Phe | Gln | Met | Asp | Met | Ala | Arg | Arg | Ser | Phe | Val | Gly | Thr | Thr | Ala | Ala |
|  | 40 |  |  |  |  | 45 |  |  |  |  | 50 |  |  |  |  |
| Val | Leu | Gly | Pro | Gly | Glu | Gln | Asp | Ala | Tyr | Val | Lys | Tyr | Asp | Met | Gln |
| 55 |  |  |  |  | 60 |  |  |  |  | 65 |  |  |  |  | 70 |
| Val | Arg | Gln | Asn | Phe | Thr | Pro | Ala | Ser | Ile | Gln | Arg | Gln | Ile | Ala | Ala |
|  |  |  |  | 75 |  |  |  |  | 80 |  |  |  |  | 85 |  |
| Leu | Ser | Lys | Asp | Glu | Arg | Asp | Ile | Phe | Arg | Gly | Tyr | Ala | Asp | Gly | Tyr |
|  |  |  | 90 |  |  |  |  | 95 |  |  |  |  | 100 |  |  |
| Asn | Ala | Tyr | Leu | Glu | Gln | Val | Arg | Arg | Pro | Glu | Leu | Leu | Pro | Lys |  |
|  |  |  | 105 |  |  |  |  | 110 |  |  |  |  | 115 |  |  |
| Glu | Tyr | Val | Asp | Phe | Asp | Phe | Gln | Pro | Glu | Pro | Leu | Thr | Asp | Phe | Asp |
|  | 120 |  |  |  |  | 125 |  |  |  |  | 130 |  |  |  |  |
| Val | Val | Met | Ile | Trp | Val | Gly | Ser | Met | Ala | Asn | Arg | Phe | Ser | Asp | Thr |
| 135 |  |  |  |  | 140 |  |  |  |  | 145 |  |  |  |  | 150 |
| Asn | Leu | Glu | Val | Thr | Ala | Leu | Ala | Met | Arg | Gln | Ser | Leu | Glu | Lys | Gln |
|  |  |  |  | 155 |  |  |  |  | 160 |  |  |  |  | 165 |  |
| His | Gly | Pro | Glu | Arg | Gly | Arg | Ala | Leu | Phe | Asp | Glu | Leu | Leu | Trp | Ile |
|  |  |  | 170 |  |  |  |  | 175 |  |  |  |  | 180 |  |  |
| Asn | Asp | Thr | Thr | Ala | Pro | Thr | Thr | Val | Pro | Ala | Pro | Ala | Ala | Glu | His |
|  |  |  | 185 |  |  |  |  | 190 |  |  |  |  | 195 |  |  |
| Lys | Pro | Gln | Ala | Gln | Ala | Gly | Thr | Gln | Asp | Leu | Ala | His | Val | Ser | Ser |
|  | 200 |  |  |  |  | 205 |  |  |  |  | 210 |  |  |  |  |
| Pro | Val | Leu | Ala | Thr | Glu | Leu | Glu | Arg | Gln | Asp | Lys | His | Trp | Gly | Gly |
| 215 |  |  |  |  | 220 |  |  |  |  | 225 |  |  |  |  | 230 |
| Arg | Gly | Pro | Asp | Phe | Ala | Pro | Lys | Ala | Ser | Asn | Leu | Trp | Ser | Thr | Arg |
|  |  |  |  | 235 |  |  |  |  | 240 |  |  |  |  | 245 |  |
| Pro | Glu | Arg | Val | Gln | Glu | Gly | Ser | Thr | Val | Leu | Ile | Asn | Gly | Pro | Gln |
|  |  |  | 250 |  |  |  |  | 255 |  |  |  |  | 260 |  |  |
| Phe | Gly | Trp | Tyr | Asn | Pro | Ala | Tyr | Thr | Tyr | Gly | Ile | Gly | Leu | His | Gly |
|  |  | 265 |  |  |  |  | 270 |  |  |  |  | 275 |  |  |  |
| Ala | Gly | Phe | Asp | Val | Val | Gly | Asn | Thr | Pro | Phe | Ala | Tyr | Pro | Ile | Val |
|  | 280 |  |  |  |  | 285 |  |  |  |  | 290 |  |  |  |  |
| Leu | Phe | Gly | Thr | Asn | Ser | Glu | Ile | Ala | Trp | Gly | Ala | Thr | Ala | Gly | Pro |
| 295 |  |  |  |  | 300 |  |  |  |  | 305 |  |  |  |  | 310 |
| Gln | Asp | Val | Val | Asp | Ile | Tyr | Gln | Glu | Lys | Leu | Asn | Pro | Ser | Arg | Ala |
|  |  |  |  | 315 |  |  |  |  | 320 |  |  |  |  | 325 |  |

-continued

| | | | | | | | | | | | | | | | |
|---|---|---|---|---|---|---|---|---|---|---|---|---|---|---|---|
|Asp|Gln|Tyr|Trp 330|Phe|Asn|Asn|Ala|Trp 335|Arg|Thr|Met|Glu 340|Gln|Arg|Lys|
|Glu|Arg|Ile 345|Gln|Val|Arg|Gly|Gln 350|Ala|Asp|Arg|Glu|Met 355|Thr|Ile|Trp|
|Arg|Thr 360|Val|His|Gly|Pro|Val 365|Met|Gln|Phe|Asp|Tyr 370|Asp|Gln|Gly|Ala|
|Ala 375|Tyr|Ser|Lys|Lys|Arg 380|Ser|Trp|Asp|Gly|Tyr 385|Glu|Val|Gln|Ser|Leu 390|
|Leu|Ala|Trp|Leu|Asn 395|Val|Ala|Lys|Ala|Arg 400|Asn|Trp|Thr|Glu|Phe 405|Leu|
|Asp|Gln|Ala|Ser 410|Lys|Met|Ala|Ile|Ser 415|Ile|Asn|Trp|Tyr|Tyr 420|Ala|Asp|
|Lys|His|Gly 425|Asn|Ile|Gly|Tyr|Val 430|Ser|Pro|Ala|Phe|Leu 435|Pro|Gln|Arg|
|Pro|Ala 440|Asp|Gln|Asp|Ile|Arg 445|Val|Pro|Ala|Lys|Gly 450|Asp|Gly|Ser|Met|
|Glu 455|Trp|Leu|Gly|Ile|Lys 460|Ser|Phe|Asp|Ala|Ile 465|Pro|Lys|Ala|Tyr|Asn 470|
|Pro|Pro|Gln|Gly|Tyr 475|Leu|Val|Asn|Trp|Asn 480|Asn|Lys|Pro|Ala|Pro 485|Asp|
|Lys|Thr|Asn|Thr 490|Asp|Thr|Tyr|Tyr|Trp 495|Thr|Tyr|Gly|Asp|Arg 500|Met|Asn|
|Glu|Leu|Val|Ser 505|Gln|Tyr|Gln|Gln 510|Lys|Asp|Leu|Phe|Ser 515|Val|Gln|Glu|
|Ile|Trp 520|Glu|Phe|Asn|Gln|Lys 525|Ala|Ser|Tyr|Ser|Asp 530|Val|Asn|Trp|Arg|
|Tyr 535|Phe|Arg|Pro|His|Leu 540|Glu|Lys|Leu|Ala|Gln 545|Gln|Leu|Pro|Ala|Asp 550|
|Asp|Ser|Ser|Lys|Ala 555|Ala|Leu|Thr|Met|Leu 560|Leu|Ala|Trp|Asp|Gly 565|Met|
|Glu|Gln|Asp|Gln 570|Gly|Gly|Gln|Asn|Ala 575|Gly|Pro|Ala|Arg|Val 580|Leu|Phe|
|Lys|Thr|Trp|Leu 585|Glu|Glu|Met|Tyr 590|Lys|Gln|Val|Leu|Met 595|Pro|Val|Val|
|Pro|Glu|Ser 600|His|Arg|Ala|Met|Tyr 605|Ser|Gln|Thr|Gly|Phe 610|Ala|Thr|Gln|
|Gln 615|Gly|Pro|Asn|Pro|Gly 620|Ser|Ile|Asn|Leu|Ser 625|Met|Gly|Thr|Lys|Val 630|
|Leu|Leu|Arg|Ala|Leu 635|Val|Leu|Glu|Ala|His 640|Pro|Asp|Pro|Lys|Arg 645|Val|
|Asn|Val|Phe|Gly 650|Glu|Arg|Ser|Ser|Gln 655|Glu|Ile|Met|His|Thr 660|Ala|Leu|
|Gln|Asn|Ala 665|Gln|Ala|Arg|Leu|Ser 670|Gln|Glu|Gln|Gly|Ala 675|Gln|Met|Ala|
|Arg|Trp 680|Thr|Met|Pro|Thr|Ser 685|Val|His|Arg|Phe|Ser 690|Asp|Lys|Asn|Phe|
|Thr 695|Gly|Thr|Pro|Gln|Thr 700|Met|Pro|Gly|Asn|Thr 705|Phe|Ala|Phe|Thr|Gly 710|
|Tyr|Gln|Asn|Arg|Gly 715|Thr|Glu|Asn|Asn|Arg 720|Val|Val|Phe|Asp|Ala 725|Lys|
|Gly|Val|Glu|Phe 730|Cys|Asp|Ala|Met|Pro 735|Pro|Gly|Gln|Ser|Gly 740|Phe|Thr|

```
Asp  Arg  Asn  Gly  Val  Arg  Ser  Pro  His  Tyr  Glu  Asp  Gln  Leu  Lys  Leu
          745                      750                     755

Tyr  Glu  Asn  Phe  Glu  Cys  Lys  Thr  Met  Asp  Val  Thr  His  Ala  Asp  Ile
     760                      765                     770

Arg  Arg  Asn  Ala  Gln  Ser  Ser  Thr  Met  Leu  Leu  Ile  Gln  Pro  Gln  Pro
775                      780                     785                     790
```

( 2 ) INFORMATION FOR SEQ ID NO: 5:

( i ) SEQUENCE CHARACTERISTICS:
        ( A ) LENGTH: 846 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: Escherichia coli ( x ) PUBLICATION INFORMATION:
        ( A ) AUTHORS: Schumacher, G
                Sizmann, D
                Haug, H
                Buckel, P
                Bock, A
        ( B ) TITLE: Penicillin acylase from E.coli: unique
               gene-protein realtion.
        ( C ) JOURNAL: Nucleic Acids Res.
        ( D ) VOLUME: 14
        ( F ) PAGES: 5713-5727
        ( G ) DATE: 1986

( x i ) SEQUENCE DESCRIPTION: SEQ ID NO: 5:

```
Met  Lys  Asn  Arg  Asn  Arg  Met  Ile  Val  Asn  Cys  Val  Thr  Ala  Ser  Leu
1                    5                     10                          15

Met  Tyr  Tyr  Trp  Ser  Leu  Pro  Ala  Leu  Ala  Glu  Gln  Ser  Ser  Ser  Glu
               20                    25                     30

Ile  Lys  Ile  Val  Arg  Asp  Glu  Tyr  Gly  Met  Pro  His  Ile  Tyr  Ala  Asn
          35                    40                     45

Asp  Thr  Trp  His  Leu  Phe  Tyr  Gly  Tyr  Gly  Tyr  Val  Ala  Gln  Asp
     50                    55                     60

Arg  Leu  Phe  Gln  Met  Glu  Met  Ala  Arg  Arg  Ser  Thr  Gln  Gly  Thr  Val
65                        70                    75                          80

Ala  Glu  Val  Leu  Gly  Lys  Asp  Phe  Val  Lys  Phe  Asp  Lys  Asp  Ile  Arg
               85                    90                     95

Arg  Asn  Tyr  Trp  Pro  Asp  Ala  Ile  Arg  Ala  Gln  Ile  Ala  Ala  Leu  Ser
               100                   105                    110

Pro  Glu  Asp  Met  Ser  Ile  Leu  Gln  Gly  Tyr  Ala  Asp  Gly  Met  Asn  Ala
          115                   120                    125

Trp  Ile  Asp  Lys  Val  Asn  Thr  Asn  Pro  Glu  Thr  Leu  Leu  Pro  Lys  Gln
     130                   135                    140

Phe  Asn  Thr  Phe  Gly  Phe  Thr  Pro  Lys  Arg  Trp  Glu  Pro  Phe  Asp  Val
145                       150                   155                         160

Ala  Met  Ile  Phe  Val  Gly  Thr  Met  Ala  Asn  Arg  Phe  Ser  Asp  Ser  Thr
               165                   170                    175

Ser  Glu  Ile  Asp  Asn  Leu  Ala  Leu  Leu  Thr  Ala  Leu  Lys  Asp  Lys  Tyr
          180                   185                    190

Gly  Val  Ser  Gln  Gly  Met  Ala  Val  Phe  Asn  Gln  Leu  Lys  Trp  Leu  Val
          195                   200                    205

Asn  Pro  Ser  Ala  Pro  Thr  Thr  Ile  Ala  Val  Gln  Glu  Ser  Asn  Tyr  Pro
     210                   215                    220
```

| | | | | | | | | | | | | | | |
|---|---|---|---|---|---|---|---|---|---|---|---|---|---|---|
| Leu 225 | Lys | Phe | Asn | Gln 230 | Gln | Asn | Ser | Gln | Thr 235 | Ala | Ala | Leu | Leu | Pro | Arg 240 |
| Tyr | Asp | Leu | Pro | Ala 245 | Pro | Met | Leu | Asp | Arg 250 | Pro | Ala | Lys | Gly 255 | Ala | Asp |
| Gly | Ala | Leu | Leu 260 | Ala | Leu | Thr | Ala | Gly 265 | Lys | Asn | Arg | Glu | Thr 270 | Ile | Val |
| Ala | Gln | Phe 275 | Ala | Gln | Gly | Gly | Ala 280 | Asn | Gly | Leu | Ala | Gly 285 | Tyr | Pro | Thr |
| Thr | Ser 290 | Asn | Met | Trp | Val | Ile 295 | Gly | Lys | Ser | Lys | Ala 300 | Gln | Asp | Ala | Lys |
| Ala 305 | Ile | Met | Val | Asn | Gly 310 | Pro | Gln | Phe | Gly | Trp 315 | Tyr | Ala | Pro | Ala | Tyr 320 |
| Thr | Tyr | Gly | Ile | Gly 325 | Leu | His | Gly | Ala | Gly 330 | Tyr | Asp | Val | Thr | Gly 335 | Asn |
| Thr | Pro | Phe | Ala 340 | Tyr | Pro | Gly | Leu | Val 345 | Phe | Gly | His | Asn | Gly 350 | Val | Ile |
| Ser | Trp | Gly 355 | Ser | Thr | Ala | Gly | Phe 360 | Gly | Asp | Asp | Val | Asp 365 | Ile | Phe | Ala |
| Glu | Arg 370 | Leu | Ser | Ala | Glu | Lys 375 | Pro | Gly | Tyr | Tyr | Leu 380 | His | Asn | Gly | Lys |
| Trp 385 | Val | Lys | Met | Leu | Ser 390 | Arg | Glu | Glu | Thr | Ile 395 | Thr | Val | Lys | Asn | Gly 400 |
| Gln | Ala | Glu | Thr | Phe 405 | Thr | Val | Trp | Arg | Thr 410 | Val | His | Gly | Asn | Ile 415 | Leu |
| Gln | Thr | Asp | Gln 420 | Thr | Thr | Gln | Thr | Ala 425 | Tyr | Ala | Lys | Ser | Arg 430 | Ala | Trp |
| Asp | Gly | Lys 435 | Glu | Val | Ala | Ser | Leu 440 | Leu | Ala | Trp | Thr | His 445 | Gln | Met | Lys |
| Ala | Lys 450 | Asn | Trp | Gln | Glu | Trp 455 | Thr | Gln | Gln | Ala | Ala 460 | Lys | Gln | Ala | Leu |
| Thr 465 | Ile | Asn | Trp | Tyr | Tyr 470 | Ala | Asp | Val | Asn | Gly 475 | Asn | Ile | Gly | Tyr | Val 480 |
| His | Thr | Gly | Ala | Tyr 485 | Pro | Asp | Arg | Gln | Ser 490 | Gly | His | Asp | Pro | Arg 495 | Leu |
| Pro | Val | Pro | Gly 500 | Thr | Gly | Lys | Trp | Asp 505 | Trp | Lys | Gly | Leu | Leu 510 | Pro | Phe |
| Glu | Met | Asn | Pro | Lys 515 | Val | Tyr | Asn | Pro | Gln 520 | Ser | Gly | Tyr | Ile 525 | Ala | Asn |
| Trp | Asn | Asn 530 | Ser | Pro | Gln | Lys | Asp 535 | Tyr | Pro | Ala | Ser | Asp 540 | Leu | Phe | Ala |
| Phe 545 | Leu | Trp | Gly | Gly | Ala 550 | Asp | Arg | Val | Thr | Glu 555 | Ile | Asp | Arg | Leu | Leu 560 |
| Glu | Gln | Lys | Pro | Arg 565 | Leu | Thr | Ala | Asp | Gln 570 | Ala | Trp | Asp | Val | Ile 575 | Arg |
| Gln | Thr | Ser | Arg 580 | Gln | Asp | Leu | Asn | Leu 585 | Arg | Leu | Phe | Leu | Pro 590 | Thr | Leu |
| Gln | Ala | Ala | Thr 595 | Ser | Gly | Leu | Thr | Gln 600 | Ser | Asp | Pro | Arg | Arg 605 | Gln | Leu |
| Val | Glu 610 | Thr | Leu | Thr | Arg | Trp 615 | Asp | Gly | Ile | Asn | Leu 620 | Leu | Asn | Asp | Asp |
| Gly 625 | Lys | Thr | Trp | Gln | Gln 630 | Pro | Gly | Ser | Ala | Ile 635 | Leu | Asn | Val | Trp | Leu 640 |
| Thr | Ser | Met | Leu | Lys | Arg | Thr | Val | Val | Ala | Ala | Val | Pro | Met | Pro | Phe |

|   |   |   |   |   |   |   | 645 |   |   |   | 650 |   |   |   | 655 |   |
|---|---|---|---|---|---|---|---|---|---|---|---|---|---|---|---|---|
| Asp | Lys | Trp | Tyr 660 | Ser | Ala | Ser | Gly | Tyr 665 | Glu | Thr | Thr | Gln | Asp 670 | Gly | Pro |
| Thr | Gly | Ser 675 | Leu | Asn | Ile | Ser | Val 680 | Gly | Ala | Lys | Ile | Leu 685 | Tyr | Glu | Ala |
| Val | Gln 690 | Gly | Asp | Lys | Ser | Pro 695 | Ile | Pro | Gln | Ala | Val 700 | Asp | Leu | Phe | Ala |
| Gly 705 | Lys | Pro | Gln | Gln | Glu 710 | Val | Val | Leu | Ala | Ala 715 | Leu | Glu | Asp | Thr | Trp 720 |
| Glu | Thr | Leu | Ser | Lys 725 | Arg | Tyr | Gly | Asn | Asn 730 | Val | Ser | Asn | Trp | Lys 735 | Thr |
| Pro | Ala | Met | Ala 740 | Leu | Thr | Phe | Arg | Ala 745 | Asn | Asn | Phe | Phe | Gly 750 | Val | Pro |
| Gln | Ala | Ala 755 | Ala | Glu | Glu | Thr | Arg 760 | His | Gln | Ala | Glu | Tyr 765 | Gln | Asn | Arg |
| Gly | Thr 770 | Glu | Asn | Asp | Met | Ile 775 | Val | Phe | Ser | Pro | Thr 780 | Thr | Ser | Asp | Arg |
| Pro 785 | Val | Leu | Ala | Trp | Asp 790 | Val | Val | Ala | Pro | Gly 795 | Gln | Ser | Gly | Phe | Ile 800 |
| Ala | Pro | Asp | Gly | Thr 805 | Val | Asp | Lys | His | Tyr 810 | Glu | Asp | Gln | Leu | Lys 815 | Met |
| Tyr | Glu | Asn | Phe 820 | Gly | Arg | Lys | Ser | Leu 825 | Trp | Leu | Thr | Lys | Gln 830 | Asp | Val |
| Glu | Ala | His 835 | Lys | Glu | Ser | Gln | Glu 840 | Val | Leu | His | Val | Gln 845 | Arg |   |   |

( 2 ) INFORMATION FOR SEQ ID NO: 6:

( i ) SEQUENCE CHARACTERISTICS:
        ( A ) LENGTH: 844 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Kluyvera citrophila
        ( B ) STRAIN: ATCC 21285

( x i ) SEQUENCE DESCRIPTION: SEQ ID NO: 6:

| Met 1 | Lys | Asn | Arg | Asn 5 | Arg | Met | Ile | Val | Asn 10 | Gly | Ile | Val | Thr | Ser 15 | Leu |
|---|---|---|---|---|---|---|---|---|---|---|---|---|---|---|---|
| Ile | Cys | Cys | Ser 20 | Ser | Leu | Ser | Ala | Leu 25 | Ala | Ala | Ser | Pro | Pro 30 | Thr | Glu |
| Val | Lys | Ile 35 | Val | Arg | Asp | Glu | Tyr 40 | Gly | Met | Pro | His | Ile 45 | Tyr | Ala | Asp |
| Asp | Thr 50 | Tyr | Arg | Leu | Phe | Tyr 55 | Gly | Tyr | Gly | Tyr | Val 60 | Val | Ala | Gln | Asp |
| Arg 65 | Leu | Phe | Gln | Met | Glu 70 | Met | Ala | Arg | Arg | Ser 75 | Thr | Gln | Gly | Thr | Val 80 |
| Ser | Glu | Val | Leu | Gly 85 | Lys | Ala | Phe | Val | Ser 90 | Phe | Asp | Lys | Asp | Ile 95 | Arg |
| Gln | Asn | Tyr | Trp 100 | Pro | Asp | Ser | Ile | Arg 105 | Ala | Gln | Ile | Ala | Ser 110 | Leu | Ser |
| Ala | Glu | Asp 115 | Lys | Ser | Ile | Leu | Gln 120 | Gly | Tyr | Ala | Asp | Gly 125 | Met | Asn | Ala |

| | | | | | | | | | | | | | | |
|---|---|---|---|---|---|---|---|---|---|---|---|---|---|---|
| Trp | Ile | Asp | Lys | Val | Asn | Ala | Ser | Pro | Asp | Lys | Leu | Leu | Pro | Gln | Gln |
| | 130 | | | | 135 | | | | 140 | | | | | | |
| Phe | Ser | Thr | Phe | Gly | Phe | Lys | Pro | Lys | His | Trp | Glu | Pro | Phe | Asp | Val |
| 145 | | | | | 150 | | | | 155 | | | | | | 160 |
| Ala | Met | Ile | Phe | Val | Gly | Thr | Met | Ala | Asn | Arg | Phe | Ser | Asp | Ser | Thr |
| | | | | 165 | | | | | 170 | | | | | 175 | |
| Ser | Glu | Ile | Asp | Asn | Leu | Ala | Leu | Leu | Thr | Ala | Val | Lys | Asp | Lys | Tyr |
| | | | 180 | | | | | 185 | | | | | 190 | | |
| Gly | Asn | Asp | Glu | Gly | Met | Ala | Val | Phe | Asn | Gln | Leu | Lys | Trp | Leu | Val |
| | | 195 | | | | | 200 | | | | | 205 | | | |
| Asn | Pro | Ser | Ala | Pro | Thr | Thr | Ile | Ala | Ala | Arg | Glu | Ser | Ser | Tyr | Pro |
| | 210 | | | | | 215 | | | | | 220 | | | | |
| Leu | Lys | Phe | Asp | Leu | Gln | Asn | Thr | Gln | Thr | Ala | Ala | Leu | Leu | Val | Pro |
| 225 | | | | | 230 | | | | | 235 | | | | | 240 |
| Arg | Tyr | Asp | Gln | Pro | Ala | Pro | Met | Leu | Asp | Arg | Pro | Ala | Lys | Gly | Thr |
| | | | | 245 | | | | | 250 | | | | | 255 | |
| Asp | Gly | Ala | Leu | Leu | Ala | Val | Thr | Ala | Ile | Lys | Asn | Arg | Glu | Thr | Ile |
| | | | 260 | | | | | 265 | | | | | 270 | | |
| Ala | Ala | Gln | Phe | Ala | Asn | Gly | Ala | Asn | Gly | Leu | Ala | Gly | Tyr | Pro | Thr |
| | | 275 | | | | | 280 | | | | | 285 | | | |
| Thr | Ser | Asn | Met | Trp | Val | Ile | Gly | Lys | Asn | Lys | Ala | Gln | Asp | Ala | Lys |
| | 290 | | | | | 295 | | | | | 300 | | | | |
| Ala | Ile | Met | Val | Asn | Gly | Pro | Gln | Phe | Gly | Trp | Tyr | Ala | Pro | Ala | Tyr |
| 305 | | | | | 310 | | | | | 315 | | | | | 320 |
| Thr | Tyr | Gly | Ile | Gly | Leu | His | Gly | Ala | Gly | Tyr | Asp | Val | Thr | Gly | Asn |
| | | | | 325 | | | | | 330 | | | | | 335 | |
| Thr | Pro | Phe | Ala | Tyr | Pro | Gly | Leu | Val | Phe | Gly | His | Asn | Gly | Thr | Ile |
| | | | 340 | | | | | 345 | | | | | 350 | | |
| Ser | Trp | Gly | Ser | Thr | Ala | Gly | Phe | Gly | Asp | Asp | Val | Asp | Ile | Phe | Ala |
| | | 355 | | | | | 360 | | | | | 365 | | | |
| Glu | Lys | Leu | Ser | Ala | Glu | Lys | Pro | Gly | Tyr | Tyr | Gln | His | Asn | Gly | Glu |
| | 370 | | | | | 375 | | | | | 380 | | | | |
| Trp | Val | Lys | Met | Leu | Ser | Arg | Lys | Glu | Thr | Ile | Ala | Val | Lys | Asp | Gly |
| 385 | | | | | 390 | | | | | 395 | | | | | 400 |
| Gln | Pro | Glu | Thr | Phe | Thr | Val | Trp | Arg | Thr | Leu | Asp | Gly | Asn | Val | Ile |
| | | | | 405 | | | | | 410 | | | | | 415 | |
| Lys | Thr | Asp | Thr | Arg | Thr | Gln | Thr | Ala | Tyr | Ala | Lys | Ala | Arg | Ala | Trp |
| | | | 420 | | | | | 425 | | | | | 430 | | |
| Ala | Gly | Lys | Glu | Val | Ala | Ser | Leu | Leu | Ala | Trp | Thr | His | Gln | Met | Lys |
| | | 435 | | | | | 440 | | | | | 445 | | | |
| Ala | Lys | Asn | Trp | Pro | Glu | Trp | Thr | Gln | Gln | Ala | Ala | Lys | Gln | Ala | Leu |
| | 450 | | | | | 455 | | | | | 460 | | | | |
| Thr | Ile | Asn | Trp | Tyr | Tyr | Ala | Asp | Val | Asn | Gly | Asn | Ile | Gly | Tyr | Val |
| 465 | | | | | 470 | | | | 475 | | | | | | 480 |
| His | Thr | Gly | Ala | Tyr | Pro | Asp | Arg | Gln | Pro | Gly | His | Asp | Pro | Arg | Leu |
| | | | | 485 | | | | | 490 | | | | | 495 | |
| Pro | Val | Pro | Asp | Gly | Lys | Trp | Asp | Trp | Lys | Gly | Leu | Leu | Ser | Phe | Asp |
| | | | 500 | | | | | 505 | | | | | 510 | | |
| Leu | Asn | Pro | Lys | Val | Tyr | Asn | Pro | Gln | Ser | Gly | Tyr | Ile | Ala | Asn | Trp |
| | | 515 | | | | | 520 | | | | | 525 | | | |
| Asn | Asn | Ser | Pro | Gln | Lys | Asp | Tyr | Pro | Ala | Ser | Asp | Leu | Phe | Ala | Phe |
| | 530 | | | | | 535 | | | | | 540 | | | | |

-continued

```
Leu  Trp  Gly  Gly  Ala  Asp  Arg  Val  Thr  Glu  Ile  Asp  Thr  Ile  Leu  Asp
545                 550                 555                 560

Lys  Gln  Pro  Arg  Phe  Thr  Ala  Asp  Gln  Ala  Trp  Asp  Val  Ile  Arg  Gln
                565                 570                 575

Thr  Ser  Leu  Arg  Asp  Leu  Leu  Arg  Leu  Phe  Leu  Pro  Ala  Leu  Lys  Asp
               580                 585                 590

Ala  Thr  Ala  Asn  Leu  Ala  Glu  Asn  Asp  Pro  Arg  Arg  Gln  Leu  Val  Asp
          595                 600                 605

Lys  Leu  Ala  Ser  Trp  Asp  Gly  Glu  Asn  Leu  Val  Asn  Asp  Asp  Gly  Lys
          610                 615                 620

Thr  Tyr  Gln  Gln  Pro  Gly  Ser  Ala  Ile  Leu  Asn  Ala  Trp  Leu  Thr  Ser
625                 630                 635                 640

Met  Leu  Lys  Arg  Thr  Val  Val  Ala  Ala  Val  Pro  Ala  Pro  Phe  Gly  Lys
               645                 650                 655

Trp  Tyr  Ser  Ala  Ser  Gly  Tyr  Glu  Thr  Thr  Gln  Asp  Gly  Pro  Thr  Gly
               660                 665                 670

Ser  Leu  Asn  Ile  Ser  Val  Gly  Ala  Lys  Ile  Leu  Tyr  Glu  Ala  Leu  Gln
               675                 680                 685

Gly  Asp  Lys  Ser  Pro  Ile  Pro  Gln  Ala  Val  Asp  Leu  Phe  Gly  Gly  Lys
     690                 695                 700

Pro  Glu  Gln  Glu  Val  Ile  Leu  Ala  Ala  Leu  Asp  Asp  Ala  Trp  Glu  Thr
705                 710                 715                 720

Leu  Ser  Lys  Arg  Tyr  Gly  Asn  Asp  Val  Thr  Gly  Trp  Lys  Thr  Pro  Ala
               725                 730                 735

Met  Ala  Leu  Thr  Phe  Arg  Ala  Asn  Asn  Phe  Phe  Gly  Val  Pro  Gln  Ala
               740                 745                 750

Ala  Ala  Lys  Glu  Ala  Arg  His  Gln  Ala  Glu  Tyr  Gln  Asn  Arg  Gly  Thr
          755                 760                 765

Glu  Asn  Asp  Met  Ile  Val  Phe  Ser  Pro  Thr  Ser  Gly  Asn  Arg  Pro  Val
          770                 775                 780

Leu  Ala  Trp  Asp  Val  Val  Ala  Pro  Gly  Gln  Ser  Gly  Phe  Ile  Ala  Pro
785                 790                 795                 800

Asp  Gly  Lys  Ala  Asp  Lys  His  Tyr  Asp  Asp  Gln  Leu  Lys  Met  Tyr  Glu
               805                 810                 815

Ser  Phe  Gly  Arg  Lys  Ser  Leu  Trp  Leu  Thr  Pro  Gln  Asp  Val  Asp  Glu
               820                 825                 830

His  Lys  Glu  Ser  Gln  Glu  Val  Leu  Gln  Val  Gln  Arg
               835                 840
```

( 2 ) INFORMATION FOR SEQ ID NO: 7:

( i ) SEQUENCE CHARACTERISTICS:
        ( A ) LENGTH: 774 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Pseudomonas species
        ( B ) STRAIN: SE83

( x i ) SEQUENCE DESCRIPTION: SEQ ID NO: 7:

```
Met  Thr  Met  Ala  Ala  Lys  Thr  Asp  Arg  Glu  Ala  Leu  Gln  Ala  Ala  Leu
1                   5                   10                  15

Pro  Pro  Leu  Ser  Gly  Ser  Leu  Ser  Ile  Pro  Gly  Leu  Ser  Ala  Pro  Val
```

|  | 20 | 25 | 30 |
|---|---|---|---|

Arg Val Gln Arg Asp Gly Trp Gly Ile Pro His Ile Lys Ala Ser Gly
            35              40              45

Glu Ala Asp Ala Tyr Arg Ala Leu Gly Phe Val His Ala Gln Asp Arg
        50              55              60

Leu Phe Gln Met Glu Leu Thr Arg Arg Lys Ala Leu Gly Arg Ala Ala
65              70              75              80

Glu Trp Leu Gly Ala Glu Ala Ala Glu Ala Asp Ile Leu Val Arg Arg
                85              90              95

Leu Gly Met Glu Lys Val Cys Arg Arg Asp Phe Glu Ala Leu Gly Ala
            100             105             110

Glu Ala Lys Asp Met Leu Arg Ala Tyr Val Ala Gly Val Asn Ala Phe
        115             120             125

Leu Ala Ser Gly Ala Pro Leu Pro Ile Glu Tyr Gly Leu Leu Gly Ala
130             135             140

Glu Pro Glu Pro Trp Glu Pro Trp His Ser Ile Ala Val Met Arg Arg
145             150             155             160

Leu Gly Leu Leu Met Gly Ser Val Trp Phe Lys Leu Trp Arg Met Leu
            165             170             175

Ala Leu Pro Val Val Gly Ala Ala Asn Ala Leu Lys Leu Arg Tyr Asp
        180             185             190

Asp Gly Gly Gln Asp Leu Leu Cys Ile Pro Pro Gly Val Glu Ala Glu
        195             200             205

Arg Leu Glu Ala Asp Leu Ala Ala Leu Arg Pro Ala Val Asp Ala Leu
210             215             220

Leu Lys Ala Met Gly Gly Asp Ala Ser Asp Ala Ala Gly Gly Gly Ser
225             230             235             240

Asn Asn Trp Ala Val Ala Pro Gly Arg Thr Ala Thr Gly Arg Pro Ile
            245             250             255

Leu Ala Gly Asp Pro His Arg Val Phe Glu Ile Pro Gly Met Tyr Ala
        260             265             270

Gln His His Leu Ala Cys Asp Arg Phe Asp Met Ile Gly Leu Thr Val
    275             280             285

Pro Gly Val Pro Gly Phe Pro His Phe Ala His Asn Gly Lys Val Ala
290             295             300

Tyr Cys Val Thr His Ala Phe Met Asp Ile His Asp Leu Tyr Leu Glu
305             310             315             320

Gln Phe Ala Glu Asp Gly Arg Thr Ala Arg Phe Gly Asn Glu Phe Glu
            325             330             335

Pro Val Ala Trp Arg Arg Asp Arg Ile Ala Val Arg Gly Gly Ala Asp
        340             345             350

Arg Glu Phe Asp Ile Val Glu Thr Arg His Gly Pro Val Ile Ala Gly
        355             360             365

Asp Pro Leu Glu Gly Ala Ala Leu Thr Leu Arg Ser Val Gln Phe Ala
370             375             380

Glu Thr Asp Leu Ser Phe Asp Cys Leu Thr Arg Met Pro Gly Ala Ser
385             390             395             400

Thr Val Ala Gln Leu Tyr Asp Ala Thr Arg Gly Trp Gly Leu Ile Asp
            405             410             415

His Asn Leu Val Ala Gly Asp Val Ala Gly Ser Ile Gly His Leu Val
        420             425             430

Arg Ala Arg Val Pro Ser Arg Pro Arg Glu Asn Gly Trp Leu Pro Val
        435             440             445

```
Pro Gly Trp Ser Gly Glu His Glu Trp Arg Gly Trp Ile Pro His Glu
    450                 455                 460
Ala Met Pro Arg Val Ile Asp Pro Pro Gly Gly Leu Ile Val Thr Ala
465                 470                 475                 480
Asn Asn Arg Val Val Ala Asp Asp His Pro Asp Tyr Leu Cys Thr Asp
                485                 490                 495
Cys His Pro Pro Tyr Arg Ala Glu Arg Ile Met Glu Arg Leu Val Ala
            500                 505                 510
Ser Pro Ala Phe Ala Val Asp Asp Ala Ala Ile His Ala Asp Thr
        515                 520                 525
Leu Ser Pro His Val Gly Leu Leu Arg Ala Arg Leu Glu Ala Leu Gly
    530                 535                 540
Ile Gln Gly Ser Leu Pro Ala Glu Glu Leu Arg Gln Thr Leu Ile Ala
545                 550                 555                 560
Trp Asp Gly Arg Met Asp Ala Gly Ser Gln Ala Ala Ser Ala Tyr Asn
                565                 570                 575
Ala Phe Arg Arg Ala Leu Thr Arg Leu Val Thr Ala Arg Ser Gly Leu
            580                 585                 590
Glu Gln Ala Ile Ala His Pro Phe Ala Ala Val Pro Pro Gly Val Ser
        595                 600                 605
Pro Gln Gly Gln Val Trp Trp Ala Val Pro Thr Leu Leu Arg Asn Asp
    610                 615                 620
Asp Ala Gly Met Leu Lys Gly Trp Ser Trp Asp Glu Ala Leu Ser Glu
625                 630                 635                 640
Ala Leu Ser Val Ala Thr Gln Asn Leu Thr Gly Arg Gly Trp Gly Glu
                645                 650                 655
Glu His Arg Pro Arg Phe Thr His Pro Leu Ser Ala Gln Phe Pro Ala
            660                 665                 670
Trp Ala Ala Leu Leu Asn Pro Val Ser Arg Pro Ile Gly Gly Asp Gly
        675                 680                 685
Asp Thr Val Leu Ala Asn Gly Leu Val Pro Ser Ala Gly Pro Glu Ala
    690                 695                 700
Thr Tyr Gly Ala Leu Ser Arg Tyr Val Phe Asp Val Gly Asn Trp Asp
705                 710                 715                 720
Asn Ser Arg Trp Val Val Phe His Gly Ala Ser Gly His Pro Ala Ser
                725                 730                 735
Pro His Tyr Ala Asp Gln Asn Ala Pro Trp Ser Asp Cys Ala Met Val
            740                 745                 750
Pro Met Leu Tyr Ser Trp Asp Arg Ile Ala Ala Glu Ala Val Thr Ser
        755                 760                 765
Gln Glu Leu Val Pro Ala
    770
```

( 2 ) INFORMATION FOR SEQ ID NO: 8:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( x i ) SEQUENCE DESCRIPTION: SEQ ID NO: 8:

TCGTACATTT TCAGCTGATC TTCATAGTGC TTATC                                        35

( 2 ) INFORMATION FOR SEQ ID NO: 9:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i i i ) ANTI-SENSE: NO ( v ) FRAGMENT TYPE: N-terminal ( x i ) SEQUENCE DESCRIPTION: SEQ ID NO: 9:

Ser Asn Leu Trp Ser Xaa Cys Pro Glu Cys Val
    1               5                   10

( 2 ) INFORMATION FOR SEQ ID NO: 10:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( i i i ) ANTI-SENSE: NO ( x i ) SEQUENCE DESCRIPTION: SEQ ID NO: 10:

AGCAACCTGT GGAGCMSCTG CCCGGAGTGC GT                                           32

( 2 ) INFORMATION FOR SEQ ID NO: 11:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( x i ) SEQUENCE DESCRIPTION: SEQ ID NO: 11:

ATGCTGAGAG TTCTGCACCG GGCGGCGTCC GCCTTG                                       36

( 2 ) INFORMATION FOR SEQ ID NO: 12:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( x i ) SEQUENCE DESCRIPTION: SEQ ID NO: 12:

CGGCCGATGC TCCTCGCCCC AGCCGCGCCC GGTCAGGTTC TGCGTCGCGA CGGA                   54

( 2 ) INFORMATION FOR SEQ ID NO: 13:

( i ) SEQUENCE CHARACTERISTICS:
  ( A ) LENGTH: 5 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO: 13:

Glu Gln Ser Ser Ser
1       5

( 2 ) INFORMATION FOR SEQ ID NO: 14:

( i ) SEQUENCE CHARACTERISTICS:
  ( A ) LENGTH: 3 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: NO ( v ) FRAGMENT TYPE: C-terminal ( x i ) SEQUENCE DESCRIPTION: SEQ ID NO: 14:

Gln Thr Ala
1

( 2 ) INFORMATION FOR SEQ ID NO: 15:

( i ) SEQUENCE CHARACTERISTICS:
  ( A ) LENGTH: 3 amino acids
  ( B ) TYPE: amino acid
  ( C ) STRANDEDNESS: single
  ( D ) TOPOLOGY: linear ( i i ) MOLECULE TYPE: protein ( i i i ) HYPOTHETICAL: NO ( v ) FRAGMENT TYPE: N-terminal ( x i ) SEQUENCE DESCRIPTION: SEQ ID NO: 15:

Ser Asn Met
1

( 2 ) INFORMATION FOR SEQ ID NO: 16:

( i ) SEQUENCE CHARACTERISTICS:
  ( A ) LENGTH: 7 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO: 16:

Glu Gln Ser Ser Ser Glu Ile
1       5

( 2 ) INFORMATION FOR SEQ ID NO: 17:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: C-terminal ( x i ) SEQUENCE DESCRIPTION: SEQ ID NO: 17:

Asn  Gln  Gln  Asn  Ser  Gln  Thr  Ala
    1                          5

( 2 ) INFORMATION FOR SEQ ID NO: 18:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO: 18:

Ser  Asn  Met  Trp  Val  Ile  Gly
    1                        5

( 2 ) INFORMATION FOR SEQ ID NO: 19:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO: 19:

Ala  Ser  Pro  Pro  Thr  Glu  Val  Lys
    1                          5

( 2 ) INFORMATION FOR SEQ ID NO: 20:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: C-terminal ( x i ) SEQUENCE DESCRIPTION: SEQ ID NO: 20:

Thr  Gln  Thr  Ala
    1

( 2 ) INFORMATION FOR SEQ ID NO: 21:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO: 21:

Ser  Asn  Met  Trp  Val  Ile  Gly  Lys
    1                          5

( 2 ) INFORMATION FOR SEQ ID NO: 22:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO: 22:

Gln  Xaa  Gln  Xaa  Val  Glu  Val  Met  Xaa  Thr
    1                          5                              10

( 2 ) INFORMATION FOR SEQ ID NO: 23:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO: 23:

Ser  Asn  Leu  Trp  Ser  Thr  Xaa  Pro  Glu  Xaa  Val
    1                          5                              10

( 2 ) INFORMATION FOR SEQ ID NO: 24:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO: 24:

Thr  Met  Ala  Ala  Lys  Thr
    1                          5

( 2 ) INFORMATION FOR SEQ ID NO: 25:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO: 25:

Ser Asn Asn Trp Ala
    1                 5

( 2 ) INFORMATION FOR SEQ ID NO: 26:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO: 26:

Glu Pro Thr Ser Thr Pro Gln Ala
    1                 5

( 2 ) INFORMATION FOR SEQ ID NO: 27:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO: 27:

Ser Asn Ser Xaa Ala Val Ala
    1                 5

( 2 ) INFORMATION FOR SEQ ID NO: 28:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( x i ) SEQUENCE DESCRIPTION: SEQ ID NO: 28:

CAGAACTCTC AGCATATGTT TCCCCTCTCA        30

( 2 ) INFORMATION FOR SEQ ID NO: 29:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( x i ) SEQUENCE DESCRIPTION: SEQ ID NO: 29:

```
AGGTCCAGAC AGCATATGAC GATGGCG                                                27
```

( 2 ) INFORMATION FOR SEQ ID NO: 30:

( i ) SEQUENCE CHARACTERISTICS:
        ( A ) LENGTH: 93 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( x i ) SEQUENCE DESCRIPTION: SEQ ID NO: 30:

```
GCCCTGGCTG CGCGCCTGGG CCCAGCCATA GCCGTAGAAG GCTGAGGGCG CGTCTACGCC           60
GTAGATGTGC GGGACGCCGT AGCCGTCCCA CAG                                        93
```

( 2 ) INFORMATION FOR SEQ ID NO: 31:

( i ) SEQUENCE CHARACTERISTICS:
        ( A ) LENGTH: 84 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( x i ) SEQUENCE DESCRIPTION: SEQ ID NO: 31:

```
CCAGACGGTC GTCTGTTCGT AATCCGGTCC CCAGTATTCG GCCCCCTTGC CCCGCGCTTC           60
TCCATACAGG CGCAGGATAT TGTC                                                  84
```

( 2 ) INFORMATION FOR SEQ ID NO: 32:

( i ) SEQUENCE CHARACTERISTICS:
        ( A ) LENGTH: 84 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( x i ) SEQUENCE DESCRIPTION: SEQ ID NO: 32:

```
GAATGCGTCG AGGTTGGCGC GGAAATCAGG CGACTGCTGC GCATACCACT GCTGAGCGCG           60
CTCCGGCACG CCGTTGGTCA GCAG                                                  84
```

( 2 ) INFORMATION FOR SEQ ID NO: 33:

( i ) SEQUENCE CHARACTERISTICS:
        ( A ) LENGTH: 84 base pairs
        ( B ) TYPE: nucleic acid ( C ) STRANDEDNESS: single
( D ) TOPOLOGY: linear ( i i ) MOLECULE TYPE: DNA (synthetic)

( i i i ) HYPOTHETICAL: NO ( x i ) SEQUENCE DESCRIPTION: SEQ ID NO: 33:

```
GGCGCCGGAA ACCGGCAGCA CCTGCCGCAC GTCGGGCGAG ATGTCGTCGG GGTTCTGCTG      60
CGCATAGGCG TTGATGCCCG CTGC                                             84
```

( 2 ) INFORMATION FOR SEQ ID NO: 34:

( i ) SEQUENCE CHARACTERISTICS:
( A ) LENGTH: 84 base pairs
( B ) TYPE: nucleic acid
( C ) STRANDEDNESS: single
( D ) TOPOLOGY: linear ( i i ) MOLECULE TYPE: DNA (synthetic)

( i i i ) HYPOTHETICAL: NO ( x i ) SEQUENCE DESCRIPTION: SEQ ID NO: 34:

```
CGGCGGGTCG CCCTCGCCCA GGGTGCGCCC GGGCGACGCG ACATAGAGGA AGTTCATCAG      60
GCGGTGGGCG TGGGCCACCA CGTC                                             84
```

( 2 ) INFORMATION FOR SEQ ID NO: 35:

( i ) SEQUENCE CHARACTERISTICS:
( A ) LENGTH: 60 base pairs
( B ) TYPE: nucleic acid
( C ) STRANDEDNESS: single
( D ) TOPOLOGY: linear ( i i ) MOLECULE TYPE: DNA (synthetic)

( i i i ) HYPOTHETICAL: NO ( x i ) SEQUENCE DESCRIPTION: SEQ ID NO: 35:

```
GCCCAGGGTG CGGCCGGGCG ANNNNNNNNN NNNNNNGTTC ATCAGGCGGT GGGCGTGGGC      60
```

( 2 ) INFORMATION FOR SEQ ID NO: 36:

( i ) SEQUENCE CHARACTERISTICS:
( A ) LENGTH: 57 base pairs
( B ) TYPE: nucleic acid
( C ) STRANDEDNESS: single
( D ) TOPOLOGY: linear ( i i ) MOLECULE TYPE: DNA (synthetic)

( i i i ) HYPOTHETICAL: NO ( x i ) SEQUENCE DESCRIPTION: SEQ ID NO: 36:

```
ATAGCCGTAG AAGGCTGAGG GNNNNNNNNN NNNNNNGATG TGCGGGACGC CGTAGCC         57
```

( 2 ) INFORMATION FOR SEQ ID NO: 37:

( i ) SEQUENCE CHARACTERISTICS:
( A ) LENGTH: 48 base pairs
( B ) TYPE: nucleic acid
( C ) STRANDEDNESS: single
( D ) TOPOLOGY: linear ( i i ) MOLECULE TYPE: DNA (synthetic)

( i i i ) HYPOTHETICAL: NO ( x i ) SEQUENCE DESCRIPTION: SEQ ID NO: 37:

GCTGCGCGCC TGNNNNNNGC CNNNGCCNNN GAANNNTGAG GGCGCGTC 48

( 2 ) INFORMATION FOR SEQ ID NO: 38:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( x i ) SEQUENCE DESCRIPTION: SEQ ID NO: 38:

ATAGTTGGTG GCCCCCACCA TGCCGTTAAC GGTATTGGTG ATGCCCATCC GCTGGTTGAA 60

GGCGAAGCGG ATGAC 75

( 2 ) INFORMATION FOR SEQ ID NO: 39:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( x i ) SEQUENCE DESCRIPTION: SEQ ID NO: 39:

CTCGGCCCGT TGGGCGCCA CGCCGTTGAA GCTGTAGTTG ATGGTACCTT CGCGGTCGGC 60

GTAGACGATG TTGAA 75

( 2 ) INFORMATION FOR SEQ ID NO: 40:

( i ) SEQUENCE CHARACTERISTICS:
        ( A ) LENGTH: 84 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( x i ) SEQUENCE DESCRIPTION: SEQ ID NO: 40:

ATTGGAATTC TGCACGAAGC CGCCCGGCGG ATTGGTGACG CGCGGCAGAT CGTCCAGCGG 60

GTGTGTCTCG GTCCACAGGT AACG 84

( 2 ) INFORMATION FOR SEQ ID NO: 41:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( x i ) SEQUENCE DESCRIPTION: SEQ ID NO: 41:

CAGCAGGCGC GCCGCCGCCT GGACCTCGGG ATCGGGATCG ATCAGGGCGG CCGGGATCAG 60

GTCCGGCAAG GTGCG 75

( 2 ) INFORMATION FOR SEQ ID NO: 42:

( i ) SEQUENCE CHARACTERISTICS:
        ( A ) LENGTH: 84 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( x i ) SEQUENCE DESCRIPTION: SEQ ID NO: 42:

```
GTCGGCGCGC GACACGCGTT CGATCTGATC GCTGTAGTGC GTCGTGCCCG GGTGGCGAGA      60

GTTGCCGTAG CTCATCAGGC CATA                                             84
```

( 2 ) INFORMATION FOR SEQ ID NO: 43:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( x i ) SEQUENCE DESCRIPTION: SEQ ID NO: 43:

```
AAGGCGGTCC TGNNNNNNGA CNNNGCCNNN CGCNNNATAN NNATCGGCCT CGCC            54
```

( 2 ) INFORMATION FOR SEQ ID NO: 44:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( x i ) SEQUENCE DESCRIPTION: SEQ ID NO: 44:

```
CCAGAGCTTG AACCAGACGG ANNNNNNNNN NNNNNCAGC CGCCGCATCA CGGC             54
```

( 2 ) INFORMATION FOR SEQ ID NO: 45:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( x i ) SEQUENCE DESCRIPTION: SEQ ID NO: 45:

```
CACCATCGCG CANNNGCTCC ANNNNNNATT CTGGTCGGCN NNGTGGGGGC TGGC            54
```

( 2 ) INFORMATION FOR SEQ ID NO: 46:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( x i ) SEQUENCE DESCRIPTION: SEQ ID NO: 46:

GCCCTTTCTG CATATGTGTC CCTTATTTTT A    31

( 2 ) INFORMATION FOR SEQ ID NO: 47:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( x i ) SEQUENCE DESCRIPTION: SEQ ID NO: 47:

CAGACGGTCT TGNNNNNNCG CNNNACCNNN GCCNNNATAN NNGCCATAGT GGCT    54

( 2 ) INFORMATION FOR SEQ ID NO: 48:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( x i ) SEQUENCE DESCRIPTION: SEQ ID NO: 48:

TTCCAGATTC GTGTCGGANN NNNNNNNNN NNNGGAGCCC ACCCAGATCA T    51

( 2 ) INFORMATION FOR SEQ ID NO: 49:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO: 49:

TCTATTTTTC ATATGATCCT CTGGCAG    27

( 2 ) INFORMATION FOR SEQ ID NO: 50:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( x i ) SEQUENCE DESCRIPTION: SEQ ID NO: 50:

TTCGCTAGTG CTATCAGANN NNNNNNNNN NNNGGTGCCC ACAAATATCA T    51

MUTATED β-LACTAM ACYLASE GENES

FIELD OF THE INVENTION

The present invention relates to mutations of genes encoding acylases, resulting in alterations in the substrate specificity of acylase enzymes. Some of these mutant enzymes exhibit catalytic properties which make them particularly suitable for the deacylation/acylation of β-lactam derivatives. Among those is a preferred group which is designed for a one-step conversion of Cephalosporin C and derivatives to 7-aminocephalosporanic acid and derivatives.

BACKGROUND OF THE INVENTION

The basic antibiotics of the β-lactam type are principally obtained by fermentation. Fungi of the genus Penicillium and Cephalosporium (Acremonium) are used for the production of raw material for β-lactam antibiotics as Penicillin G, Penicillin V and Cephalosporin C. These fermentation products, also referred to as PenG, PenV and CefC, respectively, are the starting materials for nearly all currently marketed penicillins and cephalosporins. The side-chains of these compounds, phenylacetyl, phenoxyacetyl and aminoadipyl, respectively, are removed by cleavage of an amide linkage (deacylation), resulting in 6-aminopenicillanic acid (6-APA) in case of the two penicillin molecules and 7-aminocephalosporanic acid (7-ACA) in case of the cephalosporin. The particular enzymes which accomplish these conversions are referred to herein as "acylases" or "amidases". These denominations as used in this specification have the same meaning.

Also, the conversion of Cephalosporin G to 7-amino 3-deacetoxycephalosporanic acid (7-ADCA) is mentioned. However, Cephalosporin G (CefG) is not a fermentation product but is usually produced chemically from Penicillin G. The basic structures of the various penicillins and cephalosporins discussed above are shown in FIG. 1.

Synthetic manipulation to produce the various penicillins and cephalosporins of choice basically starts from 6-APA, 7-ACA and 7-ADCA, respectively.

The conversion of Penicillin G and Penicillin V to 6-APA may be performed both chemically and enzymatically. The classical way is the chemical cleavage, but enzymatic processes are preferred nowadays (for review, see Lowe [1]). Costs and environmental considerations are arguments in favour of an enzymatic process.

The cleavage of the CefC side-chain to 7-ACA is usually carried out chemically, according to the so-called iminohalide process. However, this process has serious disadvantages, since it is complex, requiring inter alia multiple steps, extremely low temperatures and expensive reagents.

The conversion of β-lactam intermediates to the desired semi-synthetic antibiotics may also be performed chemically and enzymatically, the enzymatic route being basically preferred if a suitable enzyme is available. Penicillin acylases are such enzymes in a number of cases. The enzymatic conversion takes advantage of the fact that any enzymatic reaction is reversible, if the correct conditions are applied (Abbott B. J. [2]).

Various types of microorganisms have been proposed in the literature as acylase producing strains useful for the deacylation of β-lactam derivatives obtained by fermentation and/or the acylation of 6-APA and 7-ACA to semi-synthetic β-lactam antibiotics of choice. Examples of such acylase producing microorganisms are certain strains of the species *Escherichia coli, Kluyvera citrophila, Proteus rettgeri, Pseudomonas sp., Alcaligenes faecalis, Bacillus megaterium, Bacillus sphaericus,* and *Arthrobacter viscosus.*

According to the literature several types of acylases may be envisaged, based on their molecular structure and substrate specificity (Vandamme E. J. [3]).

Type-I acylases are specific for Penicillin V. These enzymes are composed of four identical subunits, each having a molecular weight of 35 kDa. A complete nucleotide sequence of the cloned gene from *Bacillus sphaericus* has been reported (Ollson A. [4]).

Type-II acylases all share a common molecular structure: these enzymes are heterodimers composed of a small subunit (α; 20–25 kDa) and a large subunit (β; 60–65 kDa). With respect to the substrate specificity, Type-II acylases may be further divided into two groups:

Type-IIA acylases are very specific for Penicillin G. In general, they are not so much specific for the moiety adjacent to the nitrogen atom of the amide group (this might be a cephem group, a penem group, an amino acid, etc.), but the substrate specificity resides in the acyl moiety of the substrate. This acyl moiety must be very hydrophobic and is preferably benzyl or (short) alkyl. Examples of substrates which are not hydrolyzed by Type-IIA acylases are those with dicarboxylic acids as acyl moiety: succinyl, glutaryl, adipyl and also aminoadipyl, the side-chain of CefC. Examples of Type-IIA acylases are the enzymes from *Escherichia coli, Kluyvera citrophila, Proteus rettgeri* and *Alcaligenes faecalis.* Type-IIB acylases have been reported to be capable of hydrolyzing cephalosporins (including the desacetoxy-derivative) with succinyl, glutaryl and adipyl as an acyl moiety and even in one case CefC to a very limited degree (Shibuya Y. [5]; Matsuda A. [6]). So far these acylases have only been found in Pseudomonas species, and in certain strains of *Bacillus megaterium* and *Arthrobacter viscosus.*

The literature relates mainly to penicillin acylases. The synthetic potential of penicillin acylases, however, is limited due to the specificity of the enzyme. In more recent years also publications relating to Cephalosporin C acylases have appeared, but the activity of the reported enzymes was relatively low. No commercial enzymatic process for the conversion of Cephalosporin C to 7-ACA is available up to now, despite intensive efforts to find a suitable enzyme (cf. Walton R. B. [7]).

There is, therefore, a substantial interest in developing acylase enzymes which are highly efficient in deacylation/acylation reactions to produce desired chemical entities. Of particular interest are the enzymatic deacylation of β-lactams and especially PenG, PenV and CefC, and derivatives thereof, to 6-APA and 7-ACA and derivatives, respectively, and the acylation of the latter compounds to produce semi-synthetic pencillins and cephalosporins of interest. It is of major importance in this connection to dispose of an efficient acylase enzyme which is capable of catalyzing the conversion of CefC (and derivatives) to 7-ACA (and derivatives).

The invention aims to provide such efficient enzymes.

RELEVANT PRIOR ART

Mahajan [8] gives a review of various penicillin acylases and distinguishes PenG and PenV specific acylases.

European Patent Application EP-A-0283218 discloses an enzymatic one step conversion of CefC and derivatives to 7-ACA and derivatives, using an enzyme derived from *Arthrobacter viscosus* strain ATCC 53594.

EP-A-0322032 discloses the same enzymatic one step conversion, using an enzyme derived from *Bacillus megaterium* strain ATCC 53667.

U.S. Pat. No. 4,774,179 discloses basically the same conversion, using Pseudomonas sp. SE-83 or SE-495, or material obtained from these microorganisms by subjecting them to chemical and/or physical treatment.

As already stated before, the low activities of these enzymes stands in the way of a commercial use up till now.

The use of recombinant DNA methods has enabled an increase of the production levels of commercially used penicillin acylases (Mayer [9]) and has enlarged the insight into the processing of these enzymes (Schumacher [10]). The penicillin acylase of *E. coli* was found to be produced as a large precursor protein, which was further processed into the periplasmic mature protein constituting a small ($\alpha$) and a large ($\beta$) subunit. Cloning and sequencing of the *Kluyvera citrophila* acylase gene has revealed a close homology with the *E. coli* acylase gene (Barbero [11]). Also for *Proteus rettgeri* penicillin G acylase a small and a large subunit has been described (Daumy [12]).

Williams [33] describes substrate specificity modifications of the PenG acylase of *E. coli* ATCC 9637 occurring in a natural variant. The method was based on replacement subcloning of regions in the wild-type gene with equivalent regions of the gene of a natural mutant.

Forney [34, 35] describes the selection of amidases with novel substrate specificities from penicillin amidase of *E. coli* and the alteration of catalytic efficiency of such a penicillin amidase (of *E. coli* ATCC 11105) by propagation of a recombinant plasmid in a *E. coli* strain with a high mutation frequency. D-(−)-α-aminophenylacetyl-(L)-leucine was used as a substrate analog of ampicillin and cephalexin. It was found possible to alter the substrate specificity of penicillin amidase and obtain enzymes that, at low pH, hydrolyze amides with α-aminophenylacetyl moieties more rapidly.

These publications neither teach nor suggest the instant invention.

SUMMARY OF THE INVENTION

The present invention relates to mutations of acylase genes, some of which result in alterations in the substrate specificity of acylase enzymes. Mutations are created at specific nucleotides of the acylase genes, and, in various specific embodiments, the mutant enzymes show altered biochemical properties, which may result in, but are not limited to, increased specificity towards the deacylation of certain β-lactam antibiotics.

In a preferred embodiment new mutant enzymes are provided which are particularly suitable for a one-step conversion of CefC and derivatives to 7-ACA and derivatives.

In another preferred embodiment new mutant enzymes are provided which are particularly suitable for the acylation of 6-APA and 7-A(D)CA, resulting in the production of desired penicillin and cephalosporin derivatives.

In an embodiment of the invention genes encoding known Type-IIA or Type-IIB acylases, for example PenG acylases from *Escherichia coli*, *Kluyvera citrophila*, *Alcaligenes faecalis* or any other organism producing such enzymes, and glutaryl-Cef acylases from Pseudomonas SE-83 AcyII, Pseudomonas SY-77 or any other organism producing such enzymes, are mutated in such a way that the enzymes obtain an altered specifity for their substrates.

These and other embodiments will hereinafter be outlined in further detail.

BRIEF DESCRIPTION OF THE DRAWINGS

FIG. 5A–5C: nucleotide sequence (SEQ ID NO: 3) and derived amino acid sequence (SEQ ID NO: 4) of the penicillin acylase gene of *Alcaligenes faecalis*. Amino acids are indicated in the 1-letter code.

FIGS. 13A–13C: nucleotide sequence (SEQ ID NO: 1) and derived amino acid sequence (SEQ ID NO: 2) of the complete Pseudomonas SY-77 glutaryl-Cef acylase gene.

FIGS. 14A–14C: alignment of Type-II acylases from *E. coli* (e.col) (SEQ ID NO: 5), *Kluyvera citrophila* (K.cit (SEQ ID NO: 6)), *Alcaligenes faecalis* (a.fae), Pseudomonas SE-83 AcyII (AcyII (SEQ ID NO: 7)) and Pseudomonas SY-77 (SY-77). An asterix denotes that the sequence contains the same amino acid at that position as the sequence from the *E. coli* acylase.

FIGS. 15A–15B: region selection in the *Alcaligenes faecalis* α-subunit.

FIGS. 16A–16D: region selection in the *Alcaligenes faecalis* β-subunit.

FIGS. 17A–17B: amino acid residue selection in the SY-77 α-subunit.

FIGS. 17C–17F: amino acid residue selection in the SY-77 β-subunit.

DETAILED DESCRIPTION OF THE INVENTION

Figure 1:
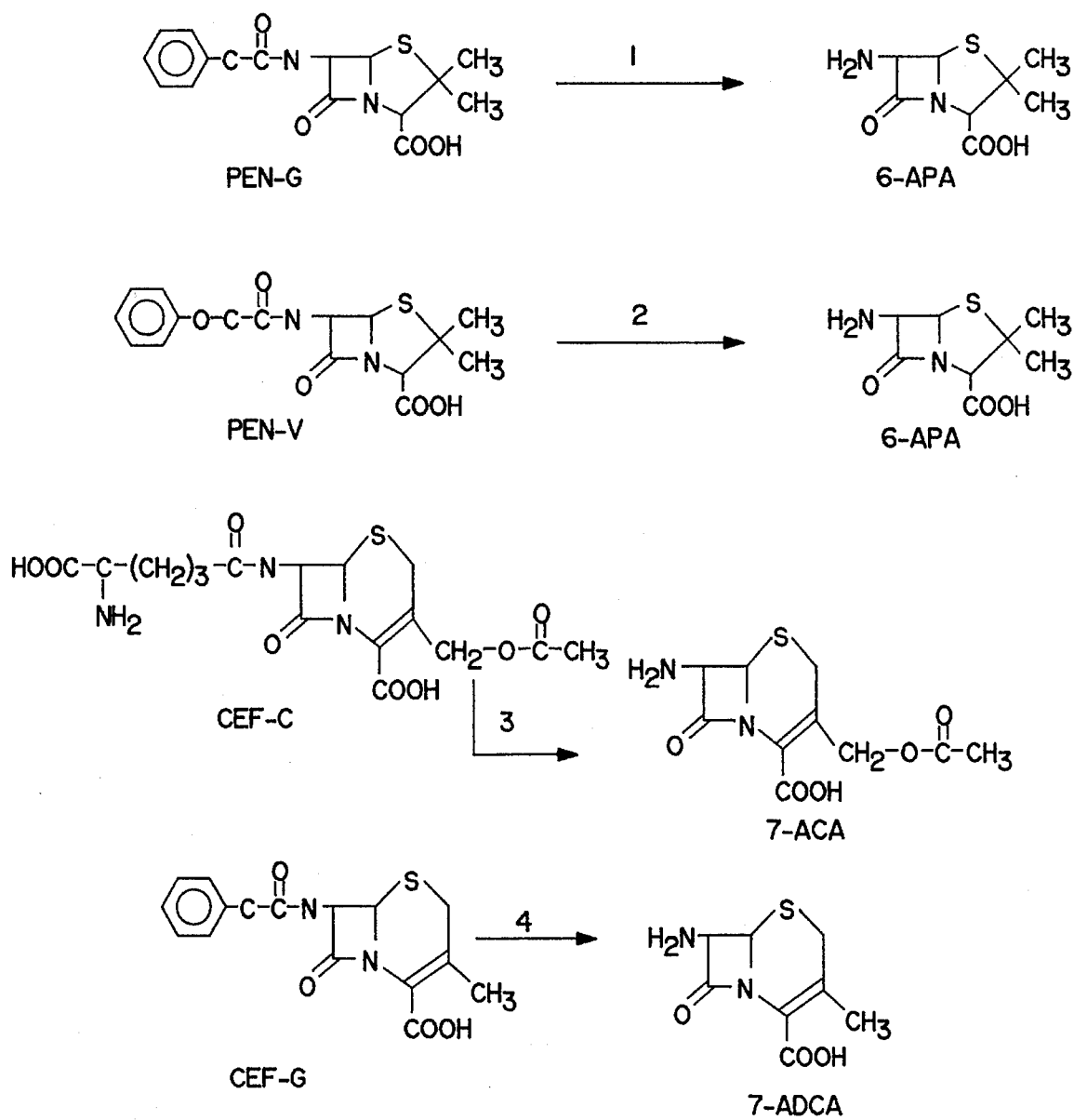
FIG. 1: reaction schemes of certain β-lactam conversions. Reaction 1 is the deacylation of PenG resulting in 6-APA and phenylacetic acid. Reaction 2 reflects the deacylation of PenV resulting in 6-APA and phenoxyacetic acid. Reaction 3 is the deacylation of CefC into 7-ACA and (α-)aminoadipic acid. Reaction 4 reflects the deacylation of CefG into 7-ADCA and phenylacetic acid.
Figure 2:
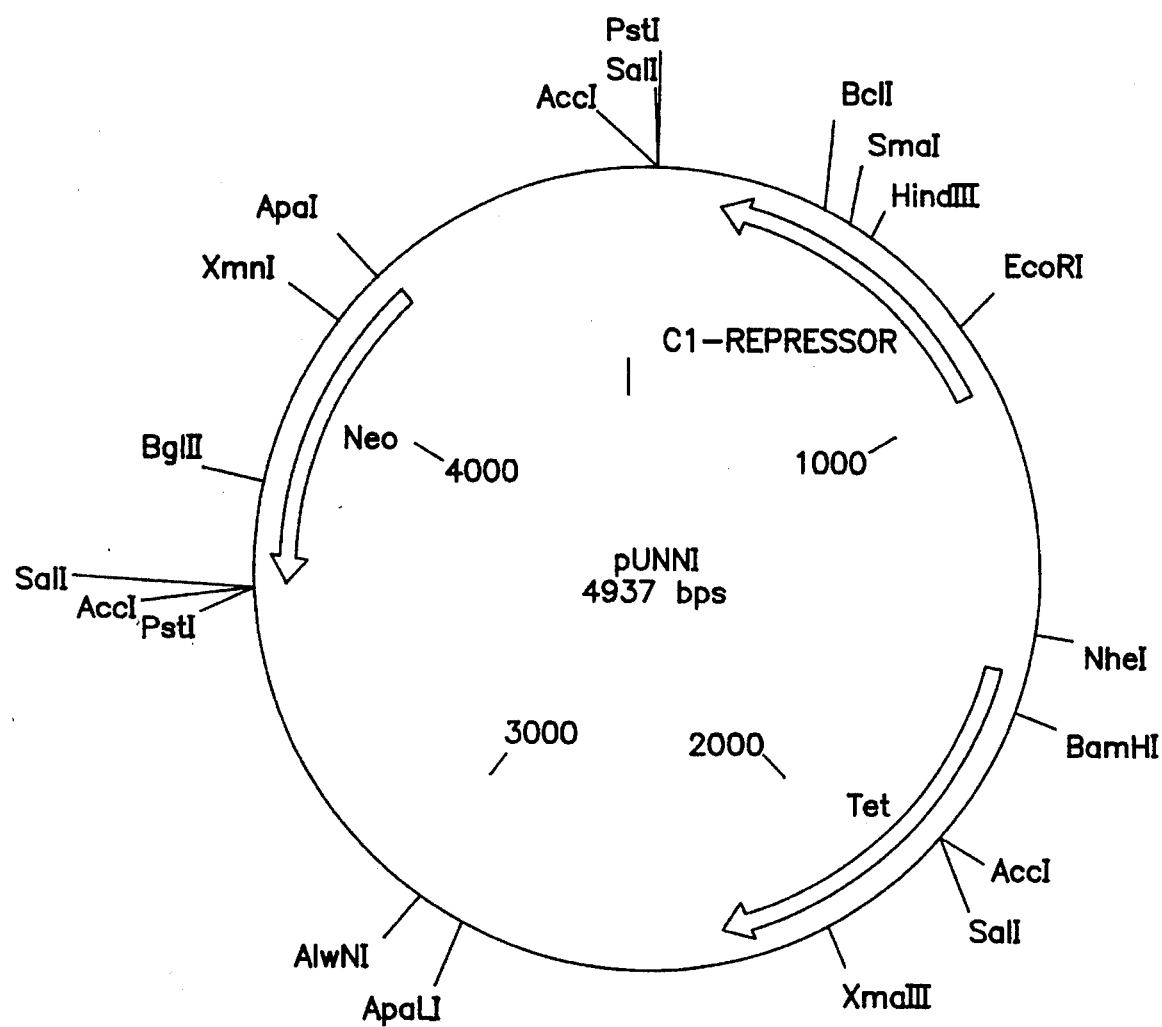
FIG. 2: restriction map of plasmid pUNNI.

The present invention uses protein engineering as a tool to develop acylases with an altered substrate specificity. The invention is based on the finding that the genes encoding various (known) acylases show a significant degree of homology at certain regions. A comparative analysis was made which has indicated that certain mutations may alter the biochemical properties of the acylases. According to the method which will be outlined below a number of potential mutation sites will become apparent.

It has been observed that the tertiary structures in homologous proteins are much more conserved in evolution than the primary structures and considerably more than the DNA-sequences. This is for example illustrated by the globin-family (Dickerson [13]). The globin fold is encoded by many different amino acid sequences, some differring from others in as many as 86% (130 out of 150 residues). Nevertheless, their closely similar conformation support the current assumption that they diverged from a common evolutionary ancestor.

When organisms divert in the course of the evolution, their genes will gradually accumulate mutations to produce proteins with quite different amino acid sequences. The more they divert, the less the sequence homology. The frequency of mutations is high at sites which are irrelevant for folding, stability or catalytic properties. Usually, these sites occur at positions in the polypeptide chain where the side chain is on the surface. Only at reversed turns, there is a tendency for residues to have one of the short polar side chains, or to be glycine or proline, the residues most freqently found at this position. Interior residues are changed less frequently and the non-polar nature of the side chain is conserved fairly well. Since mutation during evolution is a random process, there will be also substitutions that affect functional properties. Only when these substitutions do not cause a disadvantage to the organism, they will be tolerated. As a consequence, variation of these amino acids is much less. Usually, residues directly involved in catalysis are found to be highly conserved. Insertions and deletions tend to occur in surface loops between secondary structure units, with little perturbation of the interior. Usually, in the diverged molecules, elements of secondary structure are arranged in a similar three dimensional topology.

The sequence homology found among the Type-II acylases, as well as the similarity in the molecular architecture of these molecules suggest that Type-IIA and Type-IIB acylases evolved from a single ancestral gene. Also the typical maturation process suggests a common origin. The comparison of sequences of proteins which diverged from a common ancestor can reveal those residues that are involved directly in the functional properties of the enzyme.

In an embodiment of the invention genes encoding known Type-IIA or Type-IIB acylases, for example PenG acylases from *Escherichia coli*, *Kluyvera citrophila*, *Alcaligenes faecalis* or any other organisms producing such enzymes, and glutaryl-Cef acylases from Pseudomonas SE-83 AcyII, Pseudomonas SY-77 or any other organisms producing such enzymes, are mutated in such a way that the enzymes obtain an altered specificity for their substrates.

The alteration of the substrate specificity of PenG acylases (Type-IIA) is achieved in such a way that the mutant enzymes are able to cleave or synthesize penicillin and cephalosporin derivatives possessing side-chains other than phenylacetyl, which is the natural side-chain of Penicillin G. Examples of side-chains which are presently not significantly affected by PenG acylases are acyl groups derived from the dicarboxylic acids succinic acid, glutaric acid, adipic acid and aminoadipic acid (the latter being the natural side-chain of CefC).

In another embodiment of the invention the alteration of the substrate specificity of Cef acylases (Type-IIB) is performed in such a way that the mutant enzymes cleave or synthesize penicillin and cephalosporin derivatives possessing side-chains other than the glutaric acid moiety. Examples of suitable side-chains which may be cleaved or synthesized by such new mutant enzymes are those which are presently not substantially affected by Cef acylases such as the moieties derived from adipic acid and aminoadipic acid (which is the natural side-chain of Cephalosporin C), hydrophobic side-chains such as the moiety derived from phenylacetic acid, the natural side-chain of Penicillin G, and alkyl side-chains.

In still another aspect the alteration of the specificity and activity of acylases (Type-IIA and IIB) is performed for side-chains which are already existing substrates for the said acylases. Using protein engineering the affinity for a substrate may be altered (e.g. increased, expressed by a lower $K_m$ for said substrate) or the catalytic turnover may be altered (e.g. increased, expressed by a higher $k_{cat}$ for said substrate).

In order to achieve alterations in the enzyme molecule, it is of course highly desirable to avail of the 3D structure of said enzyme. Sofar, no high-resolution, 3D-structures of acylases have been published. However, several genes encoding acylases have been sequenced, viz. the genes from *E. coli* and *Kluyvera citrophila* (both Type-IIA) and Pseudomonas SE-83 AcyII (Type-IIB) and this has gained insight into the biological processing of these enzymes. Amino and carboxy terminal sequencing of the isolated subunits revealed that the gene encodes a precursor protein consisting of a signal sequence followed by the α-subunit, a connecting peptide (spacer) and finally the β-subunit.

According to an embodiment of the invention protein engineering of the acylases is carried out following two strategies, depending on the availability of a 3D-structure of the selected acylases. The procedure for determining a 3D-structure is known in the art.

In the absence of a 3D-structure substantially the following strategy is followed:

First, a number of selected acylase genes are cloned into a suitable expression host organism. Preferred microorganisms include *E. coli*, Bacillus, Pseudomonas. Then, the DNA-sequence of each cloned acylase is determined. The DNA-sequences are translated into the corresponding amino acid sequences and these amino acid sequences are then aligned in such a way as to obtain a homology which is as high and relevant as possible. For sequence alignment the types of amino acids may be suitably used as parameters, based on identity but also on similarity. For example, serine is similar to threonine, aspartic acid is similar to glutamic acid, etc. Further suitable parameters are, for example, secondary structure predictions (according to several "standard" procedures, e.g. Chou Fassman), and charge distribution over the sequences. In a further step, regions are selected for mutation.

The randomly generated mutants are selected by allowing only those mutants to grow which are capable of cleaving a specific substrate. These substrates usually comprise an amide derivative containing as an acyl moiety the side-chain for which the specificity of the said acylase is desired, and as an amine moiety an L-amino acid which is indispensible for growth of the expression host. Therefore, only those hosts, expressing an acylase with the desired substrate specifity, are able to cleave the said amide compound, thereby liberating the essential amino acid. For example, D-α-aminoadipyl L-leucine (hereinafter referred to as aminoadipyl leucine, which compound is in the D-form) can be used as the amide compound to select for a CefC acylase using leucine auxotrophic expression organisms. Another example of an amine moiety is ammonia, which may serve as the sole nitrogen source for the expression host.

The "positive" mutant acylases which reveal the desired substrate specificity, on the basis of the selection procedure used, are then purified and tested. The sites of mutagenesis are identified by sequencing the gene of the mutant acylases. Examples of such mutants are the mutants V62L, Y178H, V179G of SY-77 acylase. Other mutations (including amino acid replacements, deletions and insertions) may also be performed at or around these sites in order to further increase the activity of the mutant acylase. Thus, it will be understood that any combinations of the above-mentioned mutations are included within the present invention. An example of such combination is the mutant L177I/Y178H of SY-77 acylase.

When a 3D-structure of an acylase is available, the first (four) steps of the above procedure still need to be done, but the selection may be based on the 3D-structure. Two approaches may be envisaged:

a) A rational approach, in which one or a few amino acids are mutated into other amino acids. This does not create a large amount of mutants and therefore, all mutants can be handled with respect to purification and testing for their substrate specificity. From the three-dimensional structure one or more amino acids in the active site may be selected in order to be mutated in such a way that the desired side-chain can be accomodated optimally in the active site. For example, accomodating the aminoadipyl side-chain of CefC into a PenG acylase, requires that the binding pocket is first of all enlarged in order to fit in the longer alkyl chain, and secondly that it is supplied with the proper electrostatic environment to bind the amino and/or carboxy group of the aminoadipyl side-chain. As another example, the introduction of the proper electrostatic environment in order to accomodate the positively charged amino group of the side-chain of CefC may change the specificity of a glutaryl-Cef acylase (which already shows some activity with aminoadipyl Cephalosporin) to a CefC acylase.

b) a "targeted random mutagenesis (TRM) approach". Despite the 3D-structure it may be difficult to make predictions. If it is possible to assess that a few amino acids are involved in substrate binding, a targeted random mutagenesis is advantageously performed followed by a selection test as indicated above. This approach yields for example 8000 possible mutants when a set of 3 sites is mutated randomly (with respect to the amino acids, 20*20*20; on DNA level—where the mutants have to be made—this is as many as $(4*4*4)^3 = 262,000$ possible mutants!).

In a further aspect of the invention it was found that the acylase enzyme from *Alcaligenes faecalis* showed a surprising high degree of homology with the acylases from *E. coli* and *Kluyvera citrophila*. The acylase encoding gene from *Alcaligenes faecalis* was isolated and sequenced and compared with the genes of the two other species. It appeared that a common feature of the sequences is that the genes encode a large polypeptide precursor which may be composed as is depicted in Table 1. The question marks relating to *Alcaligenes faecalis* indicate only that the end of the sequences could not yet be determined unambiguously.

TABLE 1

Number of amino acids per acylase peptide

| Acylase from | signal seq. | α-subunit | connecting peptide | β-subunit |
|---|---|---|---|---|
| *Escherichia coli* | 26 | 209 | 54 | 557 |
| *Kluyvera citrophila* | 26 | 209 | 54 | 555 |
| *Alcaligenes faecalis* | 26 | 210 (?) | 29 (?) | 551 |
| Pseudomonas SE-83 AcyII | 0 | 239 (?) | ? | 535 |
| Pseudomonas SY-77 | 28 | 169 (?) | ? | 521 |

In another aspect of the invention it was found that α- and β-subunit of the acylase from Pseudomonas SY-77 depicted regions with a high sequence homology both with Type-IIA acylases and the Type-IIB SE-83 AcyII acylase. The acylase encoding gene of Pseudomonas SY-77 was isolated and the complete sequence of the gene was obtained. For both Pseudomonas acylases there is no evidence for a connecting peptide between α- and β-subunit. The SY-77 enzyme appeared to have a signal peptide whereas N-terminal sequencing of the SE-83 AcyII showed that the mature α-subunit commenced just after the initiating methionine (Matsuda A. [6]).

The kinetics of Type-II acylases are consistent with catalysis proceeding via an acyl-enzyme intermediate (Mahajan [8]).

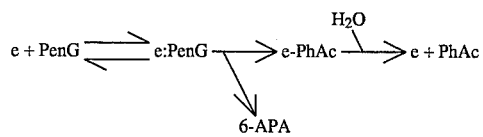

In the first step of the mechanism, the substrate PenG binds to the enzyme to form the non-covalent Michaelis-Menten complex e:PenG. In the subsequent step, the covalent intermediate is formed between the enzyme and the acyl moiety of the substrate (e-PhAc=acylated enzyme; PhAc= phenylacetic acid) with the concomitant release of the first product 6-APA. Deacylation occurs with the aid of a water molecule thereby liberating the second product PhAc and regenerating the enzyme. This mechanism is also in accordance with the observations that PhAc acts as a competitive inhibitor and 6-APA as a non-competitive one.

The above mechanism, which is identical to the one postulated for the serine proteases, together with the finding that phenylmethylsulfonylfluoride (PMSF, a potent inhibitor of serine proteases) inhibits the enzyme (Mahajan [8]), suggests that these enzymes are also serine hydrolases containing a catalytic triad consisting of a serine, histidine and aspartic acid. Such a catalytic triad is not only found in the serine proteases of the trypsin- and subtilisin family, but was recently also discovered in two, structurally different, triacylglycerol lipases (Blow D. [14]; Winkler F. K. [15]; Brady L. [16]) from human pancreas and the fungus *Rhizomucor miehei*. Based on the sequence alignment Ser765 of *Alcaligenes faecalis* acylase is most likely the active site serine. Based on this finding further mutants are provided with altered activity.

In a further aspect of the present invention, the genes coding for the acylases from *Escherichia coli, Alcaligenes faecalis,* Pseudomonas SY-77 and Pseudomonas SE-83 AcyII, respectively, were cloned into the expression host organism *E. coli.*

The DNA sequences of the acylases from *E. coli, Kluyvera citrophila,* Pseudomonas SE-83 AcyII and the partial DNA sequence for Pseudomonas SE-77 were taken from the literature. The DNA sequence for the acylase from *Alcaligenes faecalis* was determined as well as the remainder of the DNA sequence of the Pseudomonas SE-77.

The alignment of the five amino acid sequences revealed a close homology between the PenG acylases (>45%), whereas the homology between the PenG acylases and the glutaryl-Cef acylases was lower (25–35%) while also the homology between the glutaryl-Cef acylases was of that same order. Yet regions of high homology between all five sequences could be detected which points to a possible similar 3D-structure (already supported by the heterodimeric structure).

Regions of particular interest to mutate are the α- and β-subunits of the acylase.

It is to be understood that all amino acids, as used in this specification, are in the L-form, unless otherwise stated. The term "aminoadipyl" is used to indicate the D-α-aminoadipyl moiety.

Mutant β-lactam acylases may also be cloned and expressed in a β-lactam producing microorganism. This would have the advantage that the deacylated β-lactam intermediate can be recovered directly from the fermentation broth. Cephalosporium and Penicillium strains are preferred hosts for this application of mutant β-lactam acylases.

The following Examples are offered by way of illustration and not by way of limitation.

MATERIALS AND METHODS

Cloning and Detection of Acylase Genes

General cloning techniques were performed as described by Maniatis [17], Ausubel [18] and Perbal [19]. These handbooks describe in detail the protocols for construction and propagation of rDNA molecules, the procedures for making gene libraries and the protocols for mutating DNA in a site-directed or random fashion. Enzymes used for DNA manipulations were purchased from commercial suppliers and used according to their instructions. Plasmids and *E. coli* cloning hosts were obtained from public culture collections.

Construction of Plasmid pUNN1

Plasmid pUNN1 was constructed as follows: Plasmid pUB110 (*S. aureus*) was cut with SnaBI and TaqI and the fragment carrying the neomycin resistance gene was cloned into SmaI, AccI digested pUC19 resulting in pPNeo. The small EcoRI-ScaI fragment of pPNeo was exchanged for the small EcoRI-ScaII fragment of pUC18 resulting in pPNeoII. Then the small Pst-Pst fragment of pPNeoII was cloned into the single PstI site of pUN121 (Nilsson [20]). After KpnI, XbaI digestion, nuclease S1 treatment and ligation, plasmid pUNN1 was recovered. This plasmid can be used as a positive selection vector (Nilsson, ibid.) and has the advantage over common cloning vectors that it does not contain a β-lactamase gene, which may destroy β-lactam antibiotics.

Enzyme Assays

Acylase activity was assayed by a spectrophotometric method based on the detection of primary amino groups with the fluorophor fluorescamine (S. Underfriend et al. [32]). For the detection of 7-ACA the method was adapted by Reyes et al. [21].

In order to determine enzymatic activity the enzyme was incubated with substrate at room temperature. The composition of the reaction mixture was: 20 mM sodium phosphate buffer pH 7.5, 1.2 mM substrate, 1.0 mM β-lactamase inhibitor 6-bromo-penicillanic acid and enzyme. The reaction was stopped by adding 0.5N HCl. Slow reactions were assayed immediately without prior stopping the reaction with HCl. From the reaction mixture 100 microliters were taken and mixed with 800 μl 0.2M sodium acetate buffer pH 4.5 and 100 μl of fluorescamine which was prepared in AR acetone (1 mg/ml). When the substrate contained an amino acid instead of 7-ACA, the sodium acetate buffer was replaced by 0.2M sodium phosphate pH 7.5. After 15 minutes the absorption at 378 nm was determined with an Uvicon 860 spectrophotometer and corrected for the appropriate blancs. Through a calibration curve the absorption at 378 nm can be related to the number of free amino groups released by hydrolysis of the substrate.

Mutagenesis of Acylase Genes

Site-directed mutagenesis of cloned DNA fragments was carried out as described by Stanssens [22] with the aid of the phasmid pMa/c system. Suitable gapped duplex molecules of acylase genes were constructed. With specific mismatch oligonucleotides site directed mutations were introduced. Expression of acylase genes was obtained in *E. coli* WK6 either from the homologous expression signals or from the *E. coli* lac, tac or trp promoter (De Boer [23]). Gapped duplex molecules were annealed with "spiked" oligonucleotides to obtain a region-targeted random mutagenesis (Hermes [24]. These "spiked" oligonucleotides were prepared by including traces of all 4 nucleotides during the synthesis of oligonucleotides on an Applied Biosystems DNA synthesizer. Alternatively, random mutagenesis of the gapped DNA was performed enzymatically with a method modified from Leethovaara [25]. By the choice of the gap the region to be mutagenised enzymatically was selected.

In another type of experiments targeted random mutagenesis was performed. This comprises the inclusion of all four bases at the codon for a specific amino acid during the synthesis of the oligonucleotide. In doing so, a mutagenic oligonucleotide which can mutate any amino acid is all other possible amino acids can be synthesized. A single amino acid position or a combination of several positions can be mutagenized in that way. Alternatively, random mutagenesis based on the PCR technology can be used [36].

Selective Media

Selective media for phenylacetyl leucine ("fal") were prepared as described by Garcia [26]. Minimal plates are as follows: M63 minimal agar, 2 g/l glucose, 1 mg/l thiamine, 10 mg/l proline and the appropriate antibiotic (50 μg/ml chloramphenicol (cap) or 25 μg/ml ampicillin (amp)). For selections on side-chain specificity (e.g adipyl or aminoadipyl) of acylases, 100 μg/l of the corresponding acyl leucine was included into minimal plates. Transformants or mutants of *E. coli* HB101 (Leu⁻) growing exclusively in the presence of the acyl leucine are considered to harbor an acylase gene with the desired specificity. Instead of leucine the amino acid moiety of the selective substrate was varied. In such case a suitable auxotrophic mutant of E. coli was used for selection. For example, selection on the substrate N-adipyl serine was carried out with E. coli strain PC2051 as a host (obtained from Phabagen, Utrecht, the Netherlands). Phenylacetyl leucine, aminoadipyl leucine, glutaryl leucine, adipyl alanine and adipyl serine were purchased from LGSS, Transferbureau Nijmegen, the Netherlands.

Phenylacetyl amide was added to a final concentration of 15 mM to minimal M63 medium supplemented with 0.2% of either succinate, glycerol or glucose as carbon source, and thiamine (1 µg/ml), proline (10 µg/ml), and the appropriate antibiotic. All salts in the basal medium were replaced by the corresponding salts containing either $Na^+$ or $K^+$ ions in order to ensure selective growth on the amide (Daumy [12]). Amides with the desired side-chains were purchased from commercial suppliers or prepared according to standard techniques. E. coli strains JM101, WK6, HB101, PC2051 and PC1243 were used as hosts to select for mutant genes with specificity for the selective amides.

Isolation Procedure Wild-type and Mutant Glutaryl Acylases

Cells were harvested by centrifugation and resuspended in 10 mM sodium phosphate buffer pH 7.4 containing 140 mM NaCl. The cells were disrupted through sonification (6×20 sec, 100 W, 100 mm bar, Labsonic 1510; after every 20 seconds the cells were cooled on ice for 30 seconds). Subsequently, the suspension was centrifugated. The sonification procedure was repeated with the resuspended pellet and finally the cell debris was removed by centrifugation. Supernatants were pooled and ammonium sulphate was added upto a 30% saturation. After 30 minutes stirring precipitated material was removed by centrifugation. The ammonium sulphate concentration of the supernatant was increased to 60% saturation and after 30 minutes the precipitate was collected by centrifugation. The pellet was dissolved in 20 mM sodium phosphate buffer pH 7.5 and extensively dialyzed against the same buffer.

EXAMPLE 1

Cloning of an E. coli Penicillin Acylase Gene

From the published restriction map and sequence of E. coli ATCC 11105 penicillin acylase gene (Sang-Jin [27]) it was concluded that the HindIII-SmaI fragment of 2.9 kb comprises the acylase gene ("pac"). Chromosomal DNA was digested with HindIII and SmaI and fractionated on a 0.5% agarose gel. Fractions from 2 to 4 kb were purified with Geneclean (BI0101, La Jolla, Calif.) and hybridized with the following oligonucleotide DNA probe (SEQ ID NO: 8):

TCGTACATTTTCAGCTGATCTTCATAGTGCTTATC derived from the sequence of E. coli pac.

Figure 3:
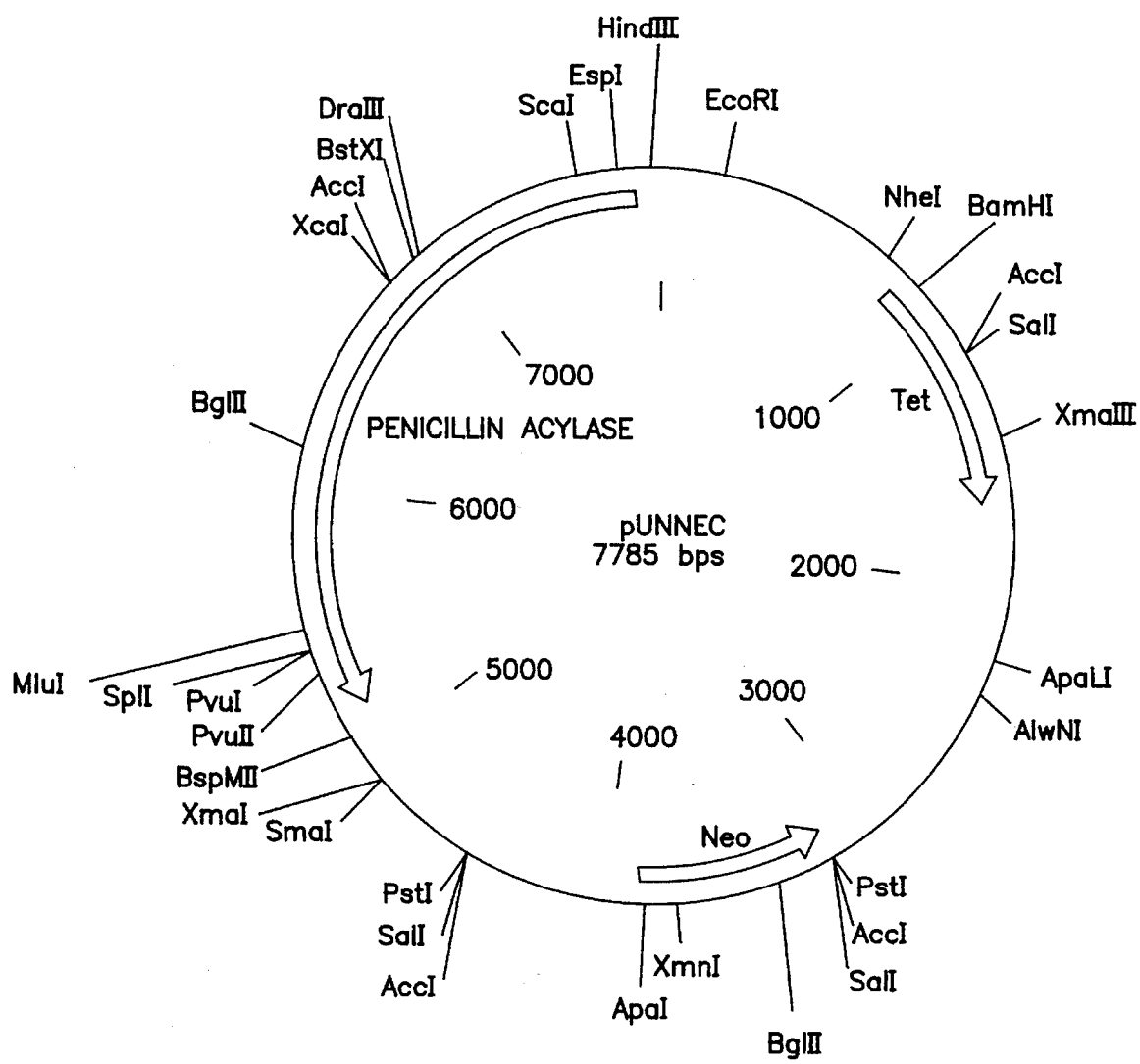
FIG. 3: restriction map of plasmid pUNNEC harboring the *E. coli* ATCC 11105 penicillin acylase gene.

The positively hybridizing fraction was then ligated into vector pUNN1 and transformed into E. coli HB101. Filter hybridization of 2000 transformants with the above-mentioned oligo probe resulted in the identification of plasmid pUNNEC1. The structure is shown in FIG. 3.

Colonies carrying pUNNEC1 were grown on HI-agar plates for 24 hours at 30° C. Then the plates were overlayered with 5 ml nutrient broth topagar containing Penicillin G (5 mg/ml) and 0.5 ml of an overnight culture of Serratia marcescens ATCC 27117 and incubated for another 24 hours. Penicillin acylase activity of the transformants can be seen from the inhibition zone around the colony, which results from a high sensitivity of Serratia marcescens for 6-APA (Meevootisom [28]).

EXAMPLE 2

Cloning of an Alcaligenes faecalis Penicillin Acylase Gene

Figure 4:
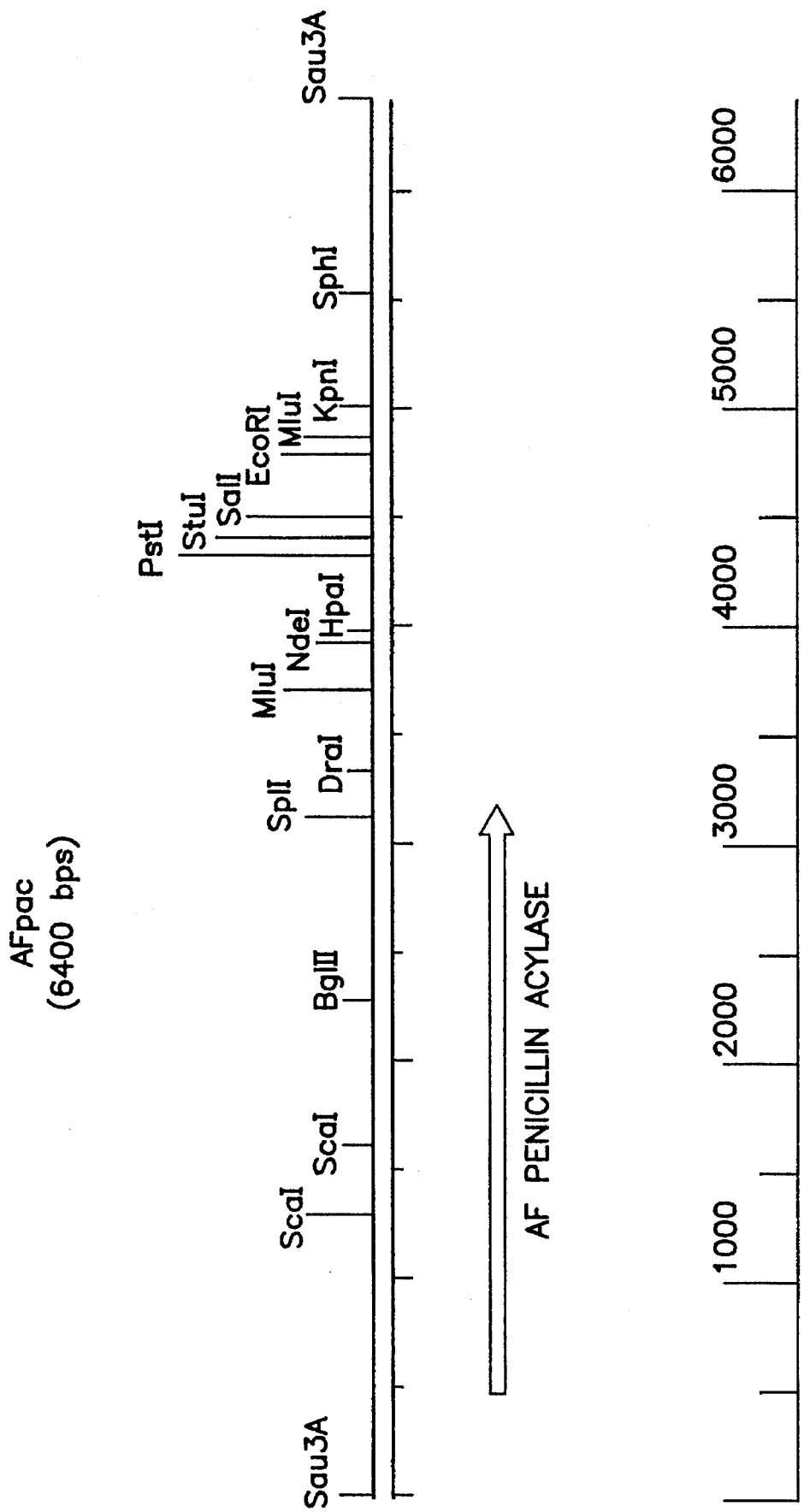
FIG. 4: restriction map of the 6.4 kb insert of plasmid pAF1.

Chromosomal DNA of Alcaligenes faecalis strain ATCC 19018 (=NCTC415) was isolated and partially digested with Sau3A. Fractions ranging from 4 kb to 7 kb were purified and ligated into vector pACY184, which was digested with BamHI. DNA was transformed into E. coli HB101 and plated onto fal-plates (see methods). Two positive clones, pAF1 and pAF2, could be identified. These clones were also tested with positive result in the Serratia marcescens overlay technique. The 6.4 kb insert of the pAF1 plasmid is shown in FIG. 4.

The localization of the gene was determined with the aid of an oligonucleotide designed on the $NH_2$ terminal sequence of the β-subunit of A. faecalis penicillin acylase. The amino acid sequence (SEQ ID NO: 9) reads:

S-N-L-W-S-T/R-(C)-P-E-(C)-V

The following oligonucleotide (SEQ ID NO: 10) was used as a hybridization probe on the pAF1 insert:

AGC AAC CTG TGG AGC A/C C/G C TGC CCG GAG TGC GT

From the position of the hybriding signal on the restriction map the orientation of the A. faecalis pac gene was determined (FIG. 4). The 3.9 kb SaU3A-NdeI subclone of the 6.4 kb insert, was shown to give penicillin acylase activity, whereas the 3.1 kb Sau3A-Sph1 fragment was inactive (FIG. 4). The DNA sequence of the 3.9 kb insert was determined by dedeoxy sequencing of suitable fragments in pTZ18R and pTZ19R (Pharmacia). The encoding DNA sequence and the derived amino acid sequence for A. faecalis penicillin acylase are shown in FIG. 5.

EXAMPLE 3

Cloning of a Pseudomonas Glutaryl-Cephalosporin Acylase Gene (A)

Pseudomonas SY-77 produces an enzyme capable of hydrolyzing glutaryl amidocephalosporanic acid into 7-ACA and glutaric acid. The gene encoding this enzyme was cloned (Matsuda [29]). DNA extracted from Pseudomonas SY-77 was digested with HpaI and SmaI and cloned into SmaI linearized vector pUNN1 in strain HB101. Transformants were selected on neomycin plates and hybridized with a probe derived from the DNA sequence (SEQ ID NO: 11) (Matsuda [29], ibid.):

ATG CTG AGA GTT CTG CAC CGG GCG GCG TCC GCC TTG

Figure 6:
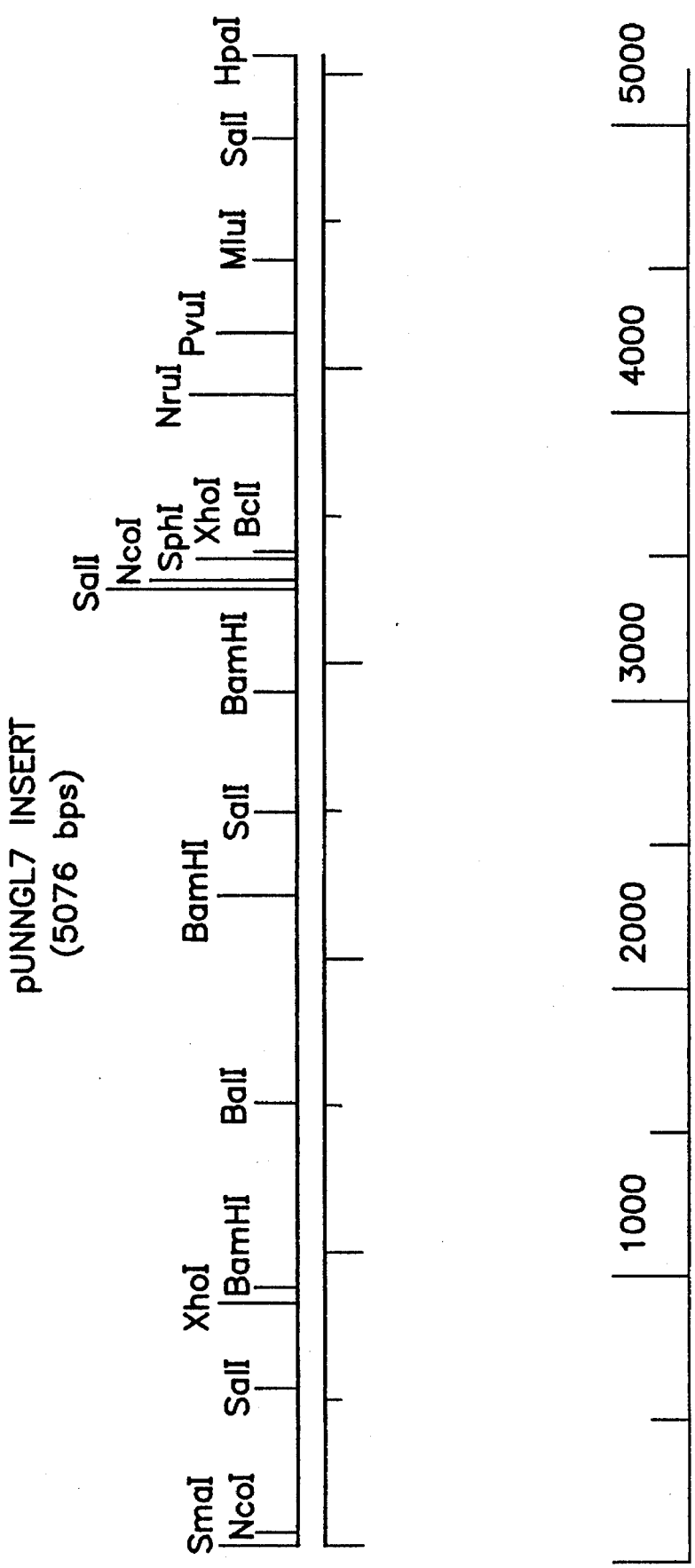
FIG. 6: insert of pUNNGL7 harboring the Pseudomonas SY-77 glutaryl-Cef acylase gene.
Figure 7:
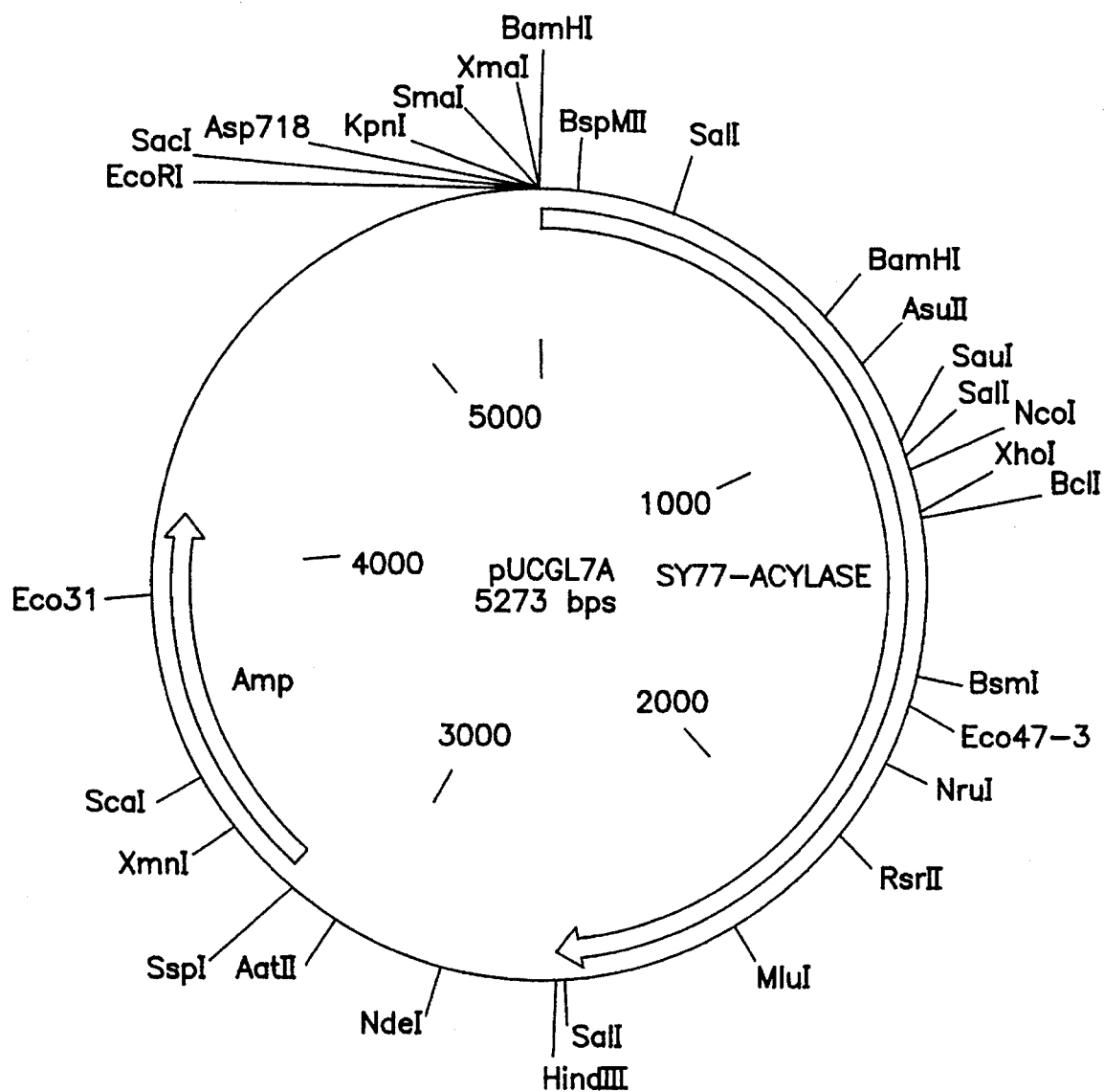
FIG. 7: restriction map of plasmid pUCGLTA: plasmid pUC18 harboring the glutaryl-Cef acylase gene of Pseudomonas SY-77.

The hybridizing plasmid pUNNGL-7 was shown to harbor the acylase encoding fragment of Pseudomonas SY-77 by restriction mapping (FIG. 6). This plasmid was purified and partially digested with BamHI and SmaI. Fragments of 2.6 kb were purified from agarose gel (Geneclean) and ligated into BamHI, SalI linearized pUC18 (Pharmacia). The resulting plasmid was characterized as shown in FIG. 7. Colonies were grown in LBC medium and analyzed for acylase activity (see Methods). It was shown that plasmid pUCGL-7A produces 5 Units/g cell pellet.

The same BamHI-SalI fragment was also cloned into plasmid pTZ19R (Pharmacia) resulting in plasmid pTZ19GL-7A. The total DNA sequence of the 2.6 kb BamHI-SalI fragment was determined (see FIG. 13) and the complete amino acid sequence of SY-77 acylase was derived. The first 311 residues (out of the total of 850) are identical to the published partial sequence of SY-77 acylase (Matsuda [29], ibid.).

connecting peptide (FIG. 14A) and [β]-subunit (FIG. 14B) are starting. These positions were deduced from the peptide-sequencing data summarized in Table 2. Where no peptide sequencing data were available, positions were deduced from the corresponding positions in E. coli.

TABLE 2

Peptide sequencing data of α- and β-subunits of Type-II acylases

| | α-subunit | | | | β-subunit | | |
|---|---|---|---|---|---|---|---|
| Enzyme | N-terminus | | c-terminus | | N-terminus | | Ref. |
| E. col | H$_2$N—EQSSS | (SEQ ID NO: 13) | QTA—COOH | (SEQ ID NO: 14) | H$_2$N—SNM | (SEQ ID NO: 15) | [10] |
| E. col | H$_2$N—EQSSSEI | (SEQ ID NO: 16) | NQQNSQTA—COOH | (SEQ ID NO: 17) | H$_2$N—SNMWVIG | (SEQ ID NO: 18) | [31] |
| K. cit | H$_2$N—ASPPTEVK | (SEQ ID NO: 19) | TQTA—COOH | (SEQ ID NO: 20) | H$_2$N—SNMWVIGK | (SEQ ID NO: 21) | [11] |
| A. fae | H$_2$N—Q?Q?VEVM?T | (SEQ ID NO: 22) | not determined | | H$_2$N—SNLWST?PE?V | (SEQ ID NO: 23) | |
| SE-83 | H$_2$N—TMAAKT | (SEQ ID NO: 24) | not determined | | H$_2$N—SNNWA | (SEQ ID NO: 25) | [8] |
| SY-77 | H$_2$N—EPTSTPQA | (SEQ ID NO: 26) | not determined | | H$_2$N—SNS?AVA | (SEQ ID NO: 27) | [29] |

The homologies between the amino acid sequences were calculated for the (putative) α-subunits and the β-subunits (Tables 3 and 4, respectively).

EXAMPLE 4

Cloning of a Pseudomonas Glutaryl-Cephalosporin Acylase Gene (B)

Pseudomonas SE-83 produces an acylase capable of hydrolyzing glutaryl amidocephalosporanic acid and cephalosporin C into 7-ACA and glutaric acid. A gene encoding the responsible enzyme was cloned from the chromosomal DNA of Pseudomonas SE-83 (AcyII in Matsuda [30]). From these data it was decided to clone a 6.0 kb BglII fragment of Pseudomonas SE-83 into BclI linearized pUN121 (Nilsson [20]). Resulting transformants in JM101 were hybridized with an oligonucleotide (SEQ ID NO: 12) derived from the DNA sequence of AcyII (Matsuda [30], ibid.):

```
CGG CCG ATG CTC CTC GCC CCA GCC GCG CCC GGT
    CAG GTT CTG CGT CGC GAC GGA
```

Figure 8:
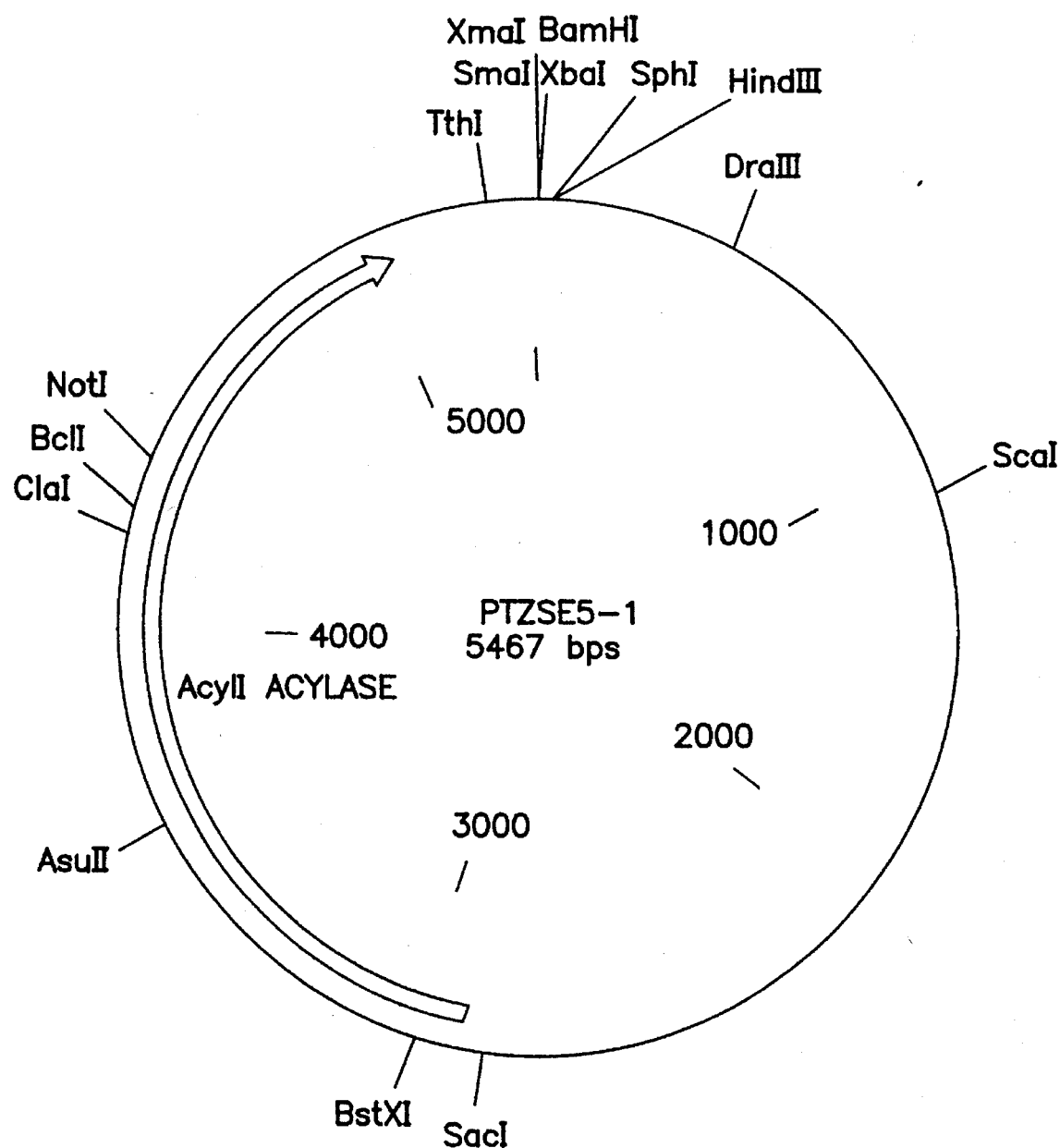
FIG. 8: restriction map of plasmid pTZSE5-1: plasmid pTZ18R harboring the Pseudomonas SE-83 AcyII gene.

A positive clone, pUNSE-5, was isolated. A 2.3 kb SacI-SmaI fragment of plasmid pUNSE-5 was purified and subcloned into vector pTZ18 to give pTZ18SE5-1 (FIG. 8).

EXAMPLE 5

Homology Comparison of Type-II Acylases

In FIGS. 14–14C the amino acid sequence of the precursor form of various acylases are aligned, with respect to the sequence of the acylase of Escherichia coli.

The acylases originating from Escherichia coli (E.col), Kluyvera citrophila (K.cit) and Alcaligenes faecalis (A.fae) are Type-IIA acylases (PenG acylase), whereas the acylases from Pseudomonas (SE-83 and SY-77) are the Type-IIB acylases (glutaryl-Cef acylase).

Also indicated in FIG. 14 are the positions where the leader (signal sequence, FIG. 14A), [α]-subunit (FIG. 14A),

TABLE 3

Homology matrix of the α-subunits of Type-II acylases

| | 1. | 2. | 3. | 4. |
|---|---|---|---|---|
| Type-IIA | | | | |
| 1. E. col | 100 | | | |
| 2. K. cit | 83(89) | 100 | | |
| 3. A. fae | 47(60) | 46(61) | 100 | |
| Type-IIB | | | | |
| 4. SE-83 | 26(38) | 26(45) | 32(42) | 100 |
| 5. SY-77 | 30(40) | 29(42) | 28(38) | 25(32) |

TABLE 4

Homology matrix of the β-subunits of Type-II acylases

| | 1. | 2. | 3. | 4. |
|---|---|---|---|---|
| Type-IIA | | | | |
| 1. E. col | 100 | | | |
| 2. K. cit | 86(91) | 100 | | |
| 3. A. fae | 41(56) | 41(55) | 100 | |
| Type-IIB | | | | |
| 4. SE-83 | 22(35) | 23(36) | 27(34) | 100 |
| 5. SY-77 | 26(35) | 27(39) | 22(32) | 28(36) |

The values in parentheses denote the homology based on similar residues whereas the values in front of the brackets are for identical residues.

It can be seen from Tables 3 and 4 that there is a high degree of homology within the Type-IIA acylases ranging from 46–83% for the α-subunits to 41–86% for the β-subunits. This becomes even higher if similarity between residues (e.g. Ser/Thr, Asp/Glu, Arg/Lys etc.) is taken into account. This high degree of homology suggests that the 3D-structure of the three PenG acylases will be very similar.

The homology between Type-IIA and Type-IIB acylases is lower (22–30%). Again these values become higher if the similarity between amino acids is taken into account (35–45%). Therefore, the Type-IIB acylases appear to be structurally related to the Type-IIA acylases. The homology is not equally distributed over the amino acid sequences, but certain areas of high homology do occur.

The determination of the sequences of the *Alcaligenes faecalis* and Pseudomonas SY-77 acylases makes it possible to identify residues which may be directly involved in catalysis.

The observation that Type-II acylases are inhibited by PMSF suggests strongly that an activated serine is involved in catalysis. Activated serines have been observed in serine proteases, and in lipases. They are always found together with a histidine and an aspartic acid, forming a catalytic triad.

The alignment of the sequences in FIGS. 14A–14C shows only 3 conserved serines: Ser174, Ser266 and Ser765 (*A. faecalis* numbering).

Ser174 is located in the α-subunit in a rather well conserved region within the Type-IIA acylases which, however, is poorly conserved in the Type-IIB acylases (FIGS. 14A–14C). Taking also into account the experimental observation that the PMSF-sensitive amino acid is located on the β-subunit (Daumy [12]), Ser174 is unlikely to be the active site serine.

Ser266 is located at the N-terminus of the β-subunit and most likely conserved because it is essential for the maturation of the enzyme. It is therefore also an unlikely candidate to be the active site serine.

Ser765 is located on the β-subunit (confirming the experimental result that the PMSF-sensitive amino acid is located at the β-subunit) and therefore very likely the active site serine. The consensus sequence around this serine is . . . -Gly-XXX-Ser- . . . .

The glycine preceding the serine is common to all serine hydrolases (Blow [14]).

Two different histidines are conserved throughout the five sequences (FIGS. 14A–14C): His42 and His777. They both are in a region which is highly conserved in all sequences. His777, however, is rather close to the postulated active site serine at position 765 and therefore an unlikely candidate. On the contrary, His42 is in a region of high homology. Assuming that this His42 is the active site histidine, being localized on the α-subunit, is also in accordance with the experimental observations that only the heterodimer is the active form of the enzym (i.e. the serine on the β- and the histidine on the α-subunit).

With respect to the third residue of the proposed catalytic triad, there are three candidates found in the β-subunit: Asp448, Asp590, Asp780 and one in the α-subunit: Asp36. The latter is contained at the start of a highly conserved region, yet close to the proposed active site His42. Similarly, the Asp780 is contained in a highly conserved region, but close to the proposed active Ser765. Asp448 and Asp590 are both in a moderately conserved region and therefore both are likely candidates to be the active site aspartic acid.

EXAMPLE 6

Selection of Residues for Mutagenesis Based on Type-IIA Acylases

In this Example the amino acid residues are selected which may be mutated in order to obtain acylases with altered biochemical properties. These altered properties may result in an alteration of the substrate specificity of Type-II acylases towards the acylation and/or deacylation of certain β-lactam antibiotics.

The criteria for the selection are outlined while at the same time reference is made to FIGS. 15A–15B and 16A–16D which contain all selected positions. For reasons of simplicity, the residues given are those for the Type-IIA acylase from *Alcaligenes faecalis*. The corresponding residues in the other acylases may be found using the aligned sequence data from FIGS. 14A–14C.

The selection of the regions for mutagenesis was based on the following criteria:

1) In order to change the substrate specificity of the Type-II acylases, the mutations were restricted to the mature α- and β-subunits. This means residues 27–236 (α-subunit) and 266–816 (β-subunit), resulting in a total of 210 and 551 residues, respectively.

2) The amino acids of the PenG-acylases (Type-IIA) which are binding the hydrophobic phenylacetyl side-chain of PenG will be conserved in the Type-IIA acylases and, due to the different substrate specificities, probably not in the Type-IIB acylases. Therefore, from the α- and β-subunits those residues are preferably selected which, in the alignment of FIGS. 14A–14C, are identical or similar in the Type-IIA acylases from *E. coli*, *Kluyvera citrophila* and *Alcaligenes faecalis*.

A position is said to contain a similar amino acid residue when the residues found at that position belong to one of the following groups:

a) Hydrophobic residues—This group includes the amino acids isoleucine, valine, leucine, cysteine, methionine, alanine, phenylalanine, tryptophan and tyrosine.

b) Small, non-bulky residues with a high propensity to be in a flexible segment—This group includes alanine, glycine, serine, threonine, proline, valine and cysteine.

c) Polar or charged residues—This group includes serine, threonine, histidine, glutamine, asparagine, aspartic acid, glutamic acid, arginine and lysine.

The number of positions to be considered for mutagenesis in the α-subunit is restricted by these selection criteria to 169 (80%) and in the β-subunit to 416 (75%). In FIGS. 15A–15B and 16A–16D these selected residues are summarized in the columns with heading 1. The numbers refer to the positions of the respective amino acids in the sequence of the *Alcaligenes faecalis* acylase as given in FIG. 14.

3) A preferred group is selected based on the assumption that, since the interactions between the PenG-acylase and the side chain of PenG are supposed to be highly hydrophobic in nature, only those conserved and similar amino acids may be selected which are not charged. This means omission of any selected position that contains at least one charged residue in a conserved or similar set as defined above for group c. This selection criterion further restricts the number of preferred amino acid positions in the α-subunit to 119 (57%) and the β-subunit to 304 (55%). FIGS. 15A–15B and 16A–16D summarize these residues in the columns with the heading 2.

4) A further preferred group is selected based on the observation that conserved glycine and proline residues usually fulfill a structural role in a protein rather than a catalytic one. Leaving out the conserved Gly's and Pro's from the selected set of amino acids, results in a more preferred group consisting of 102 amino acids in the α-subunit (49%) and 258 in the β-subunit (47%)—FIGS. 15A–15B and 16A–16D summarize this group under heading 3. This set of amino acids consists therefore of conserved and similar residues with the exception of the charged amino acids, conserved glycines and conserved prolines.

5) A still more preferred group of selected amino acids is obtained on the assumption that it is also less probable that polar amino acids such as glutamine, asparigine, threonine, serine and others are involved in the binding of the hydrophobic substrate. Using this further selection criterion 74 amino acids in the α-subunit (35%) and 162 in the β-subunit (29%). FIGS. 15A–15B and 16A–16D summarize these under the heading 4. This set of amino acids consists only of identical and similar hydrophobic amino acids as they are defined above under a) in paragraph 2.

6) Yet a further selection of amino acids to be mutated or capable of being mutated is made on the assumption that the binding site of the Type-IIA acylases is composed of identical hydrophobic amino acids. This reduces the number of selected amino acids further to a final set of 44 conserved, hydrophobic amino acids in the α-subunit (being 21% of the total number of amino acids in the α-subunit) and of 81 conserved, hydrophobic amino acids in the β-subunit (15% of the total in the 5-subunit). Columns 5 in FIGS. 15A–15B and 16A–16D show this selected set of amino acids.

EXAMPLE 7

Selection of Residues for Mutagenesis Based on Differences in Polarity Between Type-IIA and Type-IIB Acylases Type-IIB acylases are specific for substrates containing dicarboxylic acids as the acyl moiety, such as succinic, glutaric and adipic acid. This suggests that the binding site is much more polar as compared with the Type-IIA acylases. It might even contain a positive charge to compensate for the negative charge on the substrate side acyl moiety. These features are expected to be conserved among the enzymes revealing this substrate specificity. Therefore, the Type-IIA and Type-IIb acylase sequences were compared in order to find regions which are conserved in both the Type-IIA and the Type-IIB acylase sequences but which have changed polarity in order to obtain a more favorable binding of the negatively charged acyl moiety.

The criteria for the selection are outlined while at the same time reference is made to FIGS. 17A–17F which contain all selected positions. The residues given are those for the Type-IIB acylase SY-77. The corresponding residues in the other acylases can be found using the aligned sequence data from FIGS. 14A–14C.

Identification of regions which are conserved in type IIB acylase was performed according to a similar procedure as described in Example 6 for the Type-IIA acylases:

1) Mutations were restricted to the mature α- and β-subunits. This means residues 30–198 (α-subunit) and 199–720 (β-subunit).

2) Select those positions in Type-IIB acylases which contain identical or similar amino acid residues according to the grouping in Example 6. The selected residues are summarized in FIGS. 17A–17F in the columns with heading 1.

3) The further selection is based on the assumption that the interactions between the PenG-acylases (Type-IIA acylases) and the side chain of PenG are highly hydrophobic in nature while for the glutaryl acylase a more polar binding site is assumed which may even harbor positively charged residues. Therefore all positions in the alignment of FIGS. 14A–14C which show charge in both the Type-IIA and the Type-IIB acylases were omitted. Only in situations where Type-IIA acylase show an Asp or a Glu while Type-IIB acylases show unambiguously much less negatively charged residues, the position is maintained. Application of this selection further restricts the number of preferred amino acid positions. FIGS. 17A–17F summarize these residues in the columns with the heading 2.

4) A further selection was made by leaving out the conserved Gly's and Pro's from the selected set of amino acids as discussed before in Example 6. See FIGS. 15A–15B and 16A–16D for a summary of this set of amino acids under heading 3.

5) A further narrowing of the selected amino acids may be obtained by supposing that in Type-IIB glutaryl-Cef acylase it is less likely that hydrophobic amino acids involved in the binding of the negatively charged glutaryl side chain. Therefore positions within the Type-IIB acylases which contain identical or similar hydrofobic residues were omitted from the collection which has remained after step 4. FIGS. 17A–17F summarize the results under the heading 4.

6) The set of residues which has remained contains mainly polar or charged residues. Yet a further selection of amino acids to be mutated or capable of being mutated may be made by assuming that positions which show polar residues in Type-IIA and Type-IIB are likely surface residues not necessarily involved in substrate binding. Therefore these residues were omitted in step 5 in FIGS. 17A–17F.

7) In step 7 those positions were selected which accommodate residues that unlike residues at the corresponding position in Type-IIA acylases may fit in electrostatically with a negatively charged glutaryl side chain. In particular sites which are hydrophobic in Type-IIA and positively charged in Type-IIB acylases were selected for mutagenesis.

EXAMPLE 8

Construction of an Expression/Mutagenesis Vector System for Acylase Genes

For the purpose of mutagenesis plasmid pTZ19GL-7A was grown in single stranded DNA form according to the supplier. The following oligonucleotide (SEQ ID NO: 28) was used to introduce a NdeI site (CATATG) at the ATG start codon:

CAG AAC TCT CAG CAT ATG TTT CCC CTC TCA

Figure 9:
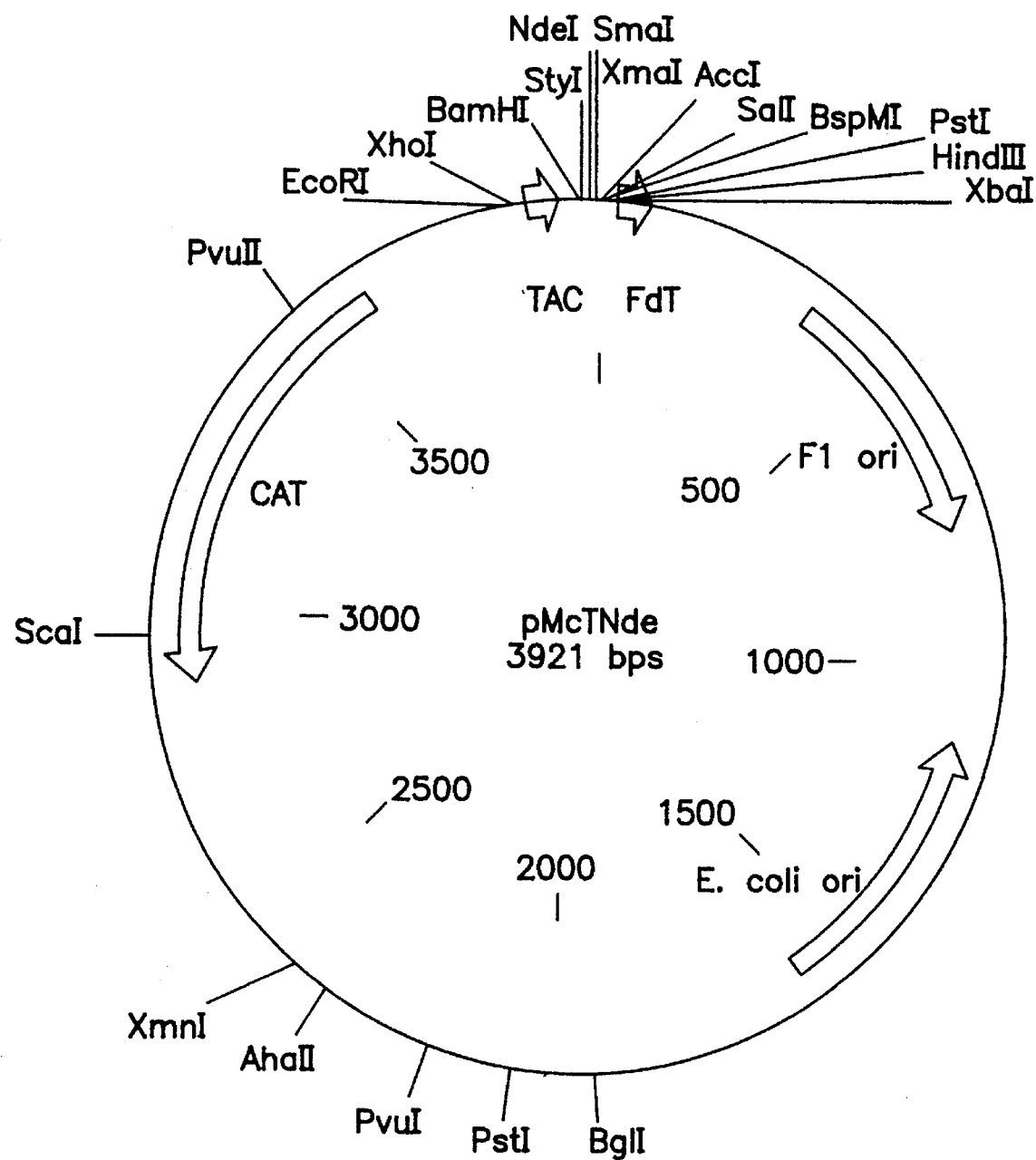
FIG. 9: map of plasmid pMcTNde: a derivative of the mutagenesis expression plasmid pMa/c 5–8 with a NdeI insertion position under control of the TAC promoter.

To enable efficient site-directed and region-directed mutagenesis the NdeI-HindIII fragment of the resulting mutant was subcloned into pMcTNde, a derivative of plasmid pMc-5 (Stanssens [22]). Plasmid pMcTNde was derived from pMc5–8 (EP-A- 0351029) by insertion of a fragment encoding the TAC promoter followed by a RBS site and a NdeI cloning site (FIG. 9).

Figure 10:
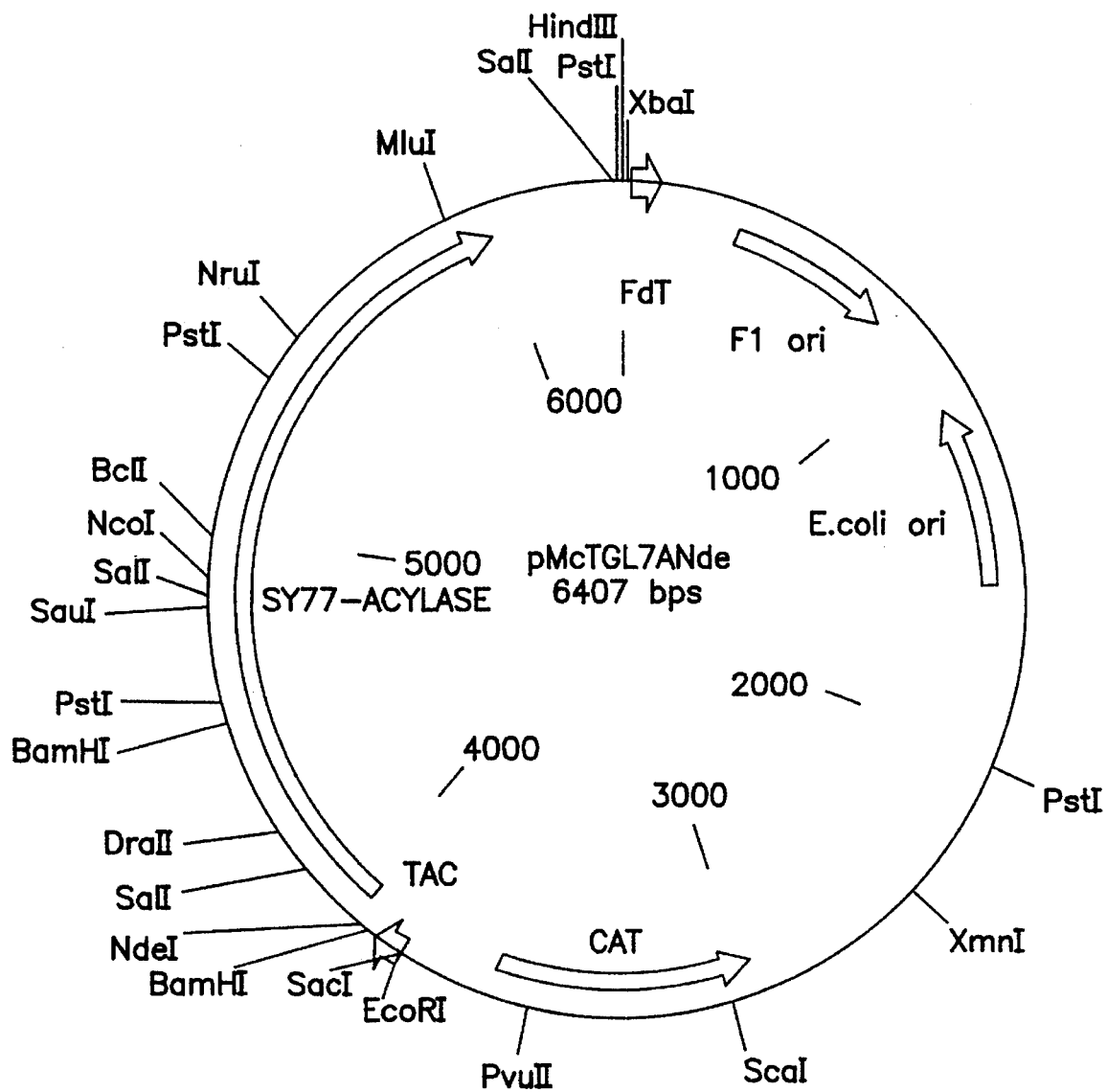
FIG. 10: map of plasmid pMcTGL7ANde, with the SY-77 glutaryl-Cef acylase gene inserted into the NdeI site (harboring the start codon) of plasmid pMcTNde.
Figure 11:
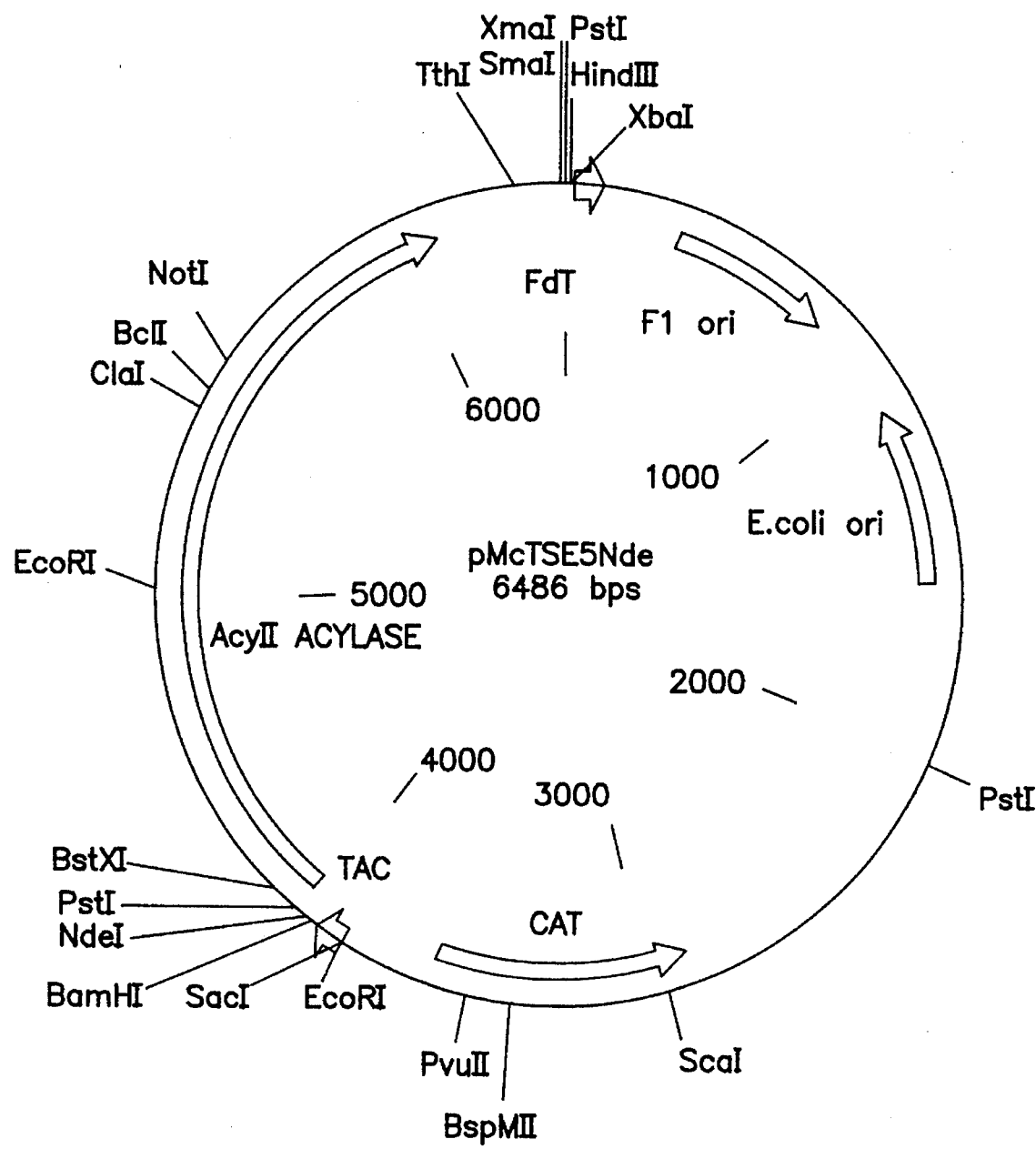
FIG. 11: map of plasmid pMcTSE5Nde: plasmid pMcTNde with the/SE-83 AcyII gene inserted in the NdeI site.

In a similar way plasmid pTZSE5-1 was mutagenised with the following oligonucleotide (SEQ ID NO: 29):

AGG TCC AGA CAG CAT ATG ACG ATG GCG to create a NdeI site at the position of the start codon of the acylase gene. The NdeI-SmaI fragment of the resulting mutant was also transferred into plasmid pMcTNde which was cleaved with NdeI and SmaI. The resulting plasmids pMcTGL7ANde (FIG. 10) and pMcTSE5Nde (FIG. 11) direct the synthesis of SY- 77 and SE-83 glutaryl-Cef acylase activity, respectively, under the guidance of the strong inducible TAC promoter (De Boer [23]).

Expression levels in *E. coli* WK6 in LBC medium are 2.2 and 12.3 Units/g cell pellet, respectively.

Figure 12:
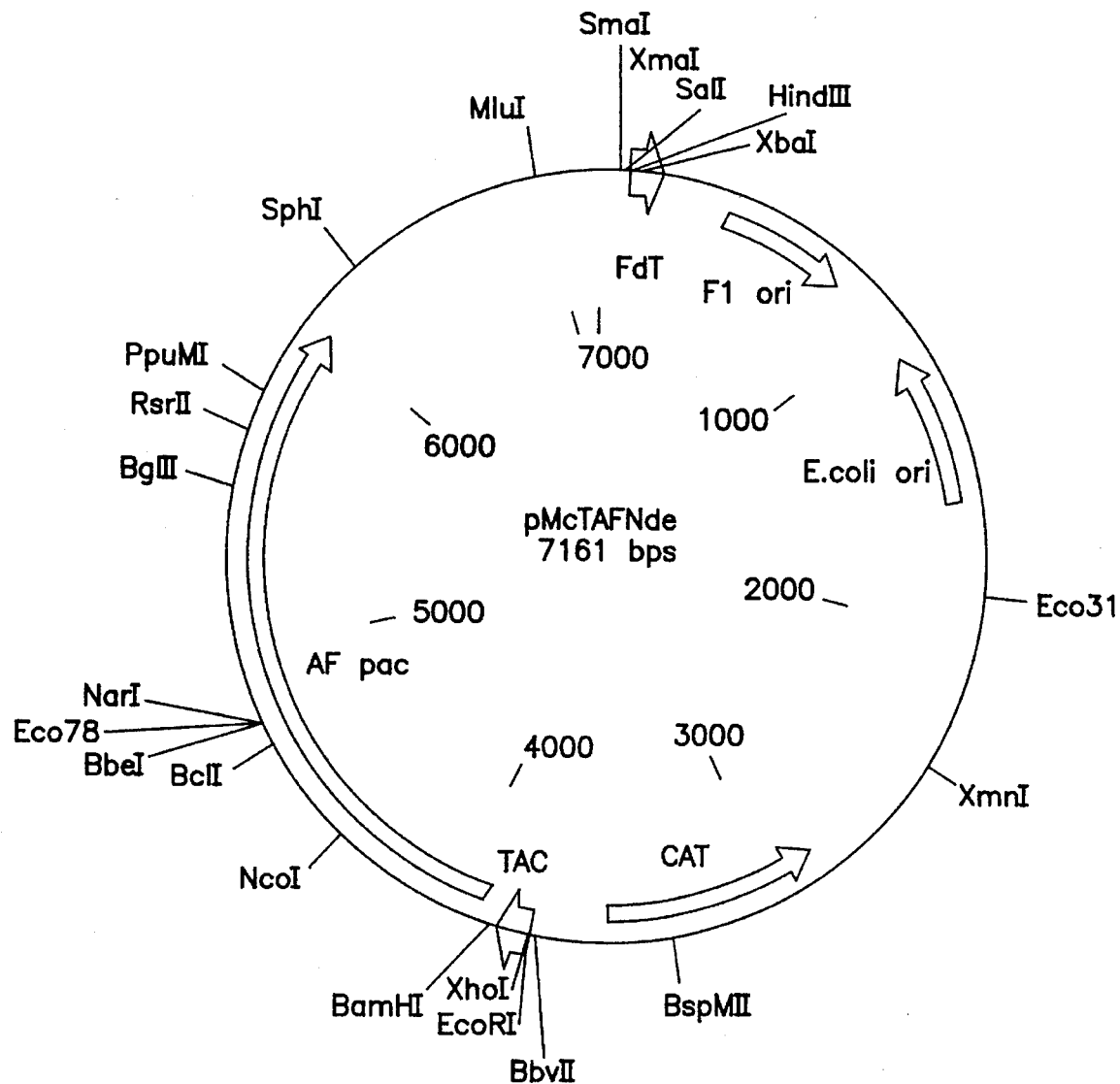
FIG. 12: map of plasmid pMcTAFNde: plasmid pMcTNde with the *A. faecalis* penicillin acylase gene inserted in the NdeI site.

The sequence of the complete acylase encoding region of plasmid pMcTGL7ANde was determined. The result is shown in FIG. 12.

EXAMPLE 9

Mutagenesis of SY-77 Acylase

Plasmid pMaTNdeGL7A was digested with NdeI and NcoI. A gapped duplex with single stranded pMcTNdeGL7A was made and enzymatic mutagenesis on the single stranded gap was performed as described (Methods). The resulting mutant library was transformed into *E. coli* WK6 MutS and subsequently transformed into *E. coli* HB101 and selected on aminoadipyl leucine containing minimal plates suplemented with 50 µg/ml cap. Those colonies that were able to grow on these plates and not on minimal plates (because these were leucine revertants) were tested for enzymatic activity on Cephalosporin C. For region directed mutagenesis, spiked oligo's covering various portions of the α-subunit of the acylase gene were incorporated in the same manner as in the site directed mutagenesis protocol (Stanssens [22]).

The following oligonucleotides were used with 2% contamination included during synthesis. Each of the oligo's was designed to harbor a silent mutation allowing the discrimination of wild-type and mutant plasmids based on the occurence or disappearance of a restriction enzyme recognition site. The residues of SY-77 acylase covered by the respective oligonucleotides is given in parenthesis.

reversion to prototrophy and for linkage of growth capability and the presence of plasmid.

The following mutants with good growth capability on adipyl serine were selected:

| Spiked oligo | Mutation (DNA) | Mutation (Amino Acid) |
|---|---|---|
| AB 2237 | GTA → CTA | V62L |
| AB 2236 | TAT → CAT | Y178H |
|  | GTC → GGC | V179G |
|  | CTC → ATC | L177I |
|  | TAT → CAT | Y178H |

These mutant plasmids were used as starting material for a next round of mutagenesis using spiked oligo's of the α-subunit with a subsequent selection on aminoadipyl leucine (library construction in *E. coli* HB101).

Since the residues 177, 178 and 179 were identified as crucial for the substrate specificity of SY-77 acylase an approach of targeted random mutagenesis can be applied. For this purpose the following mixed oligonucleotide (SEQ ID NO: 35) for Targetted Random Mutagenesis on residues 176, 177, 178, 179 and 180 was synthesized:

AB2237 (residue 50–80) (SEQ ID NO: 30)
GCCCTGGCTGCGCGCCTGGGCCCAGCCATAGCCGTAGAAGGCTGAGGGC
GCGTCTACGCCGTAGATGTGCGGGACGCCGTAGCCGTCCCACAG AB2233 (residue 81–109) (SEQ ID NO: 31)
CCAGACGGTCGTCTGTTCGTAATCCGGTCCCCAGTATTCGGCC
CCCTTGCCCCGCGCTTCTCCATACAGGCGCAGGATATTGTC AB2234 (residue 109–136) (SEQ ID NO: 32)
GAATGCGTCGAGGTTGGCGCGGAAATCAGGCGACTGCTGCGCATACC
ACTGCTGAGCGCGCTCCGGCACGCCGTTGGTCAGCAG AB2235 (residue 137–164) (SEQ ID NO: 33)
GGCGCCGGAAACCGGCAGCACCTGCCGCACGTCGGGCGAGA
TGTCGTCGGGGTTCTGCTGCGCATAGGCGTTGATGCCCGCTGC AB2236 (residue 165–192) (SEQ ID NO: 34)
CGGCGGGTCGCCCTCGCCCAGGGTGCGCCCGGGCGACGCGACATA
GAGGAAGTTCATCAGGCGGTGGGCGTGGGCCACCACGTC For each oligonucleotide a mutant library of >10⁵ independent colonies in *E. coli* WK6 mutS was constructed. These libraries were transformed into *E. coli* PC2051 for

```
187
GCC CAG GGT GCG GCC GGG CGA NNN NNN NNN
                                                         168
                        NNN NNN GTT CAT CAG GCG GTG GGC GTG GGC
``` selection on adipyl serine and into *E. coli* HB101 for selection on aminoadipyl leucine. Colonies selected for growth during 10 days at 30° C. were subsequently tested for The same strategy can be applied to the region 60–64 with the following oligo (SEQ ID NO: 36):

```
                71
ATA GCC GTA GAA GGC TGA GGG NNN NNN NNN
                                                              53
                        NNN NNN GAT GTG CGG GAC GCC GTA GCC
```

Mutant libraries of $10^6$ mutants were generated with the above-mentioned oligonucleotides in E. coli HB101 and selected on aminoadipyl leucine plates.

Targeted random mutagenesis was also performed on the same gapped duplex molecule using the following oligo:

```
GCTGCGCGCCTGNNNNNNNGCCNNNGCCNNNGAANNNTGAGGGCGCGTC
```

This results in a substitution of amino acid positions 67, 69, 71, 73 and 74 of SY-77 acylase into all possible 20 amino acids. A mutant library of $10^7$ mutants was generated and selected on aminoadipyl leucine plates.

A similar approach as described above for the α-subunit was applied on selected regions of the SY-77 acylase β-subunit. Based on the sequence comparison and selection criteria as described above the following regions were selected for spiked oligo mutagenesis with the following oligonucleotides, respectively:

AB2399 (residue 253–277) (SEQ ID NO: 38)
ATAGTTGGTGGCCCCCACCATGCCGTTAACGGTATTGGTGATGCCCATCC
GCTGGTTGAAGGCGAAGCGGATGAC AB2400 (residue 375–399) (SEQ ID NO: 39)
CTCGGCCCGTTTGGGCGCCACGCCGTTGAAGCTGTAGTTGATGGTA
CCTTCGCGGTCGGCGTAGACGATGTTGAA AB2401 (residue 415–442) (SEQ ID NO: 40)
ATTGGAATTCTGCACGAAGCCGCCCGGCGGATTGGTGACGCGCGG
CAGATCGTCCAGCGGGTGTGTCTCGGTCCACAGGTAACG AB2402 (residue 505–529) (SEQ ID NO: 41)
CAGCAGGCGCGCCGCCGCCTGGACCTCGGGATCGGGATCGATCAGG
GCGGCCGGGATCAGGTCCGGCAAGGTGCG AB2403 (residue 668–695) (SEQ ID NO: 42)
GTCGGCGCGCGACACGCGTTCGATCTGATCGCTGTAGTGCGTCG
TGCCCGGGTGGCGAGAGTTGCCGTAGCTCATCAGGCCATA With these oligo's mutant libraries for specific regions of the β-subunit were generated and selected on adipyl serine or aminoadipyl leucine.

Oligo AB2403 encompasses the region around Ser674 which is identified on the basis of sequence comparison with among other A. faecalis Pen-acylase and SY-77 acylase as a candidate for the catalytic serine residue. Mutations around this region are expected to be close to the catalytic site which enhanced the possibility of a change in substrate specificity.

EXAMPLE 10

SY-77 Acylase Mutants with Increased Specificity for Adipyl Serine

Mutants were transformed into a serine auxotroph of E. coli and selected by their ability to grow on a minimal medium which contained adipyl serine as a sole source of carbon. Cells which contained wild-type SY-77 glutaryl acylase did only grow very poorly on such a medium. No significant colonies were observed within 14 days. Colonies which developed within 14 days were selected from the plates and it was verified that they did not grow when adipyl serine was omitted from the plates. Next plasmid DNA was isolated from the selected colonies and transformed to native E. coli cells. It was checked that transformant cells still did grow on the selective medium containing adipyl serine. The following mutants were obtained: V62L, Y178H, V179G and L177I+Y178H.

Figure 18:
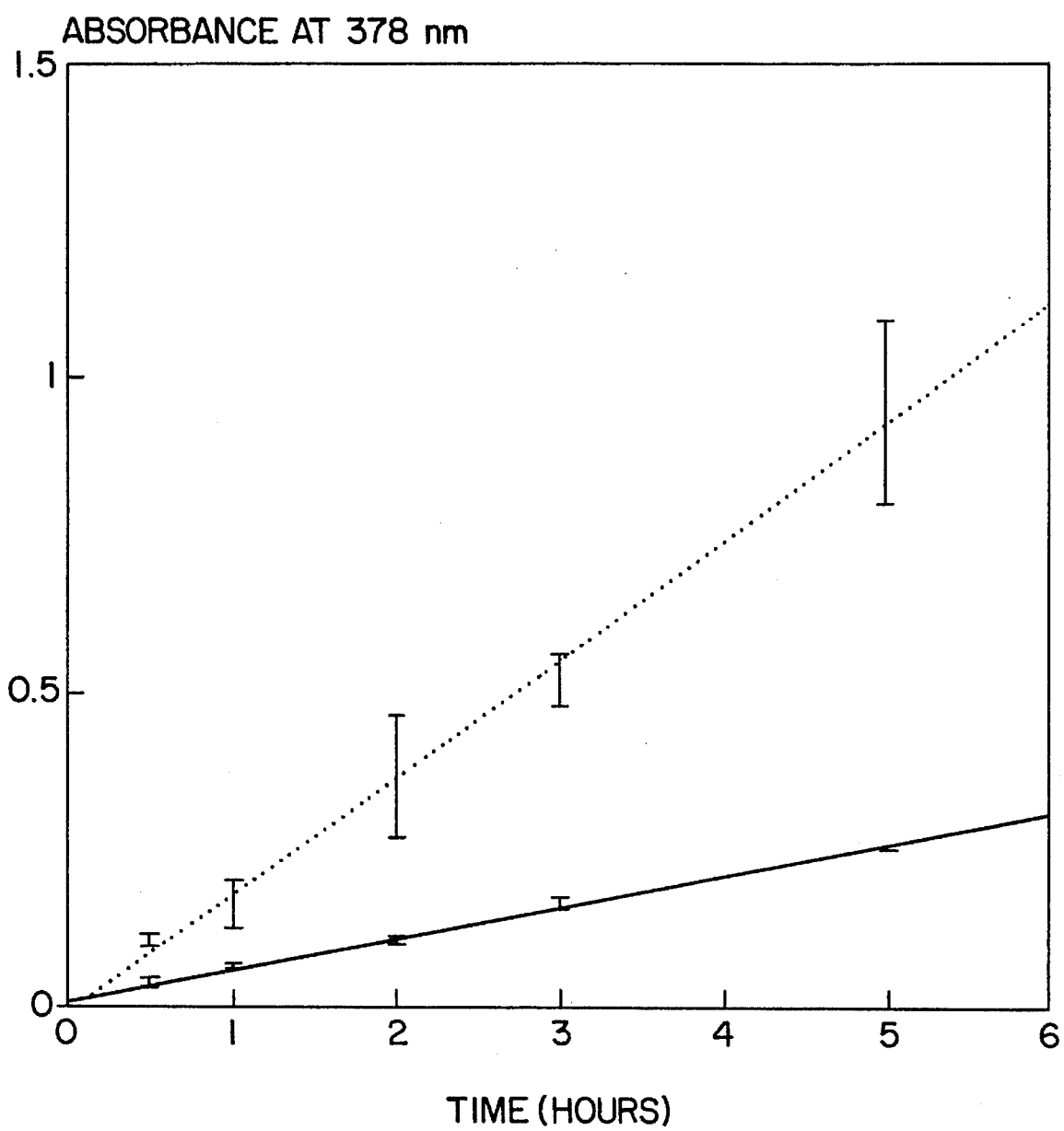
FIG. 18: conversion of adipyl serine by glutaryl acylase SY-77 wild-type and mutant V62L. Enzymes were dosed in such a way that the same activity on glutaryl 7-ACA was obtained. Wild type: solid line; Val 62 Leu: dotted line.
Figure 19:
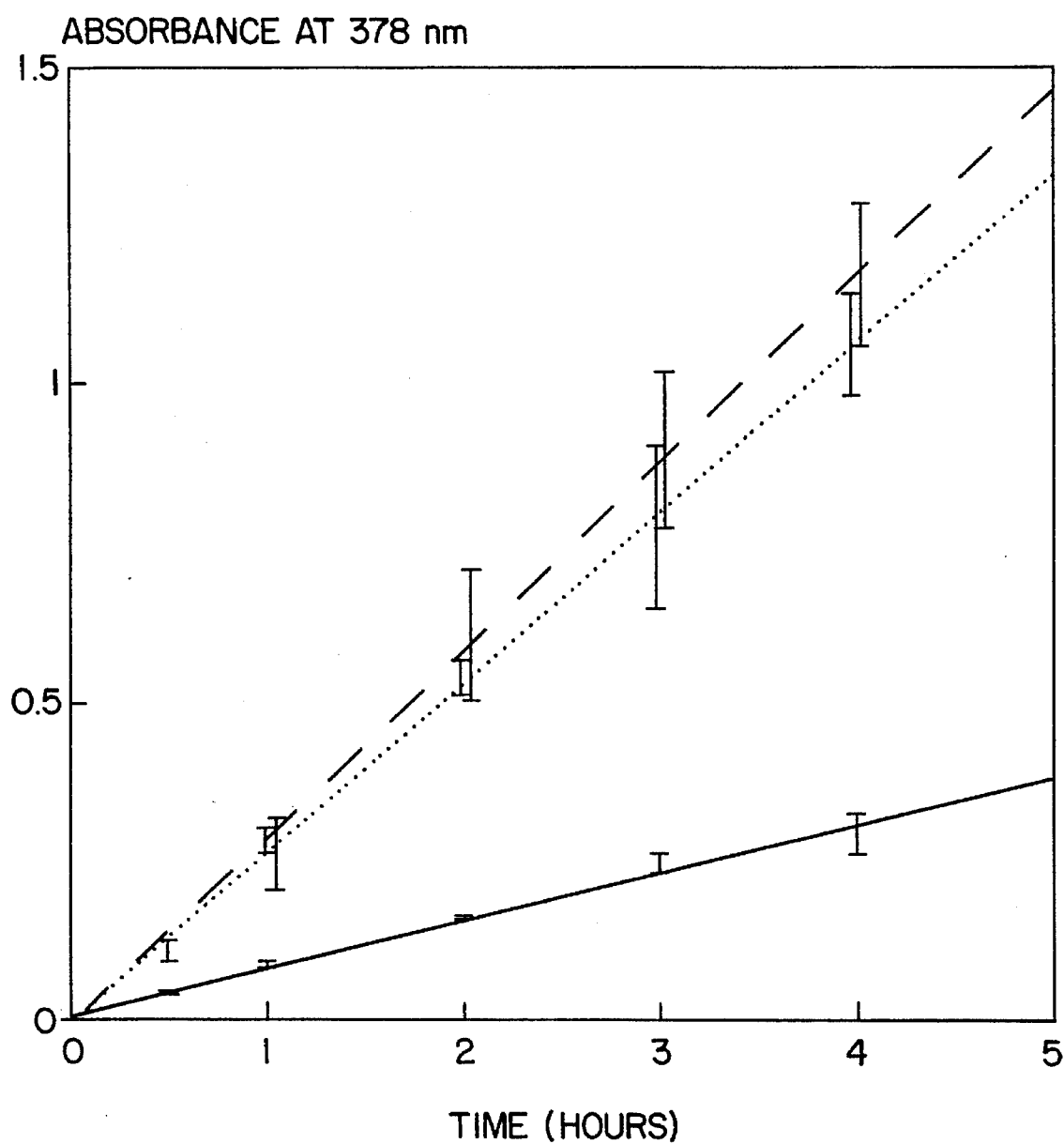
FIG. 19: conversion of adipyl serine by glutaryl acylase SY-77 wild-type and mutants Y178H and V179G. Enzymes were dosed in such a way that the same activity on glutaryl 7-ACA was obtained. Wild type: solid line; Tyr 178 His: dotted line; Val 179 Gly: dashed line.
Figure 20:
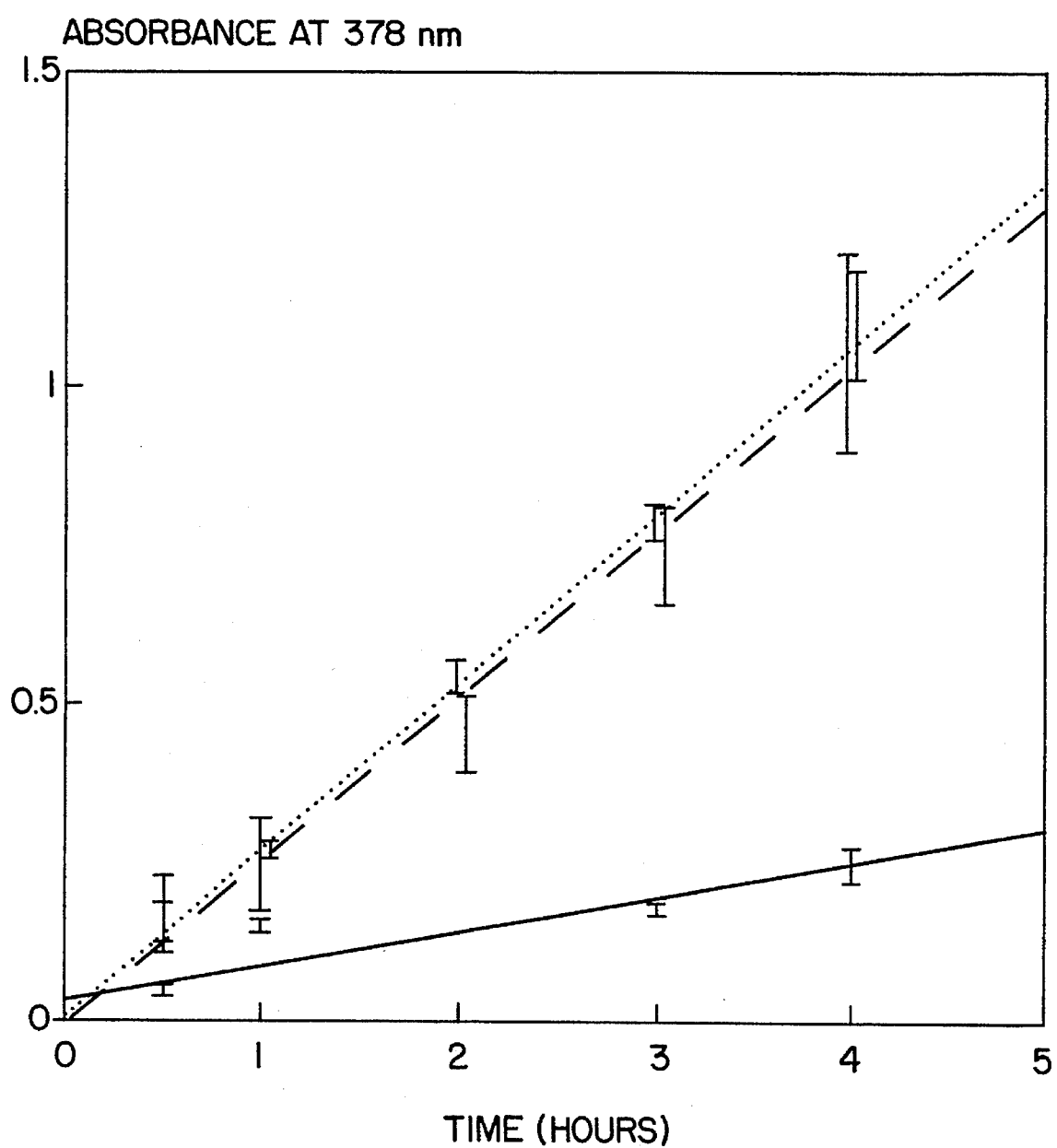
FIG. 20: conversion of adipyl serine by glutaryl acylase SY-77 wild-type and mutants Y178H and L177I+Y178H. Enzymes were dosed in such a way that the same activity on glutaryl 7-ACA was obtained. Wild type: solid line; Tyr 178 His Leu 177 Ile: dotted line; Tyr 178 His: dashed line.

Wild-type SY-77 glutaryl acylase and mutant SY-77 glutaryl acylases were assayed with glutaryl 7-ACA, glutaryl leucine and adipyl serine as substrates. Hydrolysis of the substrates was followed by measuring the release of 7-ACA, leucine or serine with fluorescamine at 378 nm. In the activity assays with glutaryl leucine and adipyl serine the mutants and the wild-type enzyme were dosed according to their activity on glutaryl 7-ACA. FIGS. 18–20 show the rate of hydrolysis with adipyl serine for the given mutants. The hydrolysis was followed in time by measuring the increase in absorption at 378 nm upon reaction of fluorescamine with the released serine. The mutants showed a 3 to 5 times higher activity on adipyl serine than the wild-type SY-77 glutaryl acylase. Since the wild-type grows very slowly when adipyl serine is the sole carbon source, it can be concluded that the SY-77 acylase mutants disclosed have a higher specificity on this substrate.

For glutaryl leucine the same assay procedure was followed as for adipyl serine in order to compare activity of mutants and wild-type. Glutaryl leucine is a suitable substrate to check whether mutations affect the specificity for the acyl side chain or for the complementary side, such as the β-lactam moiety or the amino acid. If mutations affect the specificity for the acyl side chain then the activity of wild-type and mutant glutaryl acylase are likely to show the same tendency for substrates such as glutaryl 7-ACA and glutaryl leucine. Because in the assays enzymes are dosed according to their glutaryl 7-ACA activity this implicates that activities on glutaryl leucine should be very similar for mutants and wild-type. Indeed within the error of the measurement all mutants coincide with wild-type activity which indicates that the mutations affect the specificity for the acyl side chain, more specifically increase the specificity for the adipyl moiety.

EXAMPLE 11

Mutagenesis of Pseudomonas SE-83 Acylase

Region-directed and targeted random mutagenesis of pMcTSE5Nde was performed after creation of a gapped duplex molecule with the enzyme EcoRI. A "spiked" oligo

CAGACGGTCTTGNNNNNNCGCNNNACCNNNGCCNNNATANNNGCCATAGTGGCT covering amino acid positions 30 to 58 of SE-83 was used.

Targeted random mutagenesis was carried out with the following oligonucleotide (SEQ ID NO: 43):

AAGGCGGTCCTGNNNNNNGACNNNGCCNNNCGCNNNATANNNATCGGCCTCGCC

Another TRM mutagenesis was carried out on the region

TTCCAGATTCGTGTCGGANNNNNNNNNNNNNNNNGGAGCCCACCCAGATCAT homologous to region 176–180 of SY-77 acylase. The mixed oligonucleotide (SEQ ID NO: 44) used was as follows:

CCAGAGCTTGAACCAGACGGANNNNNNNNNNNNNNNNCAGCCGCCGCATCACGGC

A second gap was created with the enzymes NotI and SmaI. This gapped duplex was mutagenized with a spiked oligonucleotide covering amino acid positions 730 to 746 of SE-83. TRM mutagenesis was carried out with the following oligonucleotide (SEQ ID NO: 45):

CACCATCGCGCANNNGCTCCANNNNNNATTCTGGTCGGCNNNGTGGGGCTGGC

Mutants were selected on aminoadipyl leucine or on aminoadipyl amide agar plates.

EXAMPLE 12

Mutagenesis of A. faecalis Acylase

In a pTZ18R subclone of the 4kb Sau3A-HpaI fragment of the pAF1 insert an NdeI site was constructed on the start codon of the A. faecalis gene with the aid of the following oligonucleotide (SEQ ID NO: 46):

G CCC TTT CTG CAT ATG TGT CCC TTA TTT TTA

After NdeI digestion of the resulting mutant plasmid pMaAFnde was constructed. After linearization with BamHI a gapped duplex with single stranded pMcAFNde was made. A spiked oligo covering region 37–46 was used for region mutagenesis and after transfer into E. coli WK6 Muts and subsequently E. coli HB101 the mutant library was selected on minimal plates with 10 µg/ml glutaryl leucine and 50 µg/ml cap. Those colonies which grew on these plates (and not on minimal plates) were tested for activity on glutaryl cephalosporin. A similar experiment with an oligo covering region 51–72 of A. faecalis was performed.

Targeted random mutagenesis (TRM) was performed on the same gapped duplex molecule using the following oligonucleotide (SEQ ID NO: 47):

The use of this oligo results in a substitution of positions 51, 53, 55, 57, 59 and 60 into all possible amino acids. Another TRM was carried out on the region homologous to positions 176–180 of SY-77acylase with the following mixed oligonucleotide (SEQ ID NO: 48):

A mutant library of $10^7$ mutants was generated and selected on aminoadipyl leucine or glutaryl leucine plates.

In another experiment a gapped duplex using NruI and MluI was made. This gapped duplex was mutagenized with a "spiked" oligonucleotide covering amino acid positions 761 to 790. The resulting mutant library was selected on glutaryl leucine and aminoadipyl leucine, respectively.

EXAMPLE 13

Mutagenesis of E. coli Acylase

The insert of plasmid pUNNEC1 was subcloned into vector pTZ18 using restriction sites HindIII and SmaI. With the following specific oligonucleotide (SEQ ID NO: 49) an NdeI site was created at the start codon:

TCTATTTTTCATATGATCCTCTGGCAG

The acylase gene was then subcloned into plasmid pMaTECNde using the restriction enzymes NdeI and SmaI. This plasmid was mutagenized with a "spiked" oligonucleotide covering amino acids 53 to 74 of *E. coli* acylase and selected in a similar way as described in Example 9.

Targeted random mutagenesis of *E. coli* Pen-acylase was carried out with a mixed oligo homologous to the positions 176–180 of SY-77 acylase. The following oligo (SEQ ID NO: 50) was used:

TTCGCTAGTGCTATCAGANNNNNNNNNNNNNNNNNGGTGCCCACAAATATCAT

All publications including patents and patent applications mentioned in this specification are indicative of the level of skill of those skilled in the art to which the invention pertains. All publications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

For example, it will be understood that selected mutants can be used for a consecutive round of mutagenesis with any of methods mentioned above or any of the mentioned spiked oligo's. Also a combination of two or more spiked oligo's in a single mutagenesis experiment is within the scope of this invention.

LIST OF REFERENCES

1. Lowe et al., Book Dev. Ind. Microbiol, 22, (1982) 163–180
2. Abbott B. J., Adv. Appl. Microb. 20 (1976), 203
3. Vandamme E. J., "Penicillin acylases and β-lactamases" In: "Microbial Enzymes and Bioconversions" E. H. Rose (Ed.), Economic Microbiology 5 (1980) 467–552, Acad. Press, New York
4. Ollson A. et al., Appl. Env. Microbiol. 49 (1985) 1084
5. Shibuya Y. et al., Agric. Biol. Chem. 45 (1981) 1561–1567
6. Matsuda A. et al., J. Bacteriol. 169 (1987) 5815–5820
7. Walton R. B., Devel. Ind. Microbiol. 5 (1964) 349–353
8. Mahajan P. B., Appl. Biochem. Biotechnol. 9 (1984) 537–553
9. Mayer et al., Adv. Biotechnol. 1 (1982) 83–86
10. Schumacher et al., Nucleic Acids Res. 14 (1986) 5713–5727
11. Barbero J. L. et al., Gene 49 (1986) 69–80
12. Daumy G. O. et al., J. Bacteriol. 163 (1985) 1279–1281
13. Dickerson R. E. & Geis I. in "Hemoglobin" Ed. Benjamin and Cummings (1983), Menlo Park Calif., U.S.A.
14. Blow D., Nature 343 (1990) 694–695
15. Winkler F. K. et al., Nature 343 (1990) 771–774
16. Brady L. et al., Nature 343 (1990) 767–770
17. Maniatis et al., "Molecular Cloning, A Laboratory Manual", Cold Spring Harbor Laboratory, 1982/1989
18. Ausubel et al., "Current Protocols in Molecular Biology", John Wiley and Sons, Inc., New York, 1987
19. Perbal B., "A Practical Guide To Molecular Cloning" 2nd, ed., John Wiley and Sons, Inc., New York, 1988
20. Nilsson et al., Nucleic Acids Res. 11 (1983) 8019
21. Reyes F. et al., J. Pharm. Pharmacol. 41 (1989) 136–137
22. Stanssens et al., Nucleic Acids Res. 17 (1989) 4441
23. De Boer et al., Proc. Natl. Acad. Sci. U.S.A. 80 (1983) 21–25
24. Hermes et al., Gene 84 (1989) 143–151
25. Leethovaara et al., Protein Eng. 2 (1989) 143–151
26. Garcia et al., J. Biotech. 3 (1986) 187–195
27. Sang-Jin et al., Gene 56 (1987) 87–97
28. Meevootisom et al., Appl. Microbiol. Biotechnol., 25 (1987)
29. Matsuda A. et al., J. Bacteriol. 163 (1985) 1222–1228
30. Matsuda A. et al., J. Bacteriol. 169 (1987) 5821–5826
31. Bruns W. et al., J. Mol. Appl. Gen. 3 (1985) 36–44
32. Underfriend S. et al., Science 178 (1972) 871–872
33. Williams J. A. et al., J. Cell Biochem. 9B/supplement (1985) p. 99, no. 656
34. Forney L. J. et al., Appl. Environ. Microbiol. 55 (1989) 2550–2555
35. Forney L. J. et al., Appl. Environ. Microbiol. 55 (1989) 2556–2560
36. Leung D. W. et al., Technique 1 (1989) 11

We claim:

1. An isolated mutant Type III β-lactam Pseudomonas SY-77 acylase comprising:

(1) a substitution at one or more selected sites corresponding to a residue position selected from the group consisting of 62, 177, 178 and 179 of wild-type Type II β-lactam Pseudomonas SY-77 glutaryl acylase; and (2) relative to said wild-type Type II β-lactam Pseudomonas SY-77 acylase, an altered substrate specificity.

2. A DNA sequence encoding a mutant acylase as defined in claim 1.

3. An expression vector which comprises a DNA sequence of claim 2.

4. A microorganism host strain transformed with an expression vector of claim 3.

5. A transformed microorganism host strain according to claim 4, wherein said host strain is a prokaryote.

6. A method of preparing an isolated mutant acylase enzyme, which method comprises:

growing a microorganism host strain transformed with an expression vector comprising a DNA sequence encoding a mutant acylase enzyme as defined in claim 1, whereby said mutant acylase enzyme is produced and isolating said enzyme.

7. A method for conducting an acylation or deacylation reaction, said process comprising:

contacting a mutant Type II β-lactam acylase as defined in claim 1 with a substrate for said acylase under conditions suitable for said reaction to occur.

8. A method for producing β-lactam compounds, said process comprising:

contacting a mutant Type II beta-lactam acylase as defined in claim 1, with a substrate for said acylase under conditions suitable for a deacylation reaction to occur, whereby a beta-lactam compound is produced.

9. An isolated mutant Type II β-lactam Pseudomonas SY-77 acylase comprising one or more mutations selected from the group consisting of:

(a) V62L;

(b) Y178H;

(c) V179G; and (d) L117I and Y178H.

* * * * *

UNITED STATES PATENT AND TRADEMARK OFFICE
CERTIFICATE OF CORRECTION

PATENT NO.   : 5,457,032
DATED        : October 10, 1995
INVENTOR(S)  : Quax et al.

It is certified that error appears in the above-identified patent and that said Letters Patent is hereby corrected as shown below:

Column 4,
Line 3, change "specifity" to -- specificity --
Line 28, change "pUCGLTA" to -- pUCGL7A --
Line 40, change "the/SE-83" to -- the SE-83 --

Column 8,
Line 22(?), change "B-subunit" to -- β-subunit --

Column 12,
Line 41, change "FIG. 5" to -- FIGS. 5A-5C --

Column 13,
Line 57, change "FIGS. 14-14C" to -- FIGS. 14A-14C --

Column 16,
Line 45, change "FIG. 14" to -- FIG. 14A-14C --

Column 17,
Line 20, change "5-subunit" to -- β-subunit --
Line 37, change "Type IIb" to -- Type-IIB --
Line 48, change "type IIB" to -- Type-IIB --

Column 19,
Line 15, change "suplemented" to -- supplemented --

Column 20,
Line 24, change "Targetted" to -- Targeted --

Column 21,
Line 14, change "oligo:" to -- oligo (SEQ ID NO: 37): --

UNITED STATES PATENT AND TRADEMARK OFFICE
CERTIFICATE OF CORRECTION

PATENT NO.    : 5,457,032
DATED         : October 10, 1995
INVENTOR(S)   : Quax et al.

It is certified that error appears in the above-identified patent and that said Letters Patent is hereby corrected as shown below:

Column 26,
Line 52, change "(1987)" to -- (1987) 372-378 --

Claim 1,
Line 1, change "Type III" to -- Type II --

Signed and Sealed this

Twenty-fifth Day of September, 2001

Attest:

NICHOLAS P. GODICI
*Acting Director of the United States Patent and Trademark Office*

*Attesting Officer*